United States Patent
Blackaby et al.

(10) Patent No.: US 10,155,259 B2
(45) Date of Patent: Dec. 18, 2018

(54) FSH RECEPTOR ANTAGONISTS

(71) Applicant: Merck Sharp & Dohme B.V., Haarlem (NL)

(72) Inventors: Wesley Peter Blackaby, Saffron (GB); Martin De Kort, Oss (NL); Mark Enthoven, Oss (NL); Paul Stuart Hinchliffe, Saffron (GB); Christian Bernard Matthijs Poulie, Oss (NL); Cornelis Marius Timmers, Oss (NL); Saskia Verkaik, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 807 days.

(21) Appl. No.: 14/812,739

(22) Filed: Jul. 29, 2015

(65) Prior Publication Data

US 2015/0329545 A1 Nov. 19, 2015

Related U.S. Application Data

(63) Continuation of application No. 14/346,203, filed as application No. PCT/EP2012/068080 on Sep. 14, 2012, now Pat. No. 9,127,007.

(60) Provisional application No. 61/537,563, filed on Sep. 11, 2011.

(30) Foreign Application Priority Data

Sep. 22, 2011 (EP) .................................. 11182306

(51) Int. Cl.
*C07D 471/04* (2006.01)
*C07D 471/14* (2006.01)
(Continued)

(52) U.S. Cl.
CPC ........ *B21D 53/745* (2013.01); *A61K 31/4375* (2013.01); *A61K 31/475* (2013.01); *Y10T 29/49908* (2015.01); *Y10T 29/5397* (2015.01)

(58) Field of Classification Search
CPC .............. B21D 53/745; A61K 31/4375; A61K 31/475; Y10T 29/49908
USPC .......................................................... 546/82
See application file for complete search history.

(56) References Cited

U.S. PATENT DOCUMENTS

| 8,431,564 B2* | 4/2013 | Timmers | A61K 31/397 514/210.21 |
| 8,993,757 B2* | 3/2015 | Huisman | C07D 401/14 544/212 |
| 9,044,463 B2* | 6/2015 | Blackaby | C07D 405/14 |
| 9,127,007 B2 | 9/2015 | Blackaby et al. | |

FOREIGN PATENT DOCUMENTS

| WO | 2003/051877 A1 | 6/2003 |
| WO | 2007/017289 A2 | 2/2007 |

(Continued)

OTHER PUBLICATIONS

Guo; Expert Opin. Ther. Patents 2005, 15, 1555-1564. (Year: 2005).*

(Continued)

*Primary Examiner* — Daniel R Carcanague
(74) *Attorney, Agent, or Firm* — Janet E. Fair; Catherine D. Fitch

(57) ABSTRACT

The invention relates to FSH receptor antagonist according to general formula I (Continued)

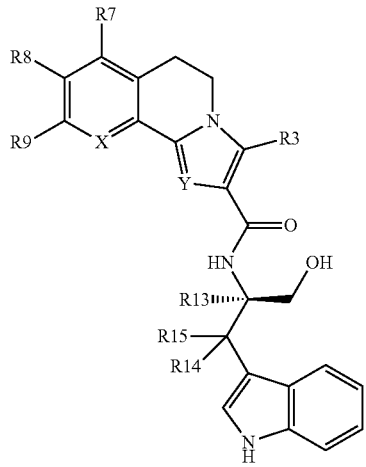

Formula I or a pharmaceutically acceptable salt thereof and to a pharmaceutical composition containing the same. The compounds can be used for the treatment and prevention of endometriosis, for the treatment and prevention of pre-menopausal and peri-menopausal hormone-dependent breast cancer, for contraception, and for the treatment of uterine fibroids and other menstrual-related disorders.

12 Claims, 1 Drawing Sheet

(51) Int. Cl.
A61K 31/4375 (2006.01)
A61K 31/475 (2006.01)
B21D 53/74 (2006.01)

(56) References Cited

FOREIGN PATENT DOCUMENTS

| WO | 2008/071455 A1 | 6/2008 |
| WO | 2009/098283 A1 | 8/2009 |
| WO | 2013/041458 A1 | 3/2013 |

OTHER PUBLICATIONS

Struthers; J Clin Endocrinol Metab, 2009, 94, 545-551. (Year: 2009).*
International Search Report for PCT/EP2012/068080 dated Nov. 22, 2012.

* cited by examiner

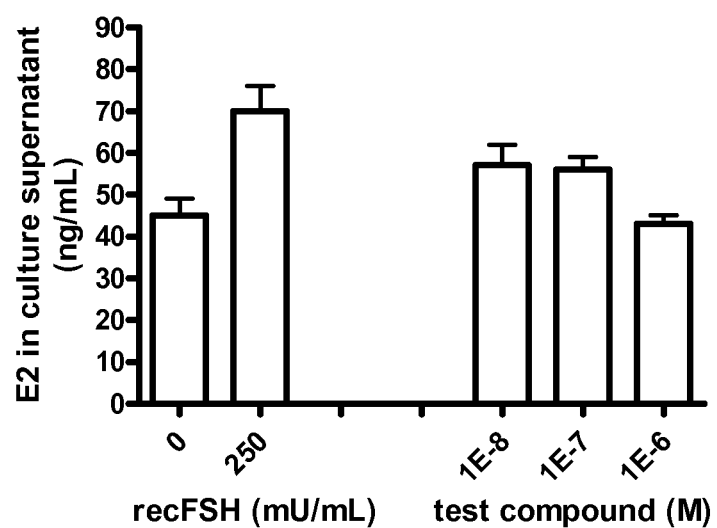

FSH RECEPTOR ANTAGONISTS

CROSS-REFERENCE TO RELATED APPLICATIONS

The present application is a continuation application of U.S. application Ser. No. 14/346,203 filed May 5, 2014, which is a U.S. National Phase application under 35 U.S.C. § 371 of PCT/EP2012/068080, filed Sep. 14, 2012, which claims priority from U.S. provisional Application Ser. No. 61/537,653, filed Sep. 11, 2011.

BACKGROUND OF THE INVENTION

The invention relates to a compound having FSH receptor modulatory activity, to a pharmaceutical composition containing the same, as well as the use of said compound for FSH receptor mediated diseases.

Gonadotropins are important in a variety of bodily functions including metabolism, temperature regulation and the reproductive process. Gonadotropins act on specific gonadal cell types to initiate ovarian and testicular differentiation and steroidogenesis. The hypophyseal gonadotropin FSH (follicle stimulating hormone) for example is released from the anterior pituitary under the influence of gonadotropin-releasing hormone and estrogens and plays a pivotal role in the stimulation of follicle development and maturation. FSH is the major hormone regulating secretion of follicular estrogens, whereas LH (luteinizing hormone) stimulates the production of follicular testosterone and induces ovulation (Sharp, R. M. Clin Endocrinol. 33:787-807, 1990; Dorrington and Armstrong, Recent Prog. Horm. Res. 35:301-342, 1979).

The actions of the FSH hormone are mediated by a specific plasma membrane receptor that is a member of the large family of G-protein coupled receptors. These receptors consist of a single polypeptide with seven transmembrane domains and are able to interact with the Gs protein, leading e.g. to the activation of adenylate cyclase.

The FSH receptor (FSHR) is a highly specific target in the ovarian follicle growth process and is exclusively expressed in the ovary. Blocking this receptor or inhibiting the signaling which is normally induced after FSH-mediated receptor activation will disturb follicle development and thus production of estrogens, ovulation and fertility. Low molecular weight FSH receptor antagonists, henceforth termed FSHR antagonists, could therefore form the basis for medical therapies that are in need of diminished production of estrogens and/or induction of anovulation.

Low molecular weight FSH receptor antagonists have been disclosed in International Applications WO 2008071455, WO 200807145 and WO 2008117175 and in van Straten, N. C. R. and Timmers, C. M. Annual Reports in Medicinal Chemistry 44:171-188, 2009 and van Straten, N. C. R. et al J. Med. Chem. 48:1697-1700, 2005.

Preventing or reversing endometriosis is an important goal in the field of women's health care. Endometriosis is a painful gynaecological condition that is characterized by the presence of endometrial tissue in sites outside of the uterine cavity. The prevalence rate is approximately 10% but this may be an underestimate because of the need to perform a laparoscopic procedure to determine the presence of disease. The disease affects women of reproductive age, the most common symptoms being painful menstruation (dysmenorrhoea), pain during intercourse (dyspareunia), painful bowel movement (dyschezia), chronic pelvic pain, heavy periods (menorrhagia), and infertility. If left untreated or inadequately treated endometriosis can either progress or spontaneously regress. In a significant number of women endometriosis is a chronic progressive disease manifesting itself as intractable pain, worsening quality of life, and infertility.

The etiology is unclear which also hampers an understanding of the symptomatic implications of the disease. Endometriosis produces an array of symptoms of varying severity with lack of correlation between stage of disease, disease load and degree of pain thereby causing confusion with clinical classification and delay in diagnosis. Known treatment options are drug therapy and conservative surgery.

Drug therapy is with analgesics, hormonal contraceptives which contain both estrogen and progestagen (Combined Oral Contraceptive (COC)) or progestagen only (Progestagen-Only Contraceptive (POC)), gonadotropin releasing hormone (GnRH) agonists, or other hormones e.g. danazol. Oral contraceptive regimens with combined use of an estrogen and a progestagen (COC) are widely used as first-line therapy in suspected or diagnosed endometriosis, owing to their property to provide cycle control, reduce menstrual flow and eradicate dysmenorrhoea, the most common symptom especially in early-stage disease. However, no single product offers sufficient efficacy in combination with a tolerable level of side effects. COCs may treat some of the symptoms well, but do not effectively suppress the progress of endometriosis and do not effectively treat chronic pelvic pain.

COCs produce initial decidualization of the endometrium by creating a state of pseudocyesis and later atrophy and thinning of the endometrium, thereby providing cycle control, reduction in menstrual flow and reduction of dysmenorrhoea. COCs may treat therefore menstruation-related symptoms but they do not completely suppress the growth of endometriotic lesions and associated chronic pelvic pain.

The mechanism of action of progestagens is initial decidualization of endometrium, followed by atrophy as a result of a direct suppressive effect on estrogen receptors in the endometrium. There is evidence that progestagens suppress matrix metalloproteinases at the molecular level thereby inhibiting the growth of ectopic endometrium. Medroxyprogesterone acetate is the most widely used progestagen for the treatment of endometriosis. Although available for oral administration, medroxyprogesterone acetate is usually administered as a depot formulation every 3 months. The side effects of POCs are multiple, the most common being breakthrough bleeding, nausea, fluid retention and breast tenderness.

GnRH agonists and GnRH antagonists down-regulate the Hypothalamus-Pituitary-Ovary axis by downregulation of the GnRH receptor and GnRH receptor-mediated signalling, resulting in a hypo-estrogenic menopausal state, endometrial atrophy, and amenorrhoea. Although very effective in reducing circulating levels of estrogens, multiple side effects related to menopausal symptoms as well as osteoporosis limit duration of treatment with GnRH agonists to 6 months.

Known drug treatments and/or conservative surgery offer temporary relief only and relapse rates can be as high as 50% with a major impact on fertility and quality of life. Moreover, a significant number of women aged 40-44 years require hysterectomy and bilateral salpingo-oophorectomy.

There is thus a strong need for early therapeutic intervention that improves on the above-mentioned shortcomings of available treatment options. The need is in particular for early therapeutic intervention that suppresses progression of disease and/or improves the side-effect profile (i.e. unscheduled bleeding, bone loss and menopausal symptoms) and improves fertility outcomes.

DETAILED DESCRIPTION OF THE INVENTION

The present invention therefore relates to FSHR antagonists as a means for the treatment and prevention of endometriosis, for the treatment and prevention of pre-menopausal and peri-menopausal hormone-dependent breast cancer, for contraception, and for the treatment of uterine fibroids and other menstrual-related disorders, such as dysfunctional uterine bleeding. The present invention provides compounds having the general Formula I or a pharmaceutically acceptable salt thereof.

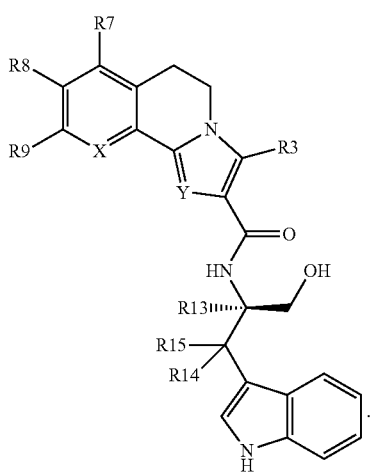

Formula I

In this Formula X, Y, R3, and R7, R8, R9, R13, R14 and R15 have the following definitions:
X is C(R10) or N;
Y is C(R1) or N;
R1 is H, (1-4C)alkyl, (2-4C)alkenyl or (2-4C)alkynyl;
R3 is phenyl, (2-8C)-heteroaryl, benzoyl, (2-8C)heteroarylcarbonyl, the phenyl or heteroaryl moieties of which may optionally be substituted with one or more substituents selected from R11, or
R3 is (1-6C)alkyl, (2-6C)alkenyl, (2-6C)alkynyl, (3-6C)cycloalkyl, (1-6C)alkylcarbonyl, (2-6C)alkenylcarbonyl, (2-6C)alkynylcarbonyl or (3-6C)cycloalkylcarbonyl;
R7 and R8 are independently H or (1-4C)alkoxy;
R9 is hydroxy or H, or
R9 is (1-6C)alkyl, (2-6C)alkenyl, (2-6C)alkynyl, (1-4C)alkoxy, (2-4C)alkenoxy, (3-6C)cycloalkyl, (3-6)cycloalkoxy, (3-6C)cycloalkyl(1-4C)alkoxy, (2-6C)heterocycloalkylcarbonyl, (di)[1-4C]alkylaminocarbonyl, (2-6C)heterocycloalkyl, the alkyl or (hetero)cycloalkyl moieties of which may optionally be substituted with one or more substituents selected from R12 or,
R9 is (2-8C)heteroaryl, phenyl, phenyl(1-4C)alkoxy, (2-8C)heteroaryl(1-4C)alkoxy, the phenyl or heteroaryl moieties of which may optionally be substituted with one or more substituents selected from R16;
R10 is H or (1-4C)alkoxy;
R11 is hydroxy, amino, halogen, nitro, trifluoromethyl, cyano, (1-4C)alkyl, (1-4C)alkoxy or (di)[1-4C)alkyl]amino;
R12 is hydroxy, amino, halogen, cyano, (1-4C)alkoxy or (di)[1-4C)alkyl]amino;
R13 and R14 are independently H or (1-3C)alkyl;
R15 is H, (1-3C)alkyl, or
R14 and R15 may be joined in a (3-6C)cycloalkyl ring; and
R16 is hydroxy, amino, halogen, nitro, trifluoromethyl, cyano, (1-4C)alkyl, (1-4C)alkoxy or (di)[1-4C)alkyl]amino.

The compounds according to the present invention have FSHR modulatory activity and dose titration with such FSHR antagonists give rise to diminished follicle development (no ovulation) and reduction of circulating levels of estrogens with still sufficient estrogen production left to avoid adverse effects on e.g. bone mass.

Without intending to be bound by theory, the compounds according to the present invention are able to provide optimal control over circulating levels of estrogens by the fact that the compounds are allosteric FSHR antagonists and will therefore be less sensitive to an increase in circulating levels of FSH due to a loss of feedback inhibition by decreased levels of circulating estrogens. Moreover, dose titration of the FSHR antagonist would allow for a second level of control over FSHR signalling and thus over the balance between efficacy (decrease in estrogens) and side effects (minimal level of residual estrogens).

In contrast to GnRHR (ant)agonist treatment regimens, the higher tolerability of FSHR antagonists enables treatment for periods exceeding 6 months.

The term (1-3C)alkyl as used here above means a branched or unbranched alkyl group having 1-3 carbon atoms, being methyl, ethyl, propyl and isopropyl.

The term (1-4C)alkyl means a branched or unbranched alkyl group having 1-4 carbon atoms, being methyl, ethyl, propyl, isopropyl, butyl, isobutyl, sec-butyl and tert-butyl.

The term (1-6C)alkyl means a branched or unbranched alkyl group having 1-6 carbon atoms, for example methyl, ethyl, propyl, isopropyl, butyl, tert-butyl, n-pentyl and n-hexyl. (1-5C)Alkyl groups are preferred, (1-4C)alkyl being the most preferred.

The term (1-4C)alkoxy means an alkoxy group having 1-4 carbon atoms, the alkyl moiety having the same meaning as previously defined. (1-3C)Alkoxy groups are preferred.

The term (1-6C)alkylcarbonyl means an alkylcarbonyl group, the alkyl group of which contains 1-6 carbon atoms with the same meaning as previously defined.

The term (2-4C)alkenyl means a branched or unbranched alkenyl group having 2-4 carbon atoms, such as ethenyl, propenyl and 2-butenyl.

The term (2-6C)alkenyl means a branched or unbranched alkenyl group having 2-6 carbon atoms, such as ethenyl, 2-butenyl, and n-pentenyl.

The term (2-6C)alkenylcarbonyl means an alkenylcarbonyl group, the alkenyl group of which contains 2-6 carbon atoms with the same meaning as previously defined.

The term (2-4C)alkenoxy means an alkenoxy group, the alkenyl group of which contains 2-4 carbon atoms with the same meaning as previously defined.

The term (2-4C)alkynyl means a branched or unbranched alkynyl group having 2-4 carbon atoms, such as ethynyl, propynyl and butynyl.

The term (2-6C)alkynyl means a branched or unbranched alkynyl group having 2-6 carbon atoms, such as ethynyl, propynyl and n-pentynyl.

The term (2-6C)alkynylcarbonyl means an alkynylcarbonyl group, the alkynyl group of which contains 2-6 carbon atoms with the same meaning as previously defined.

The term (3-6C)cycloalkyl means a cycloalkyl group having 3-6 carbon atoms, such as cyclopropyl, ethylcyclopropyl, cyclobutyl, methylcyclobutyl, cyclopentyl and cyclohexyl.

The term (3-6C)cycloalkylcarbonyl means a cycloalkylcarbonyl group, the cycloalkyl group of which contains 3-6 carbon atoms with the same meaning as previously defined.

The term (3-6C)cycloalkoxy means a cycloalkoxy group having 3-6 carbon atoms, such as cyclopropoxy, ethylcyclopropoxy, cyclobutoxy and cyclopentoxy.

The term (3-6C)cycloalkyl(1-4C)alkoxy means a cycloalkylalkoxy group, the cycloalkyl group of which contains 3-6 carbon atoms with the same meaning as previously defined and the alkoxy group of which contains 1-4 carbon atoms with the same meaning as previously defined.

The term (2-6C)heterocycloalkyl means a heterocycloalkyl group having 2-6 carbon atoms, preferably 3-5 carbon atoms, including 1-3 heteroatoms selected from N, O and/or S, which may be attached via a nitrogen if feasible, or a carbon atom. Preferred heteroatoms are N or O. Preferred number of heteroatoms is one or two. Most preferred are piperidin-1-yl, morpholin-4-yl, pyrrolidin-1-yl and piperazin-1-yl.

The term (2-8C)heteroaryl means an aromatic group having 2-8 carbon atoms and 1-4 heteroatoms selected from N, O and S, like imidazolyl, thiadiazolyl, pyridinyl, thienyl, oxazolyl, imidazolyl, pyrazolyl, furyl or indolyl. Preferred number of heteroatoms is one or two. Preferred heteroaryl groups are thienyl, oxazolyl, imidazolyl, pyrazolyl, pyrimidinyl, pyrazinyl, furyl and pyridinyl. Most preferred are thienyl, furyl and pyridinyl. The (2-8C)heteroaryl group may be attached via a carbon atom or a nitrogen, if feasible.

The term (di)[(1-4C)alkyl]amino as used herein means an amino group, monosubstituted or disubstituted with alkyl group(s), each containing 1-4 carbon atoms and having the same meaning as previously defined.

The term (di)[(1-4C)alkyl]aminocarbonyl means a (di) alkylaminocarbonyl group, the alkyl group(s) of which each contain(s) 1-4 carbon atoms with the same meaning as previously defined.

The term phenyl(1-4C)alkoxy means a phenylalkoxy group, the alkoxy group of which contains 1-4 carbon atoms with the same meaning as previously defined.

The term (2-8C)heteroaryl(1-4C)alkoxy means a heteroarylalkoxy group, the heteroaryl group of which contains 2-8 carbon atoms with the same meaning as previously defined and the alkoxy group of which contains 1-4 carbon atoms with the same meaning as previously defined.

The term (2-8C)heteroarylcarbonyl means a heteroarylcarbonyl group, the heteroaryl group of which contains 2-8 carbon atoms with the same meaning as previously defined.

The term (2-6C)heterocycloalkylcarbonyl means a heterocycloalkylcarbonyl group, the heterocycloalkyl group of which contains 2-6 carbon atoms with the same meaning as previously defined.

The term halogen means fluorine, chlorine, bromine or iodine.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

In the above definitions with multifunctional groups the attachment point is at the last group.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one aspect the invention relates to compounds according to Formula I wherein R1 is H or (1-4C)alkyl; R8 is (1-4C)alkoxy; R9 is hydroxy or R9 is (1-6C)alkyl, (2-6C)alkenyl, (1-4C)alkoxy, (2-4C)alkenoxy, (3-6)cycloalkoxy, (3-6C)cycloalkyl(1-4C)alkoxy, (2-6C)heterocycloalkylcarbonyl, (di)[1-4C]alkylaminocarbonyl, the alkyl or (hetero)cycloalkyl moieties of which may optionally be substituted with one or more substituents selected from R16 or R9 is (2-8C)heteroaryl, phenyl(1-4C)alkoxy, the phenyl or heteroaryl moieties of which may optionally be substituted with one or more substituents selected from R11.

In another aspect the invention relates to compounds according to Formula I wherein Y is C(R1).

In yet another aspect the invention relates to compounds according to Formula I wherein R1 is H.

In another aspect the invention relates to compounds according to Formula I wherein R13, R14 and R15 are H.

The invention also relates to compounds according to Formula I wherein R9 is (1-6C)alkyl, (1-4C)alkoxy or (3-6C)cycloalkyl(1-4C)alkoxy. The alkyl moieties of these groups may optionally be substituted with one or more substituents selected from R12. R9 might also be (2-8C)heteroaryl or phenyl(1-4C)alkoxy, the phenyl or heteroaryl moieties of which may optionally be substituted with one or more substituents selected from R11.

In a further aspect the invention relates to compounds according to Formula I wherein R3 is phenyl, (2-8C)-heteroaryl, benzoyl, (2-8C)heteroarylcarbonyl. The phenyl or heteroaryl moieties may optionally be substituted with one or more substituents selected from R11, R3 might also be (1-6C)alkyl, (2-6C)alkenyl, (1-6C)alkylcarbonyl or (3-6C)cycloalkylcarbonyl.

In still another aspect the invention resides in compounds according to Formula I wherein R3 is phenyl or (2-8C)-heteroaryl, both optionally substituted with one or more substituents selected from R11.

In another aspect the invention resides in compounds according to Formula I wherein X is C(R10).

The invention also relates to compounds according to Formula I wherein the optional substituent R11 in R3 is hydroxy, amino, halogen, nitro, trifluoromethyl, cyano, (1-4C)alkyl or (1-4C)alkoxy.

The invention also relates to compounds according to Formula I wherein the optional substituent R12 in R9 is hydroxy, (1-4C)alkoxy or (di)[1-4C)alkyl]amino.

The invention also relates to compounds according to Formula I wherein the optional substituent R16 in R9 is (1-4C)alkyl, (1-4C)alkoxy or (di)[1-4C)alkyl]amino.

The invention also relates to those compounds wherein all specifications for X, Y, R1, R3 and R7 through R16 in the various aspects of the invention as described hereabove occur in any combination within the definition of the compound according to Formula I.

In another aspect the invention relates to compounds of Formula I which have a pIC50 of 5 or higher. In yet another aspect the invention relates to compounds according to Formula I with a pIC50 of more than 7.

In yet another aspect the invention resides in the compounds according to Formula I selected described in examples 1-71.

The skilled artisan will recognize that desirable IC50 values are dependent on the compound tested. For example, a compound with an IC50 value which is less than $10^{-5}$ M is generally considered a candidate for drug selection. Preferably, this value is lower than $10^{-7}$ M. However, a compound which has a higher IC50 value, but is selective for the particular receptor, may be even a better candidate.

In vitro assays to determine receptor binding or the biological activity of gonadotropin receptor agonists and antagonists are well-known. In general, cells expressing the receptor are incubated with the compound to be tested and the binding or stimulation or inhibition of a functional response is determined. To measure a functional response, isolated DNA encoding the FSH receptor gene, preferably the human receptor, is expressed in a suitable host cell-line. Such a host cell-line might be the Chinese Hamster Ovary cell-line, but other cell-lines can also be used. Preferably, the host cells are of mammalian origin (Jia et al (1991) Mol Endocrinol 5, 759-776).

Methods to construct FSH receptor-expressing cell lines are well-known in the art (e.g., Sambrook et al., Molecular Cloning: A Laboratory Manual, Cold Spring Harbor Laboratory Press, latest edition). Heterogolous expression of the receptor is obtained by transfection and expression of the DNA encoding the desired protein. Techniques for site-directed mutagenesis, ligation of additional sequences, PCR, and construction of suitable expression systems are also well-known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well-known, expression systems are available, which are compatible with a wide variety of hosts, including prokaryotic hosts such as bacteria and eukaryotic hosts such as yeast, plant cells, insect cells, avian cells, mammalian cells, and the like.

Cells expressing the receptor are then incubated with the test compound to determine binding, or stimulation or inhibition of a functional response. Alternatively, isolated cell membranes containing the expressed receptor may be used to measure binding of compound.

For measurement of binding, radioactively- or fluorescently-labeled compounds may be used. Alternatively, competition binding assays may be performed. FSH receptor antagonistic compounds can also be identified in screening assays that involve the determination of receptor-mediated cAMP accumulation. Such methods involve the expression of the FSH receptor in a host cell-line and incubation of the cells with a concentration range of the test compound in the presence of a fixed, submaximally effective, FSH concentration (i.e., a FSH concentration that induces approximately 80% of the maximal cAMP accumulation by FSH in the absence of test compound). The amount of cAMP is then measured. From the concentration-effect curves, the IC50 value and the percentage of inhibition of FSH-induced cAMP accumulation can be determined for each of the compounds. As agonist, human recombinant FSH can be used.

In addition to the direct measurement of cAMP levels in the FSH receptor-expressing cell-line, cell-lines may be transfected with a second cDNA that encodes a reporter gene, of which the expression is dependent on the intracellular concentration of cAMP. Such reporter genes might be cAMP-inducible or be constructed in such a way that they are connected to novel cAMP responsive elements. In general, reporter gene expression might be controlled by any response element reacting to changing levels of intracellular cAMP. Suitable reporter genes are e.g. the genes encoding beta-galactosidase, alkaline phosphatase, firefly luciferase and green fluorescence protein. The principles of such transactivation assays are well-known in the art and are described for example in Stratowa et al (1995) Curr Opin Biotechnol 6, 574. Changes in intracellular cAMP levels may also be determined in live-cell cAMP biosensor assays, like the GloSensor™ cAMP assay, which uses a genetically encoded biosensor with a cAMP binding domain fused to a mutant form of luciferase, or the ACT One™ cAMP assay, which utilizes a cAMP-gated ion channel as a biosensor. Antagonistic compounds may also be identified in assays that are based on receptor-induced recruitment of beta-arrestin to the agonist-occupied receptor (e.g., Transfluor® assay, PathHunter® and Tango™ beta-arrestin assays) or receptor internalization assays (e.g., PathHunter® endocytosis assays). Label-free assays may also be applicable to screen for FSH receptor antagonists. These assays are based on receptor-induced dynamic mass redistribution of intracellular content or receptor-induced changes in cell morphology or adhesion (Van Koppen (2010) Drug Discovery tb 7, 69).

The compounds of Formula I can form salts which are also within the scope of this invention. Reference to a compound of Formula I herein is understood to include reference to salts thereof, unless otherwise indicated.

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press and Jana S. et al, Current Med. Chem. 17, 3874-3908, 2010. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also relates to a pharmaceutical composition comprising compounds or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a compound of Formula I in combination with one or more other drug(s).

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The present disclosure describes the preparation of low molecular weight compounds that show selective modulatory activity on the FSH receptor. The compounds of the invention can be used as (partial) antagonists of the FSH receptor.

The present invention therefore relates to FSHR antagonists as a means for the treatment and/or prevention of endometriosis, for the treatment and/or prevention of pre-menopausal and peri-menopausal hormone-dependent breast cancer, for contraception, and for the treatment of uterine fibroids and other menstrual-related disorders, such as dysfunctional uterine bleeding.

Thus, the compounds according to the invention can be used in therapy.

A further aspect of the invention resides in the use of compounds according to the invention or a pharmaceutically acceptable salt thereof for the treatment of FSH receptor-mediated diseases.

Another aspect of the invention resides in the use of compounds or a pharmaceutically acceptable salt thereof having the general formula I for the treatment of diseases wherein FSHR mediated signaling plays a role, in particular those diseases wherein signaling can be inhibited by antagonizing the FSHR. These include, but are not limited to, the treatment and prevention of endometriosis, for the treatment and prevention of pre-menopausal and peri-menopausal hormone-dependent breast cancer, for contraception, and for the treatment of uterine fibroids and other menstrual-related disorders, such as dysfunctional uterine bleeding.

In a further embodiment of the invention, a compound according to the invention is used to treat endometriosis by providing improved control over circulating levels of estrogens by dose titration thereby allowing optimal control over the balance between efficacy and side effects. Moreover, the selective on-target interaction with the FSHR will not impede LHR mediated signalling and associated production of testosterone. With the improvement in tolerability, a compound according to the present invention can also provide a simple effective treatment, preferably by the oral route of administration, in an early stage of the disease in a patient population familiar with contraceptive methods. Oral treatment is available by administration of a compound according to the invention in a pharmaceutical formulation. During treatment with a compound according to the invention, regular bleeding can be partially or completely avoided (inducing amenorrhoea). This is particularly useful in the treatment of endometriosis since it diminishes or prevents retrograde menstruation and thereby minimizes recurrence of disease.

A compound according to the invention can also be used for contraception. A compound according to the invention has therapeutic and contraceptive effect while inducing a mostly atrophic or inactive endometrium. This treatment thereby avoids endometrial proliferation or hyperplasia. Compounds according to the invention are also useful for treatment of other menstrual-related conditions such as fibroids and dysfunctional uterine bleeding. Furthermore, in view of the property of the compounds, according to the invention, to diminish circulating levels of estrogens, a compound according to the invention is also very useful for treatment of estrogen receptor positive breast cancer, either alone or in combination with an estrogen receptor antagonists such as tamoxifen or a selective estrogen receptor downregulator such as fulvestrant, in pre-menopausal and perimenopausal women.

Suitable methods to prepare the compounds of the present invention are outlined below.

The R-group numbering for compounds of general formula I. (R1, R3 and R7-10) refers to the position of the substituents relative to the scaffold, based on the 5,6-dihydropyrrolo[2,1-a]isoquinoline [X=C(R10), Y=C(R1)] numbering, as indicated below.

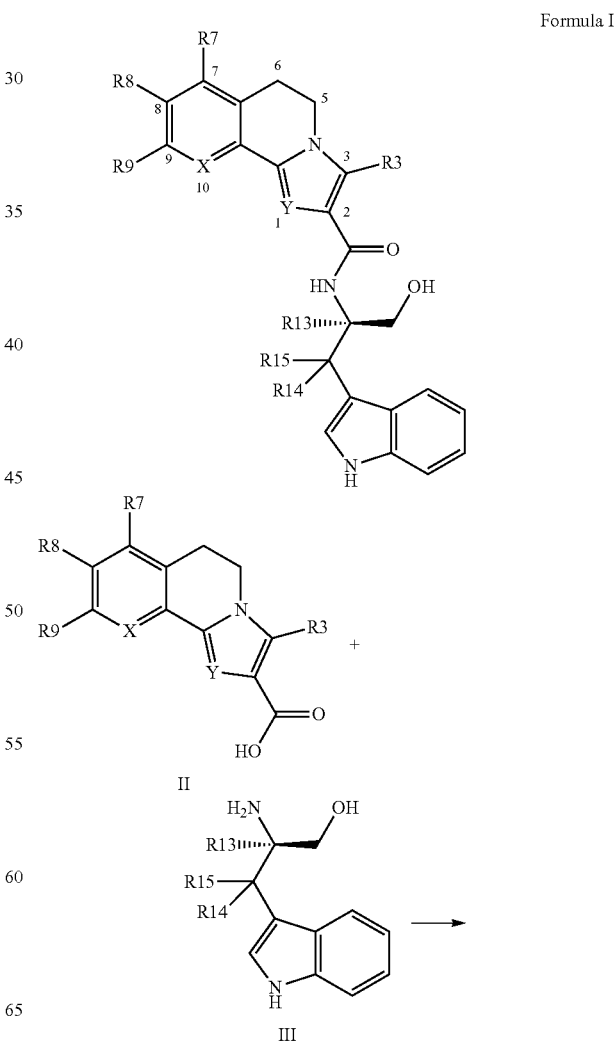

Formula I

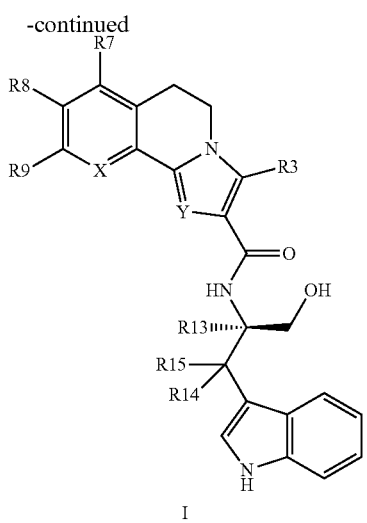

I

Compounds of general formula I are accessible by condensation of carboxylates of general structure II with tryptophanol derivatives of general formula III using methods well known to those skilled in the art. For example, reaction of II with III may be effected in an aprotic solvent such as THF or dichloromethane in the presence of a (commercially available) peptide coupling agent, like DCC, TBTU, HATU, EEDC, etc. and a suitable base, such as DiPEA. In turn, the required carboxylates II may be obtained from the corresponding ethyl esters of general formula IV by standard saponification. Thus, treatment of ethyl esters IV with NaOH in EtOH or dioxane/water mixtures at elevated or room temperature provides carboxylates II.

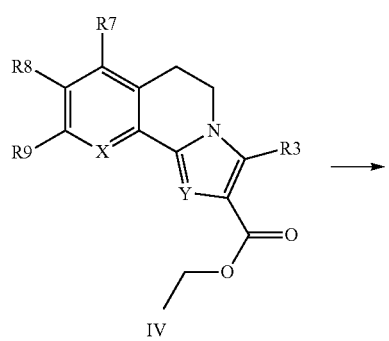

IV

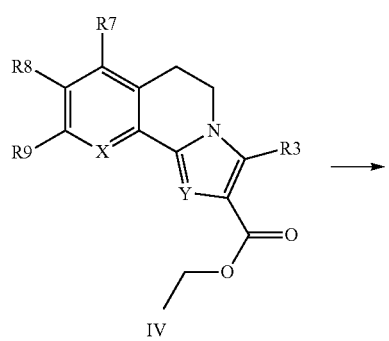

II

2-Substituted 5,6-dihydropyrrolo[2,1-a]isoquinolines of general formula IV-a, in which R3=H, X=C(R10) and Y=C(R1), are accessible by reaction of appropriately substituted dihydroquinolines of general structure V with (commercially available) ethyl bromopyruvate in the presence of a weak base, such as NaHCO₃. Related conversions have been described in: A. Tatarov et al., Tetrahedron 66, 995-1006 (2010). The 5,6-dihydropyrrolo[2,1-a]isoquinoline scaffold may be generated in an alternative fashion using 1,3-dipolar cycloadditions of acetylenes with munchnone intermediates as described extensively in the International Application WO 2009/098283 (N. V. Organon). In this process, often regioisomers are formed around positions 1 and 2 of the 5,6-dihydropyrrolo[2,1-a]isoquinoline framework, which may be separated by chromatography using methods such as HPLC or UPLC known to those skilled in the art.

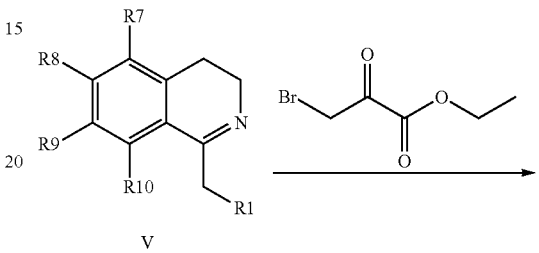

V

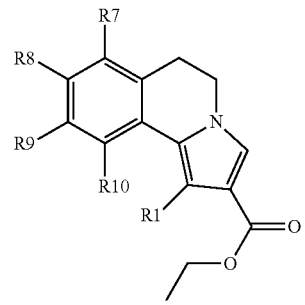

IV-a: X = C(R10),
Y = C(R1), R3 = H

Dihydroquinolines of general structure V may be obtained by Bischler-Napieralski-type cyclocondensation of acylated phenethyl amines VI, as described in: J. Jacobs et al., Tetrahedron Letters 50, 3698-3701 (2009). Typically, the amides VI are dissolved in an aprotic solvent such as toluene and treated with a dehydrating agent such as POCl₃, P₂O₅ or polyphosphoric acid (PPA) at elevated temperature to accomplish the cyclocondensation to dihydroquinolines V.

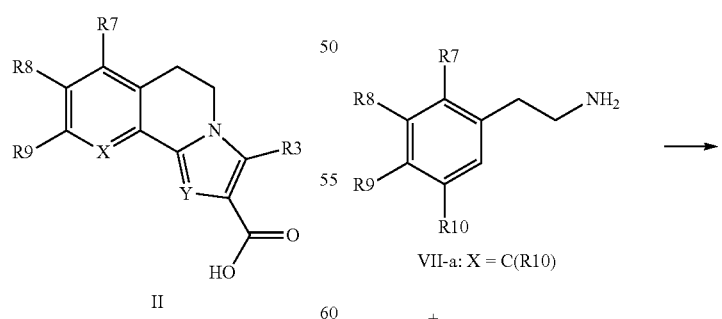

VII-a: X = C(R10)

+

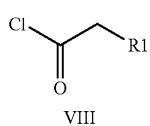

VIII

-continued

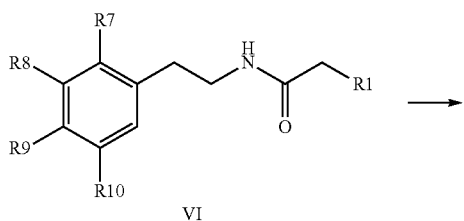

VI

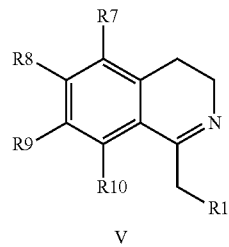

V

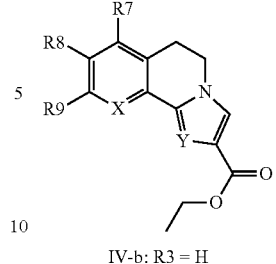

IV-b: R3 = H

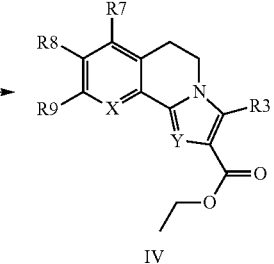

IV

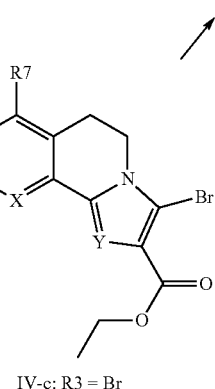

IV-c: R3 = Br

Phenethyl amides VI may be obtained by standard acylation of phenethyl amines VII-a with acyl chlorides of general formula VIII in an aprotic solvent, such as dichloromethane or THF, in the presence of a suitable base such as DiPEA at elevated temperature or room temperature, a procedure well known to those of skill in the art. Alkanoyl, alkenoyl or alkynoyl chlorides of general formula VIII, in which R1 has the same meaning as previously defined, are commercially available.

The appropriate phenethyl amines of general structure VII are either commercially available or are prepared readily via chloromethylation of appropriately substituted benzenes or pyridines, followed by conversion into cyanomethyl derivatives and reduction of the nitrile functionality, yielding the required phenethyl amines VII. Phenethyl amines VII are also accessible via Henry reaction of suitably substituted (commercially available) (hetero)aromatic aldehydes of general formula IX with nitromethane, followed by reduction of the intermediate nitro compounds X by hydride reagents (LiAlH$_4$, boranes etc.) in solvents such as THF, according to procedures well documented in literature.

Introduction of the required substituents R3 in compounds of general formula IV-b (R3=H) may be accomplished by organometal-catalyzed transformations, e.g. using organopalladium catalysts, based on derivatives of general formula IV-b. An effective methodology to introduce substituents R3 comprises Heck-type coupling with appropriately substituted halides R3-Br or R3-I. Heck-type coupling reactions are well known to those of skill in the art and typically involve the use of tetrakis(triphenylphosphine)palladium(0), palladium chloride or palladium(II) acetate as catalysts in the presence of a base such as triethylamine, potassium carbonate or sodium acetate. An overview of Heck-type conversions may be found in I. P. Beletskaya et al., Chem. Rev. 100, 3009-3066 (2000). In specific cases, introduction of R3 may require the presence of a bromide functionality at C-3 of the scaffold. Thus, compounds of general formula IV-c may be generated by regioselective bromination of compounds IV-b using standard bromination (e.g. N-bromosuccinimide) conditions, well known to those skilled in the art. Subsequently, compounds of general formula IV may be prepared by organopalladium-catalyzed transformations, such as Suzuki, Stille and Sonogashira couplings. Compounds of general formula IV, in which R3 contains a ketone functionality (e.g. R3=alkylcarbonyl) are accessible by generation of an anion at C-3 of the pyrrole or imidazole ring starting from compounds of general formula IV-b (deprotonation) or IV-c (transmetallation) with strong bases such as LDA in an aprotic solvent, followed by quenching with the appropriate acyl chloride (R3-Cl).

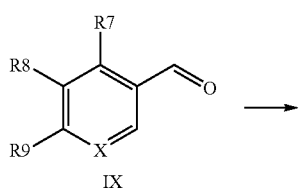

IX

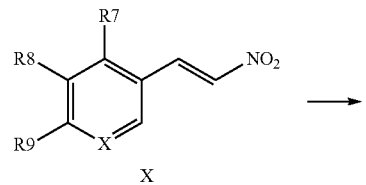

X

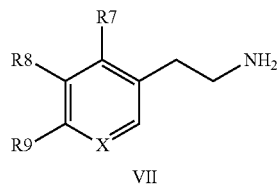

VII

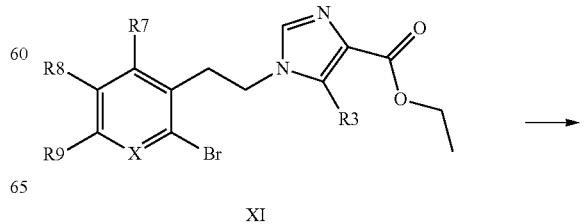

XI

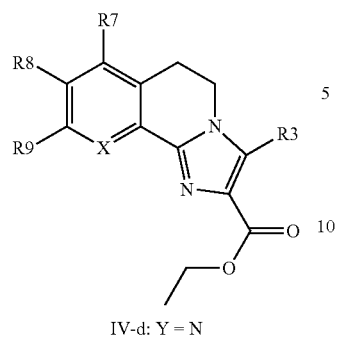

IV-d: Y = N

Compounds of general formula IV-d, in which Y=N, may be constructed by cyclization of bromides XI using Pd⁰ catalysis. In a typical experiment, the bromides XI are dissolved in an inert solvent, such as DMA and treated with Pd(PPh$_3$)$_4$ in the presence of a suitable base, such as Cs$_2$CO$_3$ at elevated temperature.

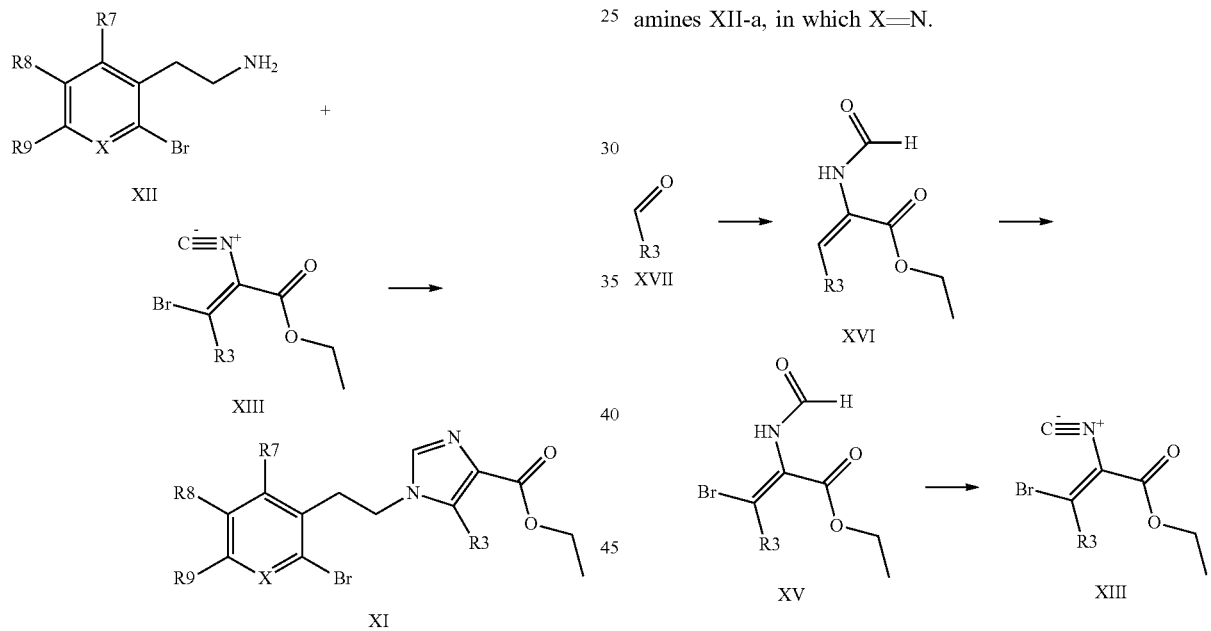

XII

XIII

XI

Imidazole derivatives XI are accessible by cyclization of appropriately functionalized (hetero)aryl ethyl amines XII with isocyanides XIII in an inert solvent, such as DMF, in the presence of a suitable base, such as triethyl amine. Related conversions have been described in: K. Nunami et al., *J. Org. Chem.* 59, 7635-7642 (1994) and K. Hiramatsu et al., *Synthesis*,

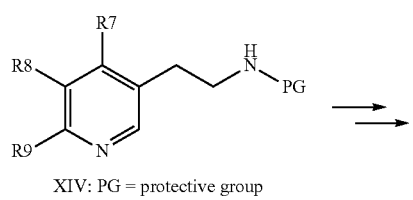

XIV: PG = protective group

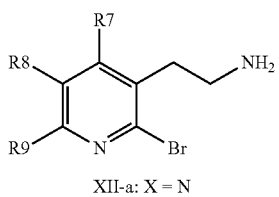

XII-a: X = N

The appropriate (hetero)aryl ethyl amines of general structure XII are either commercially available or may be prepared as described for the synthesis of phenethyl amines VII (vide supra). In case X=N, 2-bromination of the pyridine moiety may be effected using standard bromination conditions well known to those skilled in the art (e.g. N-bromosuccinimide), starting from suitably protected pyridines XIII, in which PG=protective group. For this purpose, the well known tert-butoxycarbonyl (Boc) protective group can be used, which may be unleashed after bromide introduction using standard (acidic) conditions, to provide amines XII-a, in which X=N.

XVII

XVI

XV

XIII

The required isocyanides XIII may be constructed in a multistep approach from commercially available aldehydes of general formula XVII. Thus, conversion of aldehydes XVII to unsaturated N-formyl esters XVI may be effected with ethyl isocyanoacetate in the presence of a strong base, such as NaH, in an inert solvent such as THF. Subsequent bromination of compounds XVI using N-bromosuccinimide in CCl$_4$, conditions well known to those of skill in the art, provides bromides XV. Compounds of general formula XV may undergo dehydration of the N-formyl moiety using a dehydrating agent such as POCl$_3$ in the presence of triethyl amine in an inert solvent such as dichloromethane, giving access to isocyanides of general formula XIII. The above delineated synthetic strategy has been described in: K. Nunami et al., *J. Org. Chem.* 59, 7635-7642 (1994).

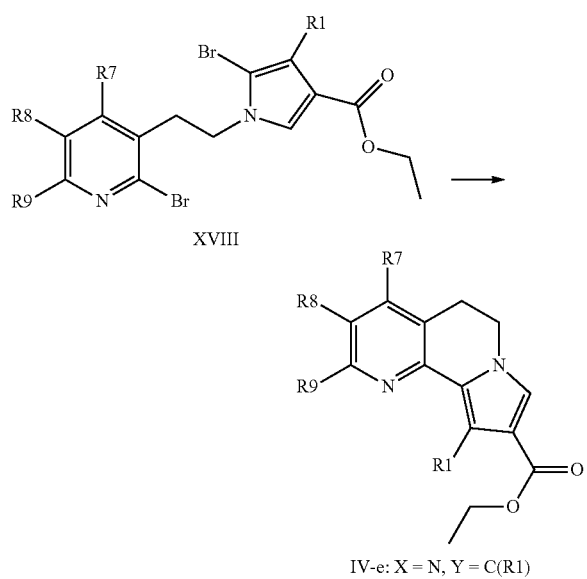

IV-e: X = N, Y = C(R1)

Preparation of heterocycles of general formula IV-e, in which X=N and Y=C(R1), requires a related, but slightly adapted synthetic procedure. Reductive ring-closure of 2-bromopyridines of general formula XVIII may be effected using (n-BuSn)$_2$ in the presence of a suitable palladium(II) catalyst, such as Pd(PPh$_3$)$_2$Cl$_2$ in an inert solvent such as DMF under microwave irradiation.

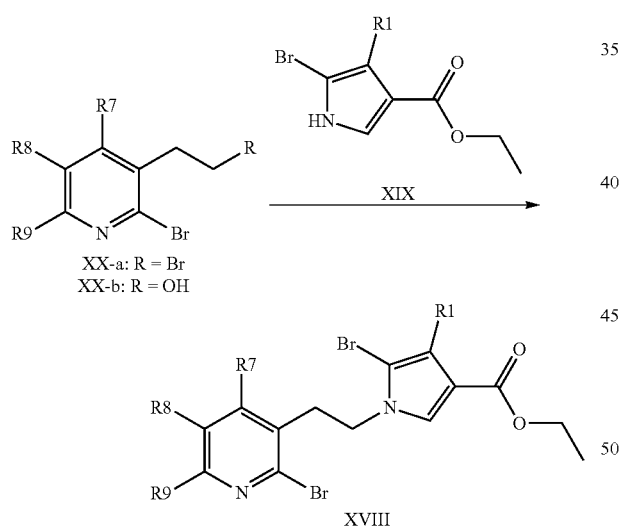

XX-a: R = Br
XX-b: R = OH

XVIII

The required 2-bromopyridines of general formula XVIII may be prepared from 3-pyridyl ethyl bromides XX-a or their corresponding primary alcohol derivatives XX-b, either by standard alkylation of bromides XIX at room temperature or elevated temperature in the presence of a suitable base (in case of XX-a) or by Mitsunobu-type alkylation (in case of XX-b) using dialkyl azodicarboxylates such as DIAD in the presence of triphenyl phosphine and a suitable base such as DiPEA. Both alkylation conditions may be considered part of the standard synthetic repertoire of those skilled in the art. Bromides of general formula XIX are either commercially available or accessible in elementary reaction steps from commercially available precursors. It is of importance to notice that the indicated conversions, such as XIX→XVIII→IV-e, may also be conducted with the corresponding methyl esters instead of ethyl esters. Those skilled in the art will appreciate that the above described ensuing conversions to arrive at compounds of general formula I in which X=N and Y=C(R1) are identical in case of methyl instead of ethyl esters and selection of the synthons will be guided by the (commercial) availability of the appropriately functionalized reagents.

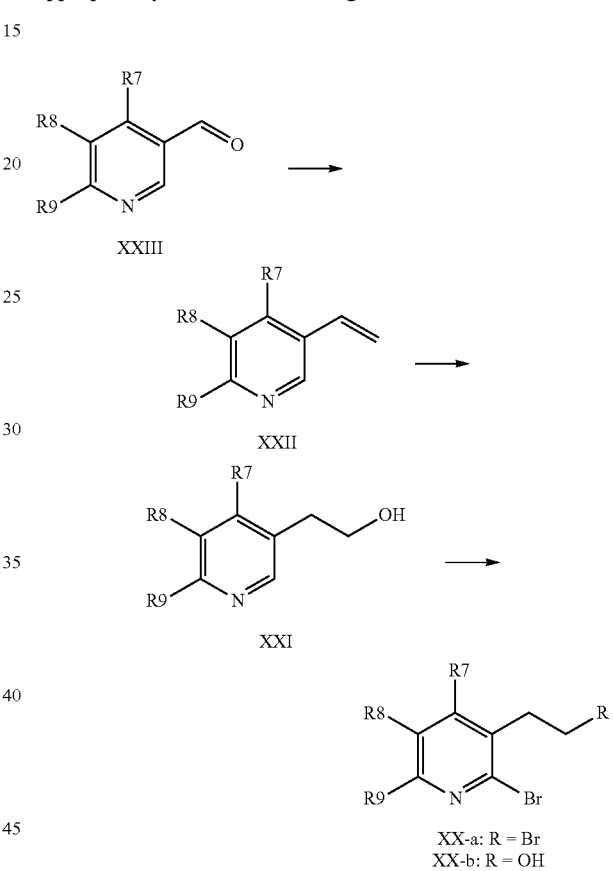

XX-a: R = Br
XX-b: R = OH

The suitably functionalized 2-bromopyridines of general formula XX-a/b are accessible from commercially available 3-pyridyl aldehydes XXIII in a straightforward sequence of reaction steps, well known to those of skill in the art. Methylenation of aldehydes XXIII using Wittig-type conversions (e.g. reaction with CH$_2$=PPh$_3$ in an inert solvent such as THF in the presence of a suitable base, or alternatively, using Tebbe's reagent) gives access to styrenes of general formula XXII. Ensuing hydroboration using appropriate borane derivatives, such as BH$_3$ or 9-borabicyclononane (9-BBN), followed by oxidative work-up with e.g. hydrogen peroxide, provides 3-pyridyl ethanol derivatives XXI. Finally, 2-pyridyl bromination using bromine in an inert solvent such as dichloromethane, then yields bromides of general formula XX-b. In specific cases, under the described conditions, concomitant bromination of the primary alcohol functionality occurs, giving access to bis-bromides XX-a.

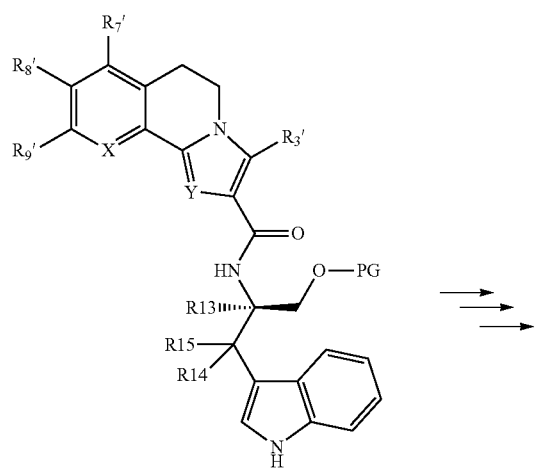

XXIV, Y = N or Y = C(R1'), X = N, or X = C(R10'),
PG = protective group

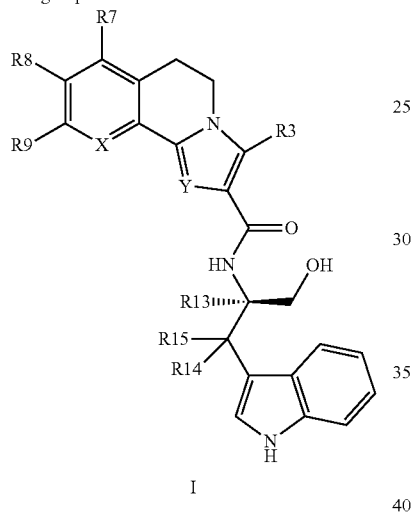

I

For the synthesis of compounds of general formula I the overall approach indicated above was employed, making use of tailor-made functionalized intermediates. This means that, depending on the required substituents R1, R3, R7-R10 (where R-numbering refers to the atom numeration in the scaffold), either the required substituents are brought in place at the beginning of the synthesis (i.e. R1=R1', R3=R3', etc.), or are introduced at any stage judged to be convenient in the course of the synthesis of the products of general formula I. In that case suitable alternative functionalities are introduced first, indicated as R1', R3', R7'-R10', which allow for the conversion into the desired R1, R3, R7-R10 in one or more additional manipulations (i.e. conversion of XXIV to I as indicated above), with R1, R3, R7-R10 having the same meaning as previously defined. It is of importance to notice that such conversions in most cases are not compatible with a free hydroxyl functionality, therefore a suitable hydroxyl-protecting group, as indicated in XXIV, is deemed necessary. Appropriate hydroxyl-protecting groups comprise silyl-ethers, such as tert-butyl-dimethylsilyl groups (TBDMS groups), which are introduced using standard conditions (i.e. treatment with TBDMS-Cl using an appropriate base, such as pyridine or DiPEA in an aprotic solvent such as dichloromethane or THF) well known to those of skill in the art and may be deprotected by acidic or fluoride ion (tert-butyl ammonium fluoride, TBAF) treatment at any stage considered to be convenient in the synthetic sequence leading to target derivatives of general formula I. Similarly, manipulation of substituents in an earlier stage of the synthetic protocol towards compound of general formula I, might be performed on compounds of general formula IV-f, in which R1', R3', R7'-R10' may be converted to R1, R3, R7-R10, as described above to provide derivatives of general formula IV.

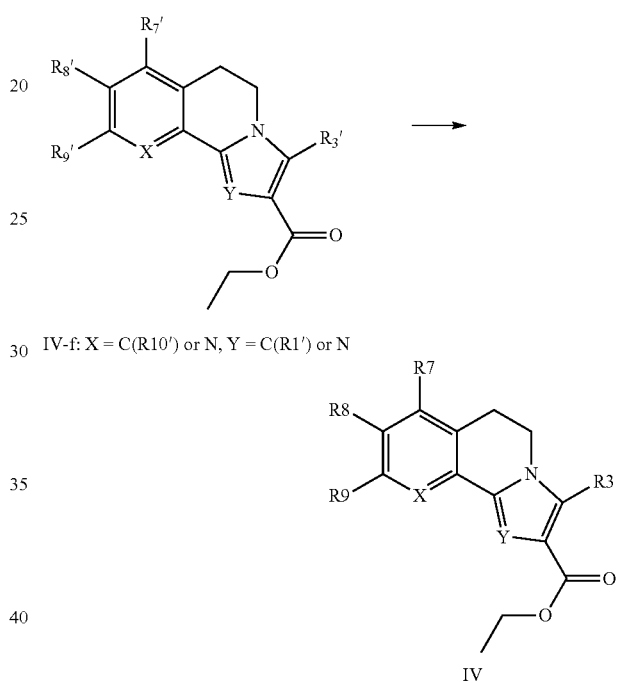

IV-f: X = C(R10') or N, Y = C(R1') or N

IV

In order to manipulate substituents at the C1, C3, C7, C8, C9 or C10 positions of the target scaffolds, halogen atoms like bromine, iodine or triflates can be used. Triflates, in turn, may be present in the initial precursors as methoxy groups, which, after demethylation using e.g. BBr$_3$, and subsequent triflation using e.g. triflic anhydride, provide the requisite tool compounds for further manipulation. Aromatic halides or triflates can be converted via well known organometallic reactions like Ullmann-, Suzuki-, Stille-, Sonogashira-, Heck- and Buchwald-protocols to substituents containing carbon-carbon single, double and triple bonds, carbon nitrogen bonds (anilines and amides) as well as nitriles. These approaches are especially useful for connecting heterocyclic structures to specific positions of the scaffold, e.g. by coupling of tailor-made heterocyclic structures (like boronates or stannanes).

Substituents on the aromatic ring (R7-R10) can often be introduced already in the phenethyl amine precursors (e.g. VII or XII), carrying them unchanged throughout the further synthetic process.

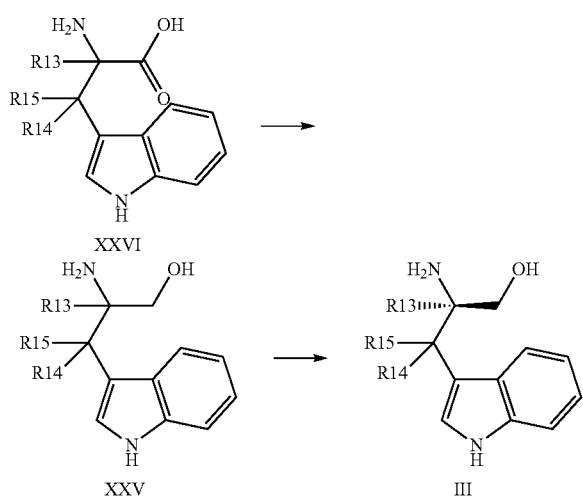

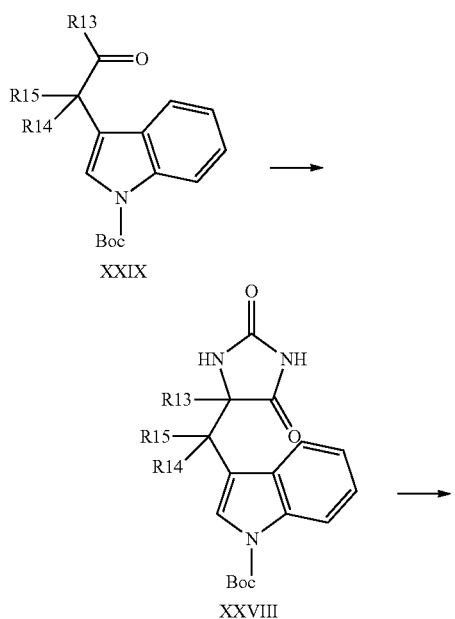

Tryptophanol derivatives of general structure III are either commercially available, or may be prepared in a sequence of reaction steps from commercially available 3-cyanomethyl indole XXXII. Optically pure tryptophanols III may be prepared from their corresponding diastereomeric mixtures XXV using chiral separation technologies such as HPLC with chiral columns, well known to those of skill in the art. The tryptophanols XXV are accessible from their corresponding amino acid precursors XXVI using reducing agents such as borane complexes or LiAlH$_4$. In turn, amino acids XXVI can be obtained from their N-butoxycarbonyl (Boc)-protected precursors XXVII by treatment with strong acids such as trifluoroacetic acid or HCl. The required amino acid framework in XXVII is obtained after basic hydrolysis of hydantoins XXVIII. Typical conditions for this conversion are Ba(OH)$_2$ under elevated pressure and at increased temperature. The hydantoin moiety in XXVIII can be introduced by treating aldehydes or ketones XXIX with ammonium carbonate in the presence of potassium cyanide.

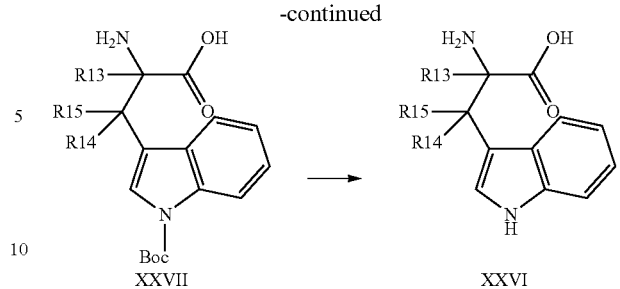

Aldehydes XXIX-a, in which R13=H may be obtained by partial reduction of cyanides XXX using DIBAL-H in toluene at low temperature (−50° C.). Ketones XXIX-b are accessible from aldehydes XXIX-a via a two-step procedure, well know to those skilled in the art. Thus, reaction of XXIX-a with commercially available alkylmagnesium or alkyllithium reagents in the presence of copper salts (or, alternatively, with alkyl cuprates), followed by oxidation of the secondary alcohol moiety (using a variety of oxidation protocols such as Swern-type oxidation or Dess-Martin periodinane), gives access to XXIX-b.

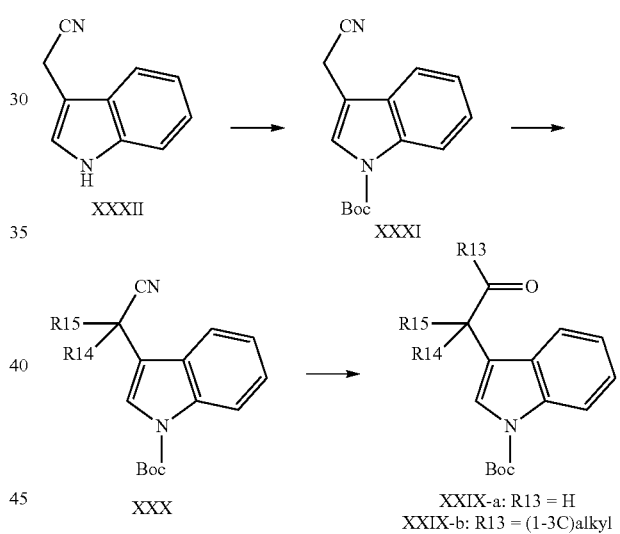

Cyanides XXX, in turn, may be prepared by single or double alkylation of XXXI. In a typical procedure, a strong base such as NaH or LDA is used in an inert solvent such as diethyl ether with alkyl halides as alkyl donors. When alkyl dihalides such as 1,2-dichloroethane or 1,4-dibromobutane are used, R14 and R15 together form a cycloalkyl ring. XXXI is accessible by Boc-protection of XXXII using methods well documented in literature. Typically, tert-butoxycarbonyl anhydride (Boc$_2$O) is used in an appropriate solvent such as dichloromethane in the presence of a suitable base such as triethyl amine (in combination with 4-dimethylamino pyridine DMAP) to functionalize XXXII with a Boc protective group, as described in: *Tetrahedron* 65, 9015-9020 (2009).

The compounds of the invention inhibit FSH receptor activity. All compounds of the invention have a pIC50 of 5 or higher. Preferred are compounds with a pIC50 of more than 7.

LEGENDS TO THE FIGURES

FIG. 1

Estradiol (E2) concentration (in ng/mL) in culture supernatant of human granulosa cells, after 48 h incubation with recFSH or with test compound of example 5 in combination with 250 mU/ml recFSH in culture medium with IBMX, followed by 2 h incubation with 10 μM testosterone in culture medium without IBMX (n=3; mean±s.e.m.).

The invention is illustrated by the following examples.

EXAMPLES

General Comments

The following abbreviations are used in the examples: DCM=dichloromethane, DMF=N,N-dimethylformamide, HCl=hydrogen chloride, NaHCO$_3$=sodium bicarbonate, MgSO$_4$=magnesium sulphate, THF=tetrahydrofuran, Na$_2$SO$_4$=sodium sulphate, DME=dimethoxyethane, LC-MS=liquid chromatography-mass spectrometry, HPLC=high-performance liquid chromatography, MeCN=acetonitrile, Pd/C=palladium on carbon, HATU=2-(1H-7-Azabenzotriazol-1-yl)-1,1,3,3-tetramethyl uronium hexafluorophosphate, DIPEA=N,N-Diisopropylethylamine, DMSO=dimethylsulfoxide, H$_2$=hydrogen, HBr=hydrogen bromide, NH$_4$Cl=ammonium chloride, N$_2$=nitrogen, TBTU=N,N,N',N'-tetramethyl-O-(benzotriazol-1-YL)uronium tetrafluoroborate, KCN=potassium cyanide, (NH$_4$)$_2$CO$_2$, =ammonium bicarbonate, DCE=1,1-dichloroethane, Na$_2$CO$_3$=sodium carbonate, (BOC)$_2$O=Di-tert-butyl dicarbonate.

The names of the final products described in the examples were generated using the convert name to structure tool in ChemDraw version 9.01.

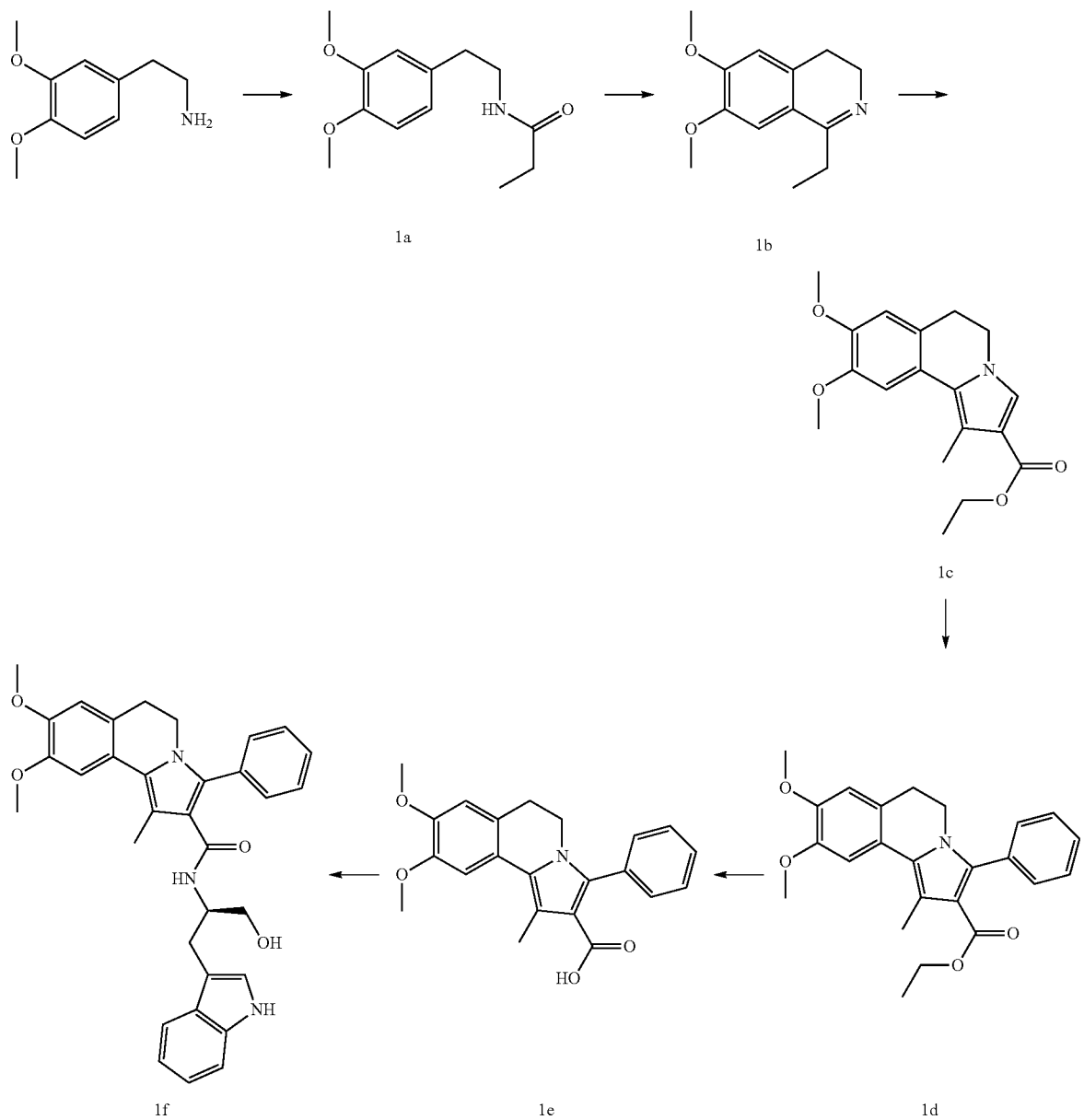

Example 1

(R)—N-(1-hydroxy-3-(1H-indol-3-yl)propan-2-yl)-8,9-dimethoxy-1-methyl-3-phenyl-5,6-dihydropyrrolo[2,1-a]isoquinoline-2-carboxamide

(a). N-(3,4-dimethoxyphenethyl)propionamide

To a solution of 3,4 methoxyphenethylamine (10 g) in DCM (100 ml) were added under a nitrogen atmosphere at 00° C. DIPEA (13.5 ml) and propionylcloride (5.7 ml) dropwise over a period of 10 minutes. The reaction mixture was stirred for 1 hour. The reaction mixture was diluted with DCM and sequentially washed with a aqueous 0.2M HCl solution, a aqueous saturated NaHCO$_3$ solution, water and brine. The organic layer was dried over MgSO$_4$, filtered and the solvents were removed under vacuum.

Yield: 13.03 g

MS (ESI) m/z: 238 (M+H)$^+$.

(b). 1-ethyl-6,7-dimethoxy-3,4-dihydroisoquinoline

To a solution of compound 1a (12 g) in toluene (65 ml) was added dropwise phosphorus oxychloride (12 ml) under nitrogen atmosphere at 95° C., over a period of 1 hour. The mixture was heated at 120° C. for 2 hours and allowed to cool to room temperature overnight. The resulting HCl salt was collected by filtration and washed with diethylether to give the product as a brown solid Yield: 15.48 g

(c). ethyl 8,9-dimethoxy-1-methyl-5,6-dihydropyrrolo[2,1-a]isoquinoline-2-carboxylate To a solution of compound 1b (15.5 g) and potassium carbonate (16.5 g) in acetonitrile (100 ml) was added dropwise ethyl bromopyruvate (7.6 ml). The reaction mixture was heated at 100° C. for 1 hour. The reaction mixture was filtered and concentrated. The residue was dissolved in ethyl acetate, washed with water, dried over MgSO$_4$, filtered and concentrated to a brown solid. The residue was purified by chromatography on silica gel eluting with hexane and increasing amounts of ethyl acetate. The pure fractions were collected and concentrated to a yellow solid.

Yield: 7.51 g

(d). ethyl 8,9-dimethoxy-1-methyl-3-phenyl-5,6-dihydropyrrolo[2,1-a]isoquinoline-2-carboxylate Compound 1c (205 mg), phenylbromide (78 ul), triphenylphospine (34 mg) and cesium carbonate (459 mg) were suspended in degassed dioxane (4 ml). The mixture was further degassed for 10 minutes. Palladium (II) acetate (15 mg) was added and the reaction mixture was degassed for 5 minutes and heated at 100° C. for 18 hours. The reaction was not complete. The reaction was degassed and recharged with triphenylphospine (34 mg, 0.13 mmol) and palladium (II) acetate (15 mg). The reaction mixture was heated for another 18 hours. The reaction mixture was diluted with ethyl acetate and water and filtered through celite. The organic phase was dried (MgSO$_4$), filtered and concentrated to a brown oil. The residue was purified by chromatography on silica gel eluting with hexane and increasing amounts of ethyl acetate. The pure fractions were collected and concentrated to a yellow solid.

Yield: 136 mg

MS (ESI) m/z: 392 (M+H)$^+$.

$^1$H NMR δ (ppm) (CHCl$_3$-d): 7.43-7.38 (3H, m), 7.36-7.32 (2H, m), 7.26 (1H, s, under CHC$_3$ shift), 6.75 (1H, s), 4.06 (2H, 1, J=7.13 Hz), 3.95 (3H, s), 3.90 (3H, s), 3.78 (2H, t, J=6.27 Hz), 2.85 (2H, t, J=628 Hz), 2.67 (3H, s), 1.01 (3H, t, J=7.12 Hz)

(e). 8,9-dimethoxy-1-methyl-3-phenyl-5,6-dihydropyrrolo[2,1-a]isoquinoline-2-carboxylic Acid To a suspension of compound 1d (135 mg) in ethanol (3.5 ml) was added a aqueous solution of 2M sodium hydroxide (1.7 ml). The reaction mixture was heated at 65° C. for 2 nights. The reaction mixture was concentrated and extracted with ethyl acetate and a aqueous 1M HCl solution. The organic phase was dried (MgSO$_4$) and concentrated in vacuo.

Yield: 120 mg (mixture of starting material and product).

(f). (R)—N-(1-hydroxy-3-(1H-indol-3-yl)propan-2-yl)-8,9-dimethoxy-1-methyl-3-phenyl-5,6-dihydropyrrolo[2,1-a]isoquinoline-2-carboxamide 1-Ethyl-3-(3-dimethylaminopropyl) carbodiimide hydrochloride (98 mg), 1-hydroxybenzotriazole (69 mg), DIPEA (0.178 ml) and D-tryptophanol (78 mg) were added to a solution of intermediate 1e (124 mg) in DMF (4 ml). The reaction mixture was stirred for 18 hours at ambient temperature. The reaction mixture was diluted with ethyl acetate and washed sequentially with a aqueous 1M HCl solution, a saturated aqueous NaHCO$_3$ solution and brine. The reaction mixture was dried (MgSO$_4$), filtered and concentrated to a pale brown oil. The residue was purified by chromatography on silica gel eluting with DCM and increasing amounts of diethylether and methanol. The pure fractions were collected and concentrated in vacuo. The residue was purified by preparative HPLC eluting with acetonitrile and water.

Yield: 16.5 mg.

$^1$H NMR δ (ppm) (CHCl$_3$-d): 8.06 (1H, s), 7.55-7.74 (2H, m), 7.42-7.24 (9H, m), 7.17 (1H, t, J=7.59 Hz), 7.08 (1H, t, J=7.5 Hz), 6.78 (1H, d, J=2.32 Hz), 6.74 (1H, s), 5.44 (1H, d, J=7.18 Hz), 4.32-4.23 (1H, m), 3.94 (3H, s), 3.90 (3H, s), 3.844-3.73 (2H, m), 3.55 (1H, d, J=10.60 Hz), 3.45 (1H, s), 2.86 (3H, t, J=6.56 Hz), 2.78-2.55 (5H, m).

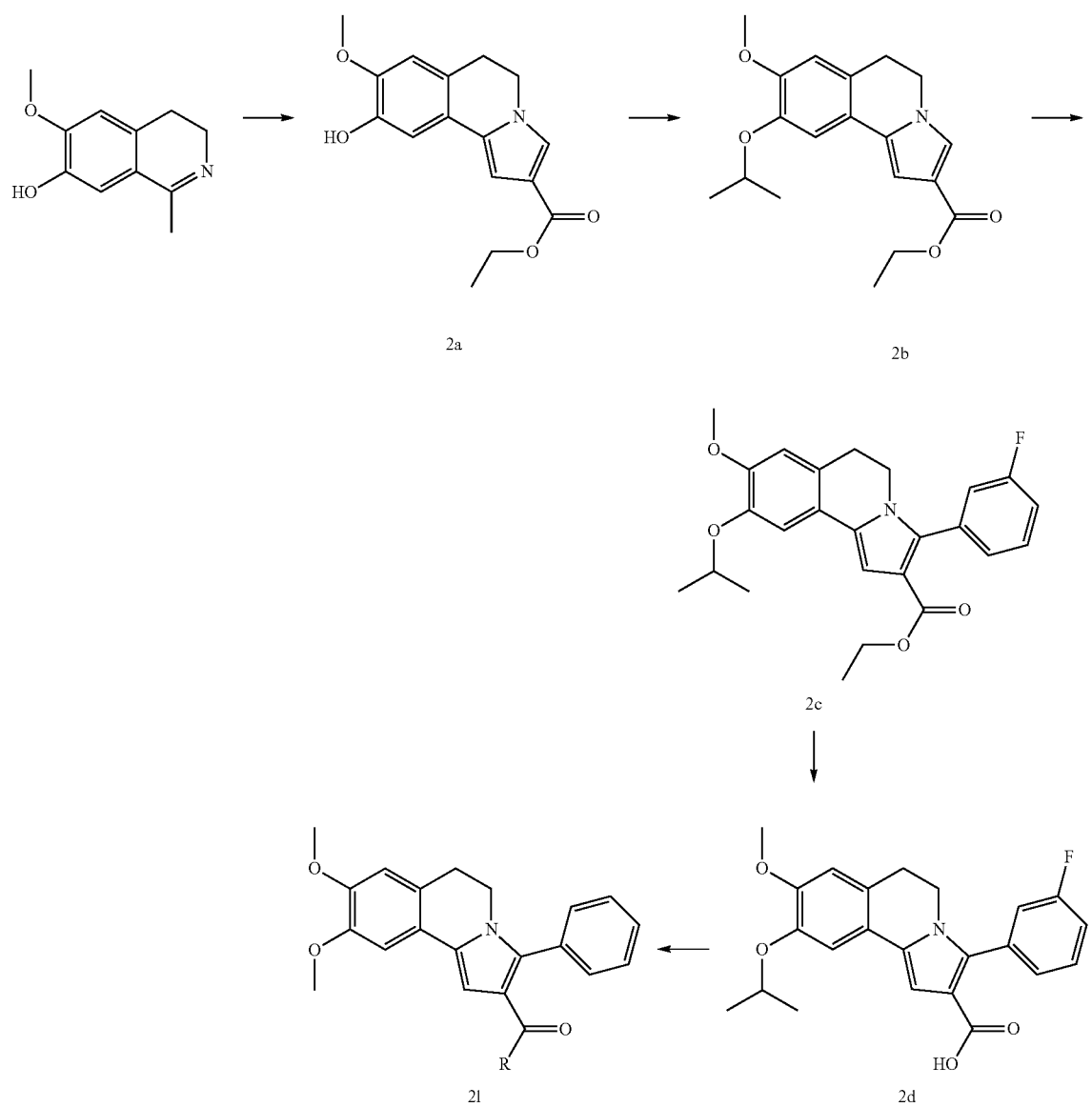
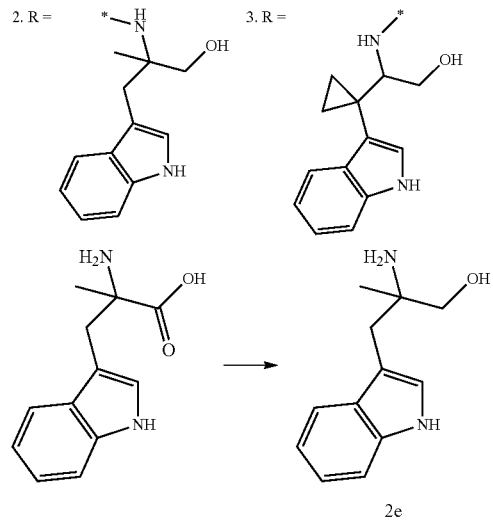

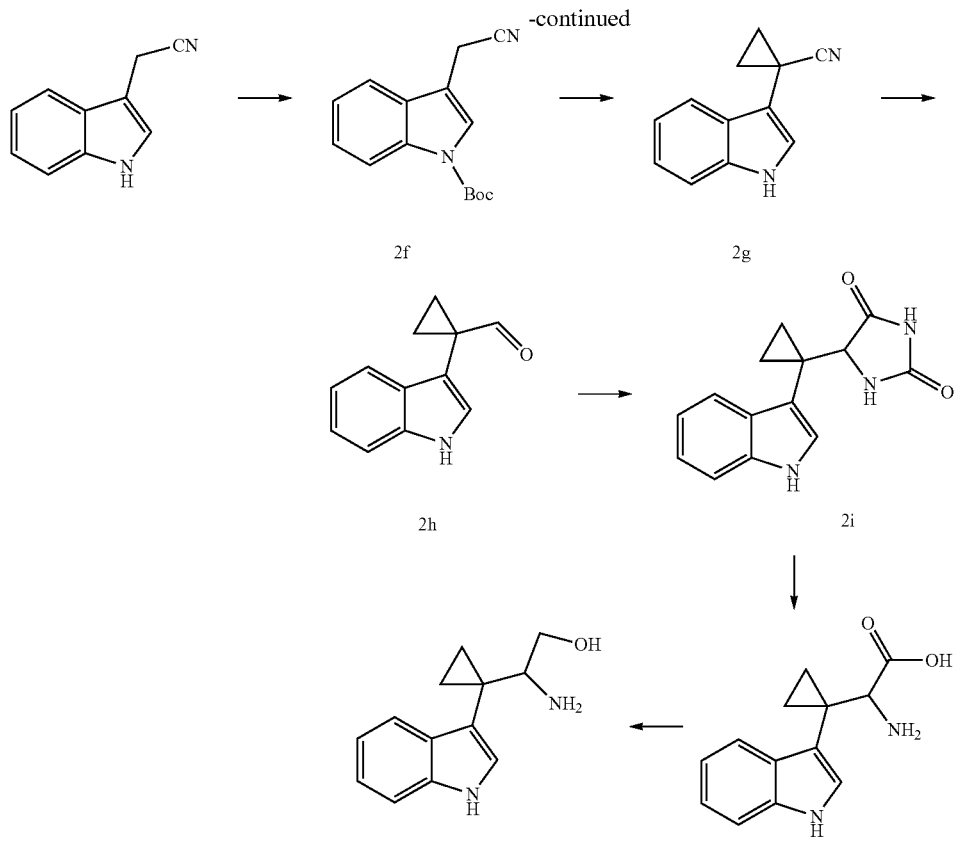

-continued 2f  2g 2h  2i 2k  2j

Example 2

N-(1-hydroxy-3-(1H-indol-3-yl)-2-methylpropan-2-yl)-8,9-dimethoxy-3-phenyl-5,6-dihydropyrrolo[2,1-a]isoquinoline-2-carboxamide (a). ethyl 9-hydroxy-8-methoxy-5,6-dihydropyrrolo[2,1-a]isoquinoline-2-carboxylate To a solution of 1-methyl-7-hydroxy-6-methoxy-3,4-dihydroisoquinoline (100 mg) in EtOH (5 ml) was added dropwise under a nitrogen atmosphere ethylbromopyruvate (0.065 ml) and the reaction mixture was heated under reflux for 2 hours. The reaction mixture was allowed to cool to ambient temperature, quenched with a saturated aqueous $NaHCO_3$ solution and extracted with ethyl acetate. The organic layer was dried ($MgSO_4$), filtered and concentrated in vacuo. The residue was purified by chromatography on silica gel eluting with heptane and increasing amounts of ethyl acetate.

Yield: 82 mg (b). ethyl 9-isopropoxy-8-methoxy-5,6-dihydropyrrolo[2,1-a]isoquinoline-2-carboxylate To a solution of compound 2a (561 mg) in DMF (10 ml) were added potassium carbonate (810 mg) followed by 2-bromopropane (0.36 ml). The reaction mixture was stirred at 65° C. overnight. The reaction mixture was allowed to cool to ambient temperature, quenched with a saturated aqueous $NaHCO_3$ solution and extracted with ethyl acetate. The organic layer was dried ($MgSO_4$) and concentrated in vacuo. The residue was purified by chromatography on silica gel eluting with heptane and increasing amounts of ethyl acetate.

Yield: 445 mg

MS (ESI) m/z: 330 (M+H)$^+$.

(c). ethyl 3-(3-fluorophenyl)-9-isopropoxy-8-methoxy-5,6-dihydropyrolo[2,1-a]isoquinoline-2-carboxylate Four identical solutions of intermediate 2b (1.0 g), 3-fluoroiodobenzene (423 μl), triphenylphosphine (157 mg) and cesium carbonate (1.95 g) in dioxane (20 ml) were degassed by bubbling through a gentle stream of nitrogen for 30 minutes. Palladium acetate (67 mg) was added to each reaction tube and the mixtures were degassed for a further 15 minutes before being sealed under nitrogen and heated to 110° C. for 6 hours. LC-MS indicated the reaction was approximately 50% complete, hence the mixtures were degassed with nitrogen for 20 minutes and a further aliquot of the 3-fluoroiodobenzene (211 μl), palladium acetate (34 mg) and triphenylphospine (79 mg) were added to each. The mixtures were degassed for a further 15 minutes before being sealed under nitrogen and heated for 16 hours at 110° C. LC-MS indicated the reactions were all approximately 65% complete hence they were combined and filtered through a pad of celite and washed with dioxane and ethyl acetate. Ethyl acetate was added to the solution and washed with water (3×). The organic layer was passed through a hydrophobic frit and the solvent removed under vacuum.

The residue was purified by chromatography on silica gel eluting with petrol and increasing amounts of ethyl acetate. The target fractions were combined and dried under vacuum to give a solid that was triturated with diethyl ether to give the product, as an off-white solid Yield: 3.34 g MS (ESI) m/z: 424 (M+H)+.

$^1$H NMR δ (ppm) (CHCl$_3$-d): 7.44-7.37 (1H, m), 7.18 (1H, dd, J=7.7, 1.0 Hz), 7.14-7.08 (3H, m), 6.90 (1H, s), 6.71 (1H, s), 4.62-4.54 (1H, m), 4.16 (2H, q, J=7.1 Hz), 3.89-3.83 (5H, m), 2.93 (2H, t, J=6.5 Hz), 1.41 (6H, d, J=6.1 Hz), 1.18 (3H, t, J=7.1 Hz).

(d). 3-(3-fluorophenyl)-9-isopropoxy-8-methoxy-5,6-dihydropyrrolo[2,1-a]isoquinoline-2-carboxylic Acid To a solution of compound 2c (0.5 g) in ethanol (12 ml) was added a 2M aqueous sodium hydroxide solution (6 ml). The reaction mixture was heated to 70° C. and stirred for 18 hours. The solvents were removed under vacuum. The solid was suspended in ethyl acetate and acidified with a aqueous 2M HCl solution to pH 1. The phases were separated and the aqueous phase was re-extracted with ethyl acetate twice. The combined organic layers were washed with water and brine, before drying over MgSO$_4$. The solvents were removed under vacuum to yield a pale brown solid.

Yield: 0.45 g (e). 2-amino-3-(1H-indol-3-yl)-2-methylpropan-1-ol

To a solution of alpha-methyl-DL-tryptophan (100 mg) in dry THF (10 ml) was added a borane-tetrahydrofuran complex (1.14 ml) dropwise. The reaction mixture was heated at 65° C. for 4.5 hours. The reaction mixture was quenched with ethanol (3 ml). The reaction mixture was concentrated and extracted with ethyl acetate and water. The organic layer was dried (MgSO$_4$), filtered and concentrated in vacuo. The residue was purified by preparative HPLC eluting with acetonitrile and water. The pure fractions were collected and freeze dried.

Yield: 33.7 mg (f). tert-butyl 3-(cyanomethyl)-1H-indole-1-carboxylate 3-indoleacetonitrile (50 g), di-tert-butyl dicarbonate (76.8 g) and 4-dimethylaminopyridine (1.96 g) were added to DCM (200 ml). The mixture was stirred at room temperature overnight. The solution was washed with brine and water and then dried (Na$_2$SO$_4$). The organic layer was concentrated and the residue was purified by chromatography on silica gel eluting with heptane and increasing amounts of ethyl acetate.

Yield: 68 g (g). 1-(1H-indol-3-yl)cyclopropanecarbonitrile

Sodium hydride (4 equiv) was suspended in DMSO (~6 ml/g). The mixture was heated to 70-75° C. for 30 minutes. The mixture was allowed to cool to room temperature before adding it in portions to a cooled suspension of compound 1f (1 equiv) and dibromo alkane (1 equiv) in diethylether (2.5× volume of DMSO) at 0° C. If the temperature rises above 5° C. a by-product is formed. The mixture was allowed to warm to room temperature and was stirred overnight to complete cyclisation. The suspension was diluted with water and acidified with a aqueous 2N HCl solution. The mixture was extracted with ethyl acetate twice and the organic layers were dried (Na$_2$SO$_4$). The organic layer was concentrated before dissolving in dioxane. To the solution 4N HCl in dioxane was added (5 equiv) and was stirred overnight at room temperature. The crude mixture was diluted with water and basified with a aqueous 2N sodium hydroxide solution. The aqueous layer was extracted with ethyl acetate (2×), dried (Na$_2$SO$_4$) and filtered. The organic layers were concentrated and the crude residue was used as such in the next step.

(h). 1-(1H-indol-3-yl)cyclopropanecarbaldehyde

Compound 2g crude was dissolved in toluene. The solution was cooled to −45° C. and DIBAL-H (1.5-2.0 equiv) was added dropwise. The mixture was allowed to warm to 0° C. and this was stirred for 1 hour at 0° C. The mixture was quenched with a mixture of diethylether and a saturated aqueous NH$_4$Cl solution (1:1) and subsequently with a aqueous 1.6 N HCl solution (in 1:1 or 1:1.5 ratio to the Ether mixture). A thick suspension was formed and the suspension was vigorously stirred at room temperature overnight. The mixture was diluted with water and basified with a aqueous 2N sodium hydroxide solution. The aqueous layer was extracted with ethyl acetate and the organic layer was dried (Na$_2$SO$_4$) and filtered. The organic layer was concentrated and used as such in the next step.

(i). 5-(1-(1H-indol-3-yl)cyclopropyl)imidazolidine-2,4-dione

Compound 2h (1 equiv) was suspended in ethanol/water (1:1). To the solution KCN (1.5 equiv) and (NH$_4$)$_2$CO$_2$ (3.0 equiv) were added and the mixture was poured into a pressure tube. The mixture was heated to 80° C. in an oil bath for 6 hours. The mixture was allowed to cool to room temperature overnight. The mixture was diluted with water and acidified with a aqueous 2N HCl solution. The aqueous layer was extracted with ethyl acetate and diethylether. The organic layers were dried (Na$_2$SO$_4$), filtered and concentrated. The residue was purified by chromatography on silica gel eluting with heptane and increasing amounts of ethyl acetate. The product sticks on the column so rinsing with ethyl acetate or methanol was needed.

Yield: 3 g (j). 2-(1-(1H-indol-3-yl)cyclopropyl)-2-aminoacetic Acid

Compound 2j (1 equiv) and barium hydroxide (4 equiv) were suspended in water/dioxane (1:1) and poured into a microwave tube. The mixture was heated to 170° C. (external temperature of heating mantel) for minimum of 2 days. The mixture was filtrated and washed with water. The layers were separated and the aqueous layer was concentrated. The solid was washed with DCM and dried under vacuum (50° C.).

crude 1.55 g (k). 2-(1-(1H-indol-3-yl)cyclopropyl)-2-aminoethanol

Compound 2j (1 eq.) was dissolved in THF and cooled to 0° C. To the solution a suspension of lithium aluminium hydride (6 equiv) in THF was added in portions. The mixture was allowed to warm to room temperature and stirred for 30 minutes before heating it to reflux for 6 hours. The mixture was stirred overnight at room temperature. This was cooled to 0° C. and subsequently water and a aqueous 2N sodium hydroxide solution were added (1:2:1 ratio). The mixture was stirred for 30 min. allowing it to rise to room temperature. The mixture was filtered over celite and rinsed with diethylether. The mixture was dried (Na₂SO₄), filtered and concentrated in vacuo.

Yield: 365 mg (l). N-(1-hydroxy-3-(1H-indol-3-yl)-2-methylpropan-2-yl)-8,9-dimethoxy-3-phenyl-5,6-dihydropyrrolo[2,1-a]isoquinoline-2-carboxamide 1-Ethyl-3-(3-dimethylaminopropyl) carbodiimide hydrochloride (58.2 mg), 1-hydroxybenzotriazole (28.7 mg), triethylamine (0.084 ml) and 2e (762 mg) were added to a solution of intermediate 2d (124 mg) in DMF (4 ml). The reaction mixture was stirred for 18 hours at ambient temperature. The reaction mixture was diluted with ethyl acetate and washed sequentially with a aqueous 1M HCl solution, a saturated aqueous NaHCO₃ solution and brine. The reaction mixture was dried (MgSO₄), filtered and concentrated to a pale brown oil. The residue was purified by preparative HPLC eluting with acetonitrile and water.

Yield: 74 mg.

¹H NMR δ (ppm) (CHCl₃-d): 8.10 (1H, s), 7.77 (1H, d, J=8.19 Hz), 7.39 (1H, d, J=8.13 Hz), 7.29-7.16 (6H, m), 7.13-6.92 (5H, m), 6.80 (1H, d, J=2.48 Hz), 6.72 (2H, d, J=12.30 Hz), 5.63 (1H, d, J=9.32 Hz), 4.61-4.54 (1H, m), 4.40 (1H, td, J=8.65, 3.51 Hz), 3.87-3.72 (5H, m), 3.25 (1H, t, J=9.55 Hz), 2.92 (2H, t, J=6.54 Hz), 2.43-2.25 (2H, m), 1.64 (1H, t, J=12.86), 1.55 (7H, s), 1.46-1.35 (7H, m), 1.37-1.22 (3H, m)

Example 3

N-(1-(1-(1H-indol-3-yl)cyclopropyl)-2-hydroxyethyl)-8,9-dimethoxy-3-phenyl-5,6-dihydropyrrolo[2,1-a]isoquinoline-2-carboxamide Compound 3 was prepared in an analogous fashion as described for example 2, with compound 2k as reagent.

Yield: 27.6 mg.

¹H NMR δ (ppm) (CHCl₃-d): 8.00 (1H, s), 7.71 (1H, d, J=7.91 Hz), 7.37 (1H, d, J=8.09 Hz), 7.29-7.16 (5H, m), 7.16-6.98 (5H, m), 6.77 (1H, d, J=2.44 Hz), 6.71 (2H, d, J=3.87 Hz), 5.91 (1H, d, J=8.00 Hz), 4.61-4.54 (1H, m), 3.92-3.77 (5H, m), 3.72 (1H, td, J=7.87, 3.96), 3.54-3.47 (1H, m), 2.92 (2H, t, J=6.51 Hz), 2.67-2.61 (1H, m), 1.42 (6H, dd, J=8.67, 6.07), 0.95-0.89 (2H, m), 0.85 (1H, dd, J=9.10, 2.61 Hz), 0.73 (1H, dd, J=8.99, 2.77 Hz)

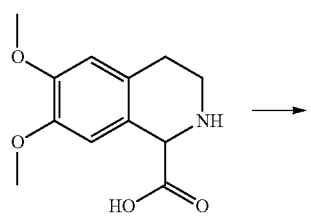

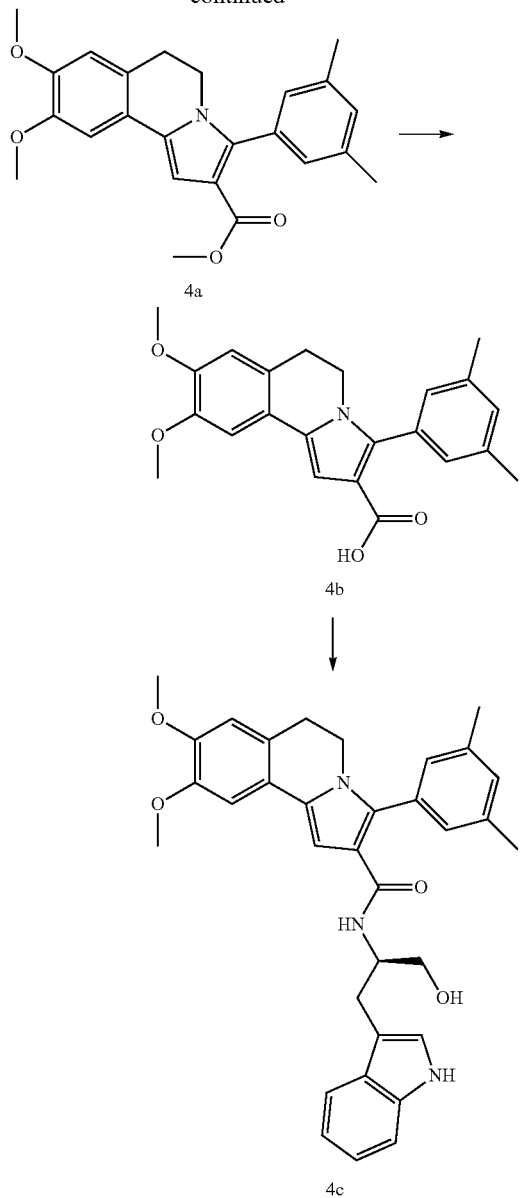

Example 4

(R)-3-(3,5-dimethylphenyl)-N-(1-hydroxy-3-(1H-indol-3-yl)propan-2-yl)-8,9-dimethoxy-5,6-dihydropyrrolo[2,1-a]isoquinoline-2-carboxamide (a). methyl 3-(3,5-dimethylphenyl)-8,9-dimethoxy-5,6-dihydropyrrolo[2,1-a]isoquinoline-2-carboxylate A mixture of 6,7-dimethoxy-1,2,3,4-tetrahydro-isoquinoline-1-carboxylic acid (3.52) and 3,5-dimethylbenzoylchloride (3.25 g) in THF (3 ml) with molecular sieves was heated in the microwave for 5 minutes at 150° C. The molecular sieves were filtered and acetic anhydride (4.55 g) and methylpropiolate (1.38 g) were added. The mixture was stirred in the microwave for 5 minutes at 150° C. The reaction mixture was diluted with ethyl acetate and extracted sequentially with a aqueous 1M HCl solution, water and brine. The organic layer was dried (Na₂SO₄), filtered and concentrated in vacuo. The residue was purified by chromatography on silica gel eluting with heptane and increasing amounts of ethyl acetate.

Yield: 1.7 g mixture of regioisomers 2:8
MS (ESI) m/z: 392 (M+H)⁺.

(b). 3-(3,5-dimethylphenyl)-8,9-dimethoxy-5,6-dihydropyrrolo[2,1-a]isoquinoline-2-carboxylic Acid A suspension of compound 4a (1.2 g) in a aqueous 3M lithium hydroxide solution (3 ml) and dioxane (1 ml) was heated for 5 minutes in the microwave at 180° C. The reaction mixture was acidified with a aqueous 2N HCl solution to pH=2 and the precipitate was filtered.

ethyl acetate. The aqueous phase was extracted with ethyl acetate and the combined organic layers were washed with water (twice) and brine, dried (MgSO₄), filtered and concentrated in vacuo. The residue was purified by chromatography on silica gel eluting with heptane and increasing amounts of ethyl acetate. The pure fractions were collected and concentrated in vacuo. The residue was purified by preparative HPLC eluting with acetonitrile and water. The pure fractions were freeze dried.

Yield: 99.2 mg
MS (ESI) m/z: 550 (M+H)⁺.

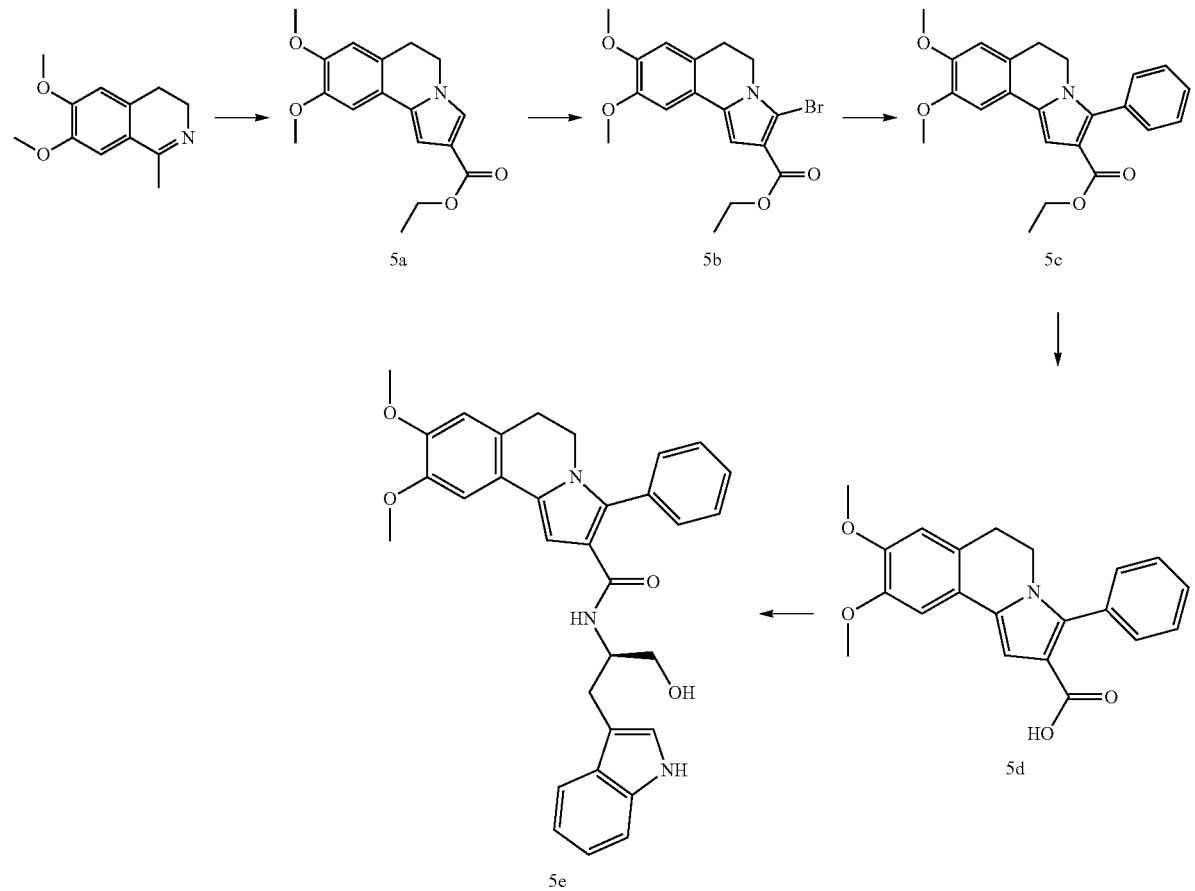

Yield: 1.0 g mixture of regioisomers 2:8
MS (ESI) m/z: 378 (M+H)⁺.

(c). (R)-3-(3,5-dimethylphenyl)-N-(1-hydroxy-3-(1H-indol-3-yl)propan-2-yl)-8,9-dimethoxy-5,6-dihydropyrrolo[2,1-a]isoquinoline-2-carboxamide 1-Ethyl-3-(3-dimethylaminopropyl) carbodiimide hydrochloride (360 mg), 1-hydroxybenzotriazole (127 mg), DIPEA (0.46 ml) and D-tryptophanol (357 mg) were added to a solution of intermediate 4b (254 mg) in DMF (15 ml). The reaction mixture was stirred for 18 hours at ambient temperature. The reaction mixture was quenched with a saturated aqueous NaHCO₃ solution and extracted with Example 5

(R)—N-(1-hydroxy-3-(1H-indol-3-yl)propan-2-yl)-8,9-dimethoxy-3-phenyl-5,6-dihydropyrrolo[2,1-a]isoquinoline-2-carboxamide (a). ethyl 8,9-dimethoxy-5,6-dihydropyrrolo[2,1-a]isoquinoline-2-carboxylate To a mixture of 1-methyl-6,7-dimethoxy-3,4-dihydroisoquinoline (2 g) and potassium carbonate (2.4 g) in ethanol (50 ml) was added dropwise ethylbromopyruvate (1.22 ml). The reaction mixture was refluxed for 3 hrs. The reaction was allowed to cool to ambient temperature before a saturated aqueous NaHCO$_3$ solution was added. The aqueous phase was extracted with ethyl acetate twice. The combined organic layers were washed with brine. The organic layer was dried (MgSO$_4$), filtered and concentrated in vacuo. The residue was purified by chromatography on silica gel eluting with heptane and increasing amounts of ethyl acetate.

Yield: 2.1 g
MS (ESI) m/z: 302 (M+H)$^+$.

(b). ethyl 3-bromo-8,9-dimethoxy-5,6-dihydropyrrolo[2,1-a]isoquinoline-2-carboxylate A solution of N-bromosuccinimide (0.91 g) in DCM (50 ml) was added dropwise over a period of 45 minutes to a solution of intermediate 5a (1.88 g) in DCM (50 ml). The reaction mixture was stirred for 2 hours before quenching with a saturated aqueous NaHCO$_3$ solution. The aqueous phase was extracted with DCM twice and the combined organics layers were washed with water and brine, dried (MgSO$_4$) and filtered. The solvents were removed under vacuum to yield a crude solid that was purified by chromatography on silica gel eluting with petrol and increasing amounts of ethyl acetate to give the product, as an off white solid Yield: 1.36 g
$^1$H NMR δ (ppm) (CHCl$_3$-d): 7.06 (1H, s), 6.86 (1H, s), 6.71 (1H, s), 4.60-4.50 (1H, m), 4.33 (2H, q, J=7.12 Hz), 4.16-4.07 (2H, m), 3.87 (3H, s), 3.01 (2H, t, J=6.64 Hz), 1.41-1.36 (9H, m)

(c). ethyl 8,9-dimethoxy-3-phenyl-5,6-dihydropyrrolo[2,1-a]isoquinoline-2-carboxylate Tetrakis(triphenylphosphine)palladium(0) (975 mg) was added to a degassed solution of intermediate 5b (60 mg), phenylboronic acid (625 mg) and potassium carbonate (1.063 g) in a 10:1 mixture of DME:water (30 ml). The mixture was degassed by gently bubbling through nitrogen for a further 5 minutes before sealing under nitrogen and then heating to 90° C. for 3 hours. The reaction was allowed to cool to ambient temperature before a saturated aqueous NaHCO$_3$ solution was added. The aqueous phase was extracted with ethyl acetate twice. The combined organic layers were washed with brine. The organic layer was dried (MgSO$_4$), filtered and concentrated in vacuo. The residue was purified by chromatography on silica gel eluting with heptane and increasing amounts of ethyl acetate.

Yield: 990 mg
MS (ESI) m/z: 378 (M+H)$^+$.

(d). 8,9-dimethoxy-3-phenyl-5,6-dihydropyrrolo[2,1-a]isoquinoline-2-carboxylic Acid A aqueous 2M sodium hydroxide solution (2 ml) was added to a solution of intermediate 5c (129 mg) in ethanol (5 ml). The mixture was heated to 60° C. for 6 hours. The reaction was allowed to cool to ambient temperature before a aqueous 2M HCl solution (3.1 ml) was added. The mixture was extracted with ethyl acetate and water. The organic layer was washed with brine. The organic layer was dried (MgSO$_4$), filtered and concentrated in vacuo.

Yield: 116 mg
MS (ESI) m/z: 350 (M+H)$^+$.

(e). (R)—N-(1-hydroxy-3-(1H-indol-3-yl)propan-2-yl)-8,9-dimethoxy-3-phenyl-5,6-dihydropyrrolo[2,1-a]isoquinoline-2-carboxamide 1-Ethyl-3-(3-dimethylaminopropyl) carbodiimide hydrochloride (226 mg), 1-hydroxybenzotriazole (160 mg), DIPEA (0.39 ml) and D-tryptophanol (299 mg) were added to a solution of intermediate 5d (275 mg) in DMF (15 ml). The reaction mixture was stirred for 18 hours at ambient temperature. The reaction mixture was quenched with a saturated aqueous NaHCO$_3$ solution and extracted with ethyl acetate. The aqueous phase was extracted with ethyl acetate and the combined organic layers were washed with water twice and brine. The organic layer was dried (MgSO$_4$), filtered and concentrated in vacuo. The residue was purified by chromatography on silica gel eluting with heptane and increasing amounts of ethyl acetate.

Yield: 293.6 mg
MS (ESI) m/z: 522 (M+H)$^+$.

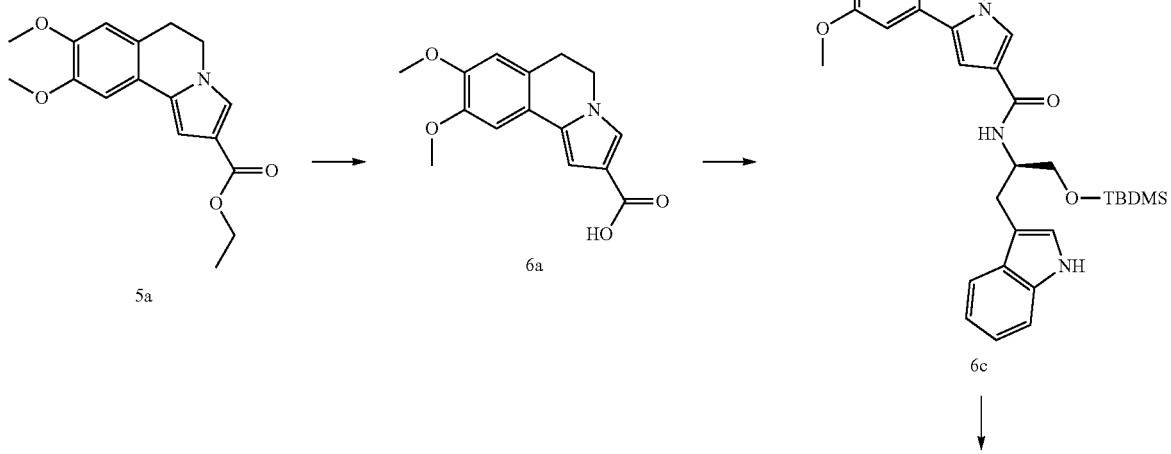

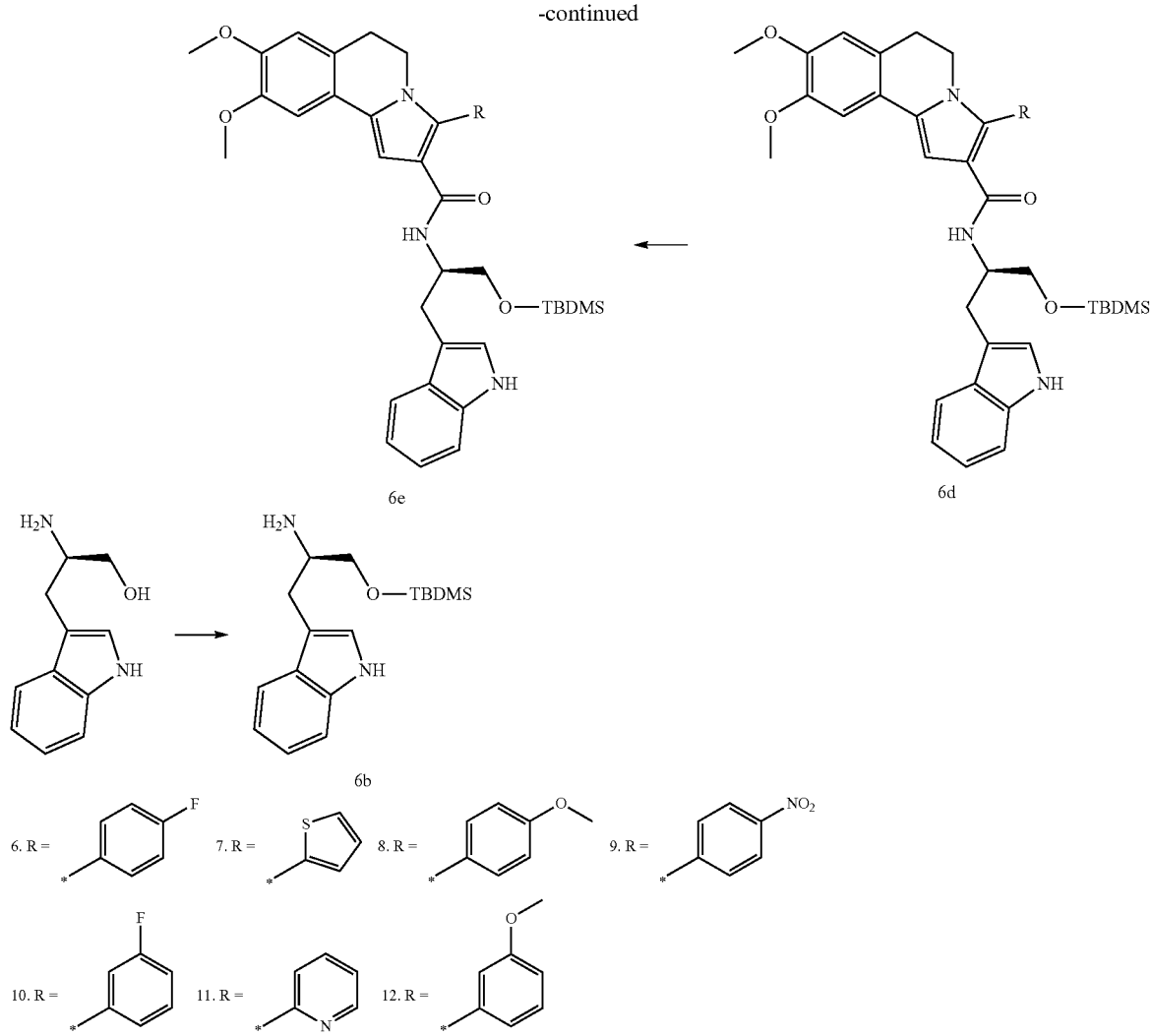

Example 6

(R)—N-(1-hydroxy-3-(1H-indol-3-yl)propan-2-yl)-8,9-dimethoxy-3-(4-fluorophenyl)-5,6-dihydropyrrolo[2,1-a]isoquinoline-2-carboxamide

(a). 8,9-dimethoxy-5,6-dihydropyrrolo[2,1-a]isoquinoline-2-carboxylic Acid

A aqueous 2M sodium hydroxide (50 ml) was added to a solution of intermediate 5a (3.01 g) in ethanol (100 ml). The mixture was heated to 65° C. for 18 hours. The solvents were removed under vacuum and the crude residue was suspended in ethyl acetate before acidifying to pH 2 with a aqueous 2M HCl solution. A white precipitate was removed by filtration and dried under vacuum (908 mg). The aqueous phase was re-extracted with ethyl acetate. The combined organic layers were washed with water (25 ml), dried (MgSO$_4$) and filtered. The solvents were removed under vacuum to give a grey solid. The two solids were combined to give the product, as an off white solid that was used without further purification.

Yield: 2.3 g

(b). (R)-1-(tert-butyldimethylsilyloxy)-3-(1H-indol-3-yl)propan-2-amine

To a solution of D-Tryptophanol (1.024 g) and imidazole (403 mg) in DCM (40 ml) and THF (8 ml) was added a solution of tert-butyldimethylsilyl chloride (0.852 g) in DCM (5 ml) dropwise. The reaction was allowed to warm to room temperature overnight. The reaction mixture was quenched with a saturated aqueous NaHCO$_3$ solution and the reaction mixture was extracted with dichloromethane. The aqueous phase was washed with dichloromethane and the combined organic layers were washed with brine, dried (MgSO$_4$), filtered and concentrated in vacuo. The residue was purified by chromatography on silica gel eluting with heptane and increasing amounts of ethyl acetate.

Yield: 1.11 g.

MS (ESI) m/z: 305 (M+H)$^+$.

(c). (R)—N-(1-(tert-butyldimethylsilyloxy)-3-(1H-indol-3-yl)propan-2-yl)-8,9-dimethoxy-5,6-dihydropyrrolo[2,1-a]isoquinoline-2-carboxamide Compound 6b (2.34 g) was added to a solution of intermediate 6a (1.91 g) in DMF (75 ml). 1-Hydroxybenzotriazole (1.42 g), 1-ethyl-3-(3-dimethylaminopropyl) carbodiimide hydrochloride (2.01 g) and diisopropylethylamine (3.66 ml) were added to the reaction mixture and the reaction mixture was stirred at ambient temperature for 72 hours. The reaction mixture was dissolved in ethyl acetate and washed with water (3×). A precipitate was removed by filtration and determined to be pure product by HPLC (1.90 g). The aqueous phase was re-extracted with ethyl acetate (3×) and the combined organic layers were washed with water and a saturated aqueous $NaHCO_3$ solution, dried ($MgSO_4$) and filtered. The solvents were removed under vacuum to give a pale brown solid. The two collected solids were combined to give the product as a pale brown solid which was used without further purification.

Yield: 3.56 g

Reaction Conditions d and e were Carried Out in Sequence without Isolation of Intermediate D.

(d/e). (R)—N-(1-hydroxy-3-(1H-indol-3-yl)propan-2-yl)-8,9-dimethoxy-3-(4-fluorophenyl)-5,6-dihydropyrrolo[2,1-a]isoquinoline-2-carboxamide Palladium (II) acetate (4.5 mg) was added to a degassed solution of intermediate 6c (112 mg), 4-fluorobenzene (53 mg), cesium carbonate (141 mg) and triphenylphosphine (11 mg) in dioxane (3 ml) and the mixture was degassed with nitrogen for a further 15 minutes. The reaction tube was sealed and then heated to 100° C. for 18 hours. The reaction was determined to be incomplete, hence a further aliquot of palladium (II) acetate (4.5 mg), triphenylphosphine (11 mg) and 4-fluorobenzene (53 mg) was added. The mixture was degassed with nitrogen for 15 minutes, sealed under nitrogen and then heated to 100° C. for 18 hours. The reaction was determined to be approximately 50% complete by HPLC hence the solvents were removed under vacuum and the residue obtained was partitioned between ethyl acetate (5 ml) and water. The aqueous phase was re-extracted with ethyl acetate and the combined organic layers were washed with water and then concentrated to dryness giving a dark brown oil. The oil was redissolved in THF (1 ml) before the addition of tetrabutylammonium fluoride in THF (0.3 ml, 1 N), stirring for 2 hours. The solvents were removed under vacuum to give a dark oil that was purified by preparative HPLC eluting with acetonitrile and water to give the product, as an off white solid Yield: 22 mg MS (ESI) m/z: 540 (M+H)$^+$.

$^1$H NMR δ (ppm) (CHCl$_3$-d): 8.10 (1H, s), 7.57 (1H, d, J=7.87 Hz), 7.37 (1H, d, J=8.09 Hz), 7.03 (1H, s), 6.97-6.88 (3H, m), 6.76 (1H, s), 6.68 (1H, s), 5.66 (1H, d, J=7.08 Hz), 4.37-4.30 (1H, m), 3.93 (2H, s), 3.88 (2H, s), 3.75-3.62 (3H, m), 3.58 (1H, dd, J=10.91, 5.91 Hz), 3.07 (1H, s), 2.96-2.81 (4H, m).

Example 7

(R)—N-(1-hydroxy-3-(1H-indol-3-yl)propan-2-yl)-8,9-dimethoxy-3-(thiophen-2-yl)-5,6-dihydropyrrolo[2,1-a]isoquinoline-2-carboxamide Compound 7 was prepared in an analogous fashion as described for example 6.

MS (ESI) m/z: 528 (M+H)$^+$.

$^1$H NMR δ (ppm) (CHCl$_3$-d): 8.00 (1H, s), 7.57 (1H, d, J=7.9 Hz), 7.39-7.35 (2H, m), 7.19 (1H, t, J=3.9 Hz), 7.12 (1H, t, J=7.5 Hz), 7.07 (1H, s), 6.96-6.90 (4H, m), 6.68 (1H, s), 5.86 (1H, d, J=6.9 Hz), 4.37-4.31 (1H, m), 3.93 (3H, s), 3.89 (3H, s), 3.81 (2H, t, J=6.6 Hz), 3.68 (1H, d, J=11.4 Hz), 3.57 (1H, dd, J=11.0, 5.9 Hz), 3.05 (1H, s), 2.92 (2H, t, J=6.7 Hz), 2.89-2.77 (2H, m).

Example 8

(R)—N-(1-hydroxy-3-(1H-indol-3-yl)propan-2-yl)-8,9-dimethoxy-3-(4-methoxyphenyl)-5,6-dihydropyrrolo[2,1-a]isoquinoline-2-carboxamide Compound 8 was prepared in an analogous fashion as described for example 6.

MS (ESI) m/z: 552 (M+H)$^+$.

$^1$H NMR δ (ppm) (CHCl$_3$-d): 8.09 (1H, s), 7.54 (1H, d, J=7.89 Hz), 7.33 (1H, d, J=8.08 Hz), 6.93-6.82 (4H, m), 6.78 (1H, d, J=2.24 Hz), 6.68 (1H, s), 5.73 (1H, d, J=6.81 Hz), 4.34-4.26 (1H, m), 3.90 (6H, d, J=16.25 Hz), 3.86-3.68 (4H, m), 3.72-3.61 (1H, m), 3.54 (1H, t, J=7.52 Hz), 3.24 (1H, s), 2.93-2.69 (4H, m), Example 9

(R)—N-(1-hydroxy-3-(1H-indol-3-yl)propan-2-yl)-8,9-dimethoxy-3-(4-nitrophenyl)-5,6-dihydropyrrolo[2,1-a]isoquinoline-2-carboxamide Compound 9 was prepared in an analogous fashion as described for example 6.

$^1$H NMR δ (ppm) (CHCl$_3$-d): 8.13 (1H, s), 8.11 (1H, s), 7.60 (1H, d, J=7.86 Hz), 7.43 (2H, d, J=8.56 Hz), 7.39 (1H, d, J=8.17), 7.26-7.19 (1H, m), 7.15 (1H, d, J=7.56 Hz), 7.02-6.98 (2H, m), 6.70 (1H, s), 6.56 (1H, s), 5.84 (1H, d, J=7.24 Hz), 4.45-4.35 (1H, m), 3.97-3.93 (3H, m), 3.90-3.87 (3H, m), 3.84-3.79 (2H, m), 3.73-3.66 (2H, m), 3.02 (2H, dd, J=6.47, 3.36 Hz), 2.93 (2H, t, J=6.57 Hz), 2.78 (1H, s).

Example 10

(R)-3-(3-fluorophenyl)-N-(1-hydroxy-3-(1H-indol-3-yl)propan-2-yl)-8,9-dimethoxy-5,6-dihydropyrrolo[2,1-a]isoquinoline-2-carboxamide Compound 10 was prepared in an analogous fashion as described for example 6.

MS (ESI) m/z: 540 (M+H)$^+$.

$^1$H NMR δ (ppm) (CHCl$_3$-d): 8.15 (1H, s), 7.57 (1H, d, J=7.89 Hz), 7.35 (1H, d, J=8.09 Hz), 6.87 (1H, s), 6.75 (1H, s), 6.68 (1H, s), 5.72 (1H, d, J=6.98 Hz), 4.36-4.29 (1H, m), 3.90 (6H, d, J=17.08 Hz), 3.77 (2H, t, J=6.54 Hz), 3.69-3.54 (2H, m), 3.14 (1H, s), 2.96-2.80 (4H, m).

Example 11

(R)—N-(1-hydroxy-3-(1H-indol-3-yl)propan-2-yl)-8-methoxy-9-(methylamino)-3-(pyridin-2-yl)-5,6-dihydropyrrolo[2,1-a]isoquinoline-2-carboxamide Compound 11 was prepared in an analogous fashion as described for example 6.

MS (ESI) m/z: 523 (M+H)$^+$.

$^1$H NMR δ (ppm) (CHCl$_3$-d): 8.42-8.31 (2H, m), 8.12 (1H, s), 7.67-7.58 (2H, m), 7.18-7.02 (4H, m), 6.92-6.85 (2H, m), 6.69 (1H, s), 4.39-4.33 (1H, m), 4.02 (2H, t, J=6.49 Hz), 3.91 (6H, d, J=14.15 Hz), 3.77 (1H, dd, J=11.01, 3.36 Hz), 3.71-3.62 (1H, m), 3.01-2.88 (4H, m), 1.68 (3H, s).

Example 12

(R)—N-(1-hydroxy-3-(1H-indol-3-yl)propan-2-yl)-8,9-dimethoxy-3-(3-methoxyphenyl)-5,6-dihydropyrrolo[2,1-a]isoquinoline-2-carboxamide Compound 12 was prepared in an analogous fashion as described for example 6.

MS (ESI) m/z: 552 (M+H)$^+$.

$^1$H NMR δ (ppm) (CHCl$_3$-d): 8.09 (1H, s), 7.54 (1H, d, J=7.89 Hz), 7.33 (1H, d, J=8.08 Hz), 6.93-6.82 (4H, m), 6.78 (1H, d, J=2.24 Hz), 6.68 (1H, s), 5.73 (1H, d, J=6.81 Hz), 4.34-4.26 (1H, m), 3.90 (6H, d, J=16.25 Hz), 3.86-3.68 (4H, m), 3.72-3.61 (1H, m), 3.54 (1H, t, J=7.52 Hz), 3.24 (1H, s), 2.93-2.69 (4H, m),

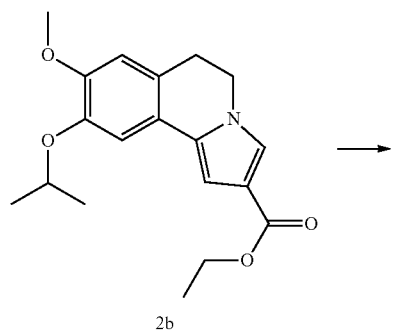

2b

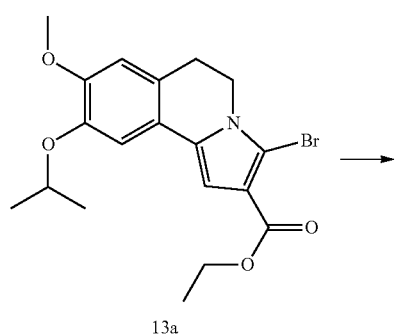

13a

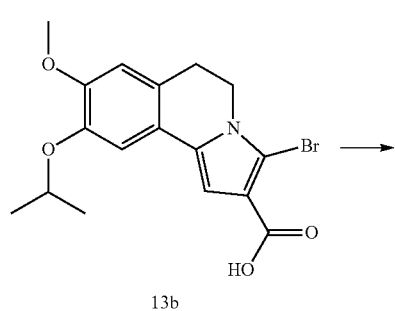

13b

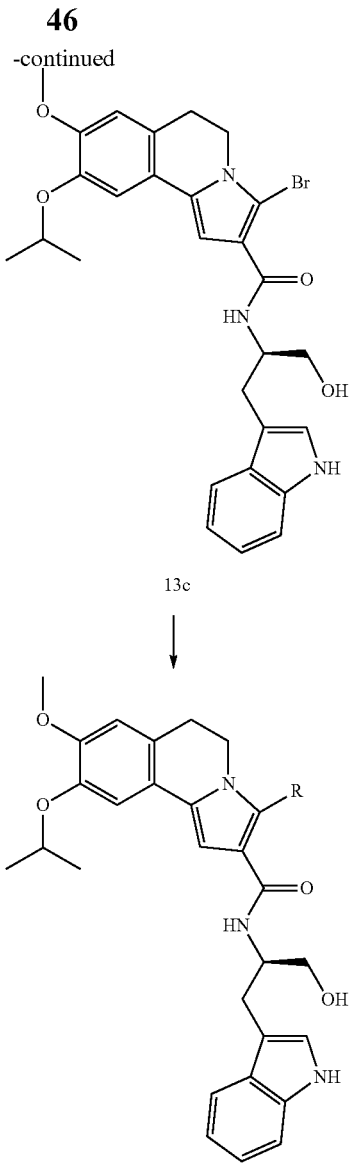

13c

13d

13. R = 4-fluorophenyl
14. R = 3-methylphenyl
15. R = 2-amino-5-pyridyl
16. R = 3-chloro-fluorophenyl
17. R = 4-hydroxyphenyl
18. R = 2-fluorophenyl
19. R = 2-furyl
20. R = 3-cyanophenyl
21. R = 3-(trifluoromethyl)phenyl

Example 13

(R)-3-(4-fluorophenyl)-N-(1-hydroxy-3-(1H-indol-3-yl)propan-2-yl)-9-isopropoxy-8-methoxy-5,6-dihydropyrrolo[2,1-a]isoquinoline-2-carboxamide

(a). ethyl 3-bromo-9-isopropoxy-8-methoxy-5,6-dihydropyrrolo[2,1-a]isoquinoline-2-carboxylate A solution of N-bromosuccinimide (0.91 g) in DCM (50 ml) was added dropwise over 45 minutes to a solution of intermediate 2b (1.88 g) in DCM (50 ml). The reaction mixture was stirred for 2 hours before quenching with saturated aqueous sodium bicarbonate solution. The aqueous phase was extracted with DCM twice and the combined organic layers were washed with water and brine, dried (MgSO$_4$) and filtered. The solvents were removed under vacuum to yield a crude solid. The residue was purified by chromatography on silica gel eluting with petrol and increasing amounts of ethyl acetate.

Yield: 1.36 g $^1$H NMR δ (ppm) (CHCl$_3$-d): 7.06 (1H, s), 6.86 (1H, s), 6.71 (1H, s), 4.60-4.50 (1H, m), 4.33 (2H, q, J=7.12 Hz), 4.16-4.07 (2H, m), 3.87 (3H, s), 3.01 (2H, t, J=6.64 Hz), 1.41-1.36 (9H, m)

(b). 3-bromo-9-isopropoxy-8-methoxy-5,6-dihydropyrrolo[2,1-a]isoquinoline-2-carboxylic Acid Sodium hydroxide (1.33 g) in water (15 ml) was added to a solution of intermediate 13a (1.33 g) in ethanol (15 ml). The mixture was heated to 80° C. for 18 hours. The solvents were removed under vacuum and the crude residue was suspended in ethyl acetate (30 ml) before acidifying to pH 2 with a aqueous 2M HCl solution. The phases were separated and the aqueous phase was re-extracted with ethyl acetate twice. The combined organic layers were washed with water and brine, dried (MgSO$_4$) and filtered. The solvents were removed under vacuum to give the product, as an off white solid.

Yield: 1.2 g $^1$H NMR δ (ppm) (DMSO-d$_6$): 12.12 (1H, s), 7.24 (1H, s), 7.01 (1H, s), 6.91 (1H, s), 4.67-4.60 (1H, m), 4.08-4.01 (2H, m), 3.77 (3H, s), 2.99 (2H, t, J=6.60 Hz), 1.25 (6H, d, J=6.01 Hz)

(c). (R)-3-bromo-N-(1-hydroxy-3-(1H-indol-3-yl)propan-2-yl)-9-isopropoxy-8-methoxy-5,6-dihydropyrrolo[2,1-a]isoquinoline-2-carboxamide 1-Ethyl-3-(3-dimethylaminopropyl) carbodiimide hydrochloride (0.91 g), 1-hydroxybenzotriazole (0.47 g), triethylamine (1.32 ml) and D-tryptophanol (0.72 g) were added to a solution of intermediate 13b (1.2 g) in DMF (20 ml). The reaction mixture was stirred for 18 hours and then the solvents were removed under vacuum to give an oily solid. The crude residue was partitioned between ethyl acetate and water and the aqueous phase was re-extracted with ethyl acetate twice. The combined organic layers were washed with a aqueous 0.2M HCl solution, saturated aqueous sodium bicarbonate solution, water and brine before drying over magnesium sulfate. The solvents were removed under vacuum to give the product, as an off white solid Yield: 1.73 g $^1$H NMR δ (ppm) (DMSO-d): 10.76 (1H, s), 7.68 (1H, d, J=7.85 Hz), 7.34 (2H, dd, J=16.04, 8.06 Hz), 7.15 (1H, s), 7.09-7.03 (2H, m), 7.02-6.96 (2H, m), 6.93 (1H, s), 4.78 (1H, t, J=5.58 Hz), 4.56 (1H, t, J=6.08 Hz), 4.20 (1H, d, J=7.52 Hz), 4.06-3.99 (3H, m), 3.77 (3H, s), 3.51 (1H, d, J=5.71 Hz), 3.46-3.42 (1H, m), 3.02-2.88 (4H, m), 1.30-1.24 (6H, m),

(d). (R)-3-(4-fluorophenyl)-N-(1-hydroxy-3-(1H-indol-3-yl)propan-2-yl)-9-isopropoxy-8-methoxy-5,6-dihydropyrrolo[2,1-a]isoquinoline-2-carboxamide Tetrakis(triphenylphosphine)palladium(0) (12.6 mg) was added to a degassed solution of intermediate 12c (60 mg), 4-fluorophenylboronic acid (23 mg) and potassium carbonate (45 mg) in a 10:1 mixture of DME:water (4 ml). The mixture was degassed by gently bubbling through nitrogen for a further 5 minutes before sealing under nitrogen and then heating to 85° C. for 18 hours. The reaction was allowed to cool to ambient temperature before water was added, extracting with ethyl acetate (3×). The combined organic layers were passed through a hydrophobic frit and concentrated under vacuum. The crude brown residue was purified by preparative HPLC eluting with acetonitrile and water to give the product, as an off white solid Yield: 28 mg $^1$H NMR δ (ppm) (CHCl$_3$-d): 8.10 (1H, s), 7.57 (1H, d, J=7.91 Hz), 7.37 (1H, d, J=8.11 Hz), 6.97-6.88 (3H, m), 6.73 (1H, s), 6.68 (1H, s), 5.65 (1H, d, J=7.08 Hz), 4.60-4.52 (1H, m), 4.36-4.29 (1H, m), 3.85 (3H, s), 3.76-3.54 (4H, m), 3.09 (1H, t, J=5.28 Hz), 2.94-2.81 (4H, m), 1.40 (6H, d, J=6.12 Hz).

Example 14

(R)—N-(1-hydroxy-3-(1H-indol-3-yl)propan-2-yl)-9-isopropoxy-8-methoxy-3-m-tolyl-5,6-dihydropyrrolo[2,1-a]isoquinoline-2-carboxamide Compound 14 was prepared in an analogous fashion as described for example 13.

MS (ESI) m/z: 564 (M+H)$^+$.

$^1$H NMR δ (ppm) (CHCl$_3$-d): 8.00 (1H, s), 7.54 (1H, d, J=7.91 Hz), 7.34 (1H, d, J=8.10 Hz), 6.86 (1H, s), 6.81 (1H, d, J=2.22 Hz), 6.68 (1H, s), 5.66 (1H, d, J=6.86 Hz), 4.60-4.52 (1H, m), 4.32-4.24 (1H, m), 3.85 (3H, s), 3.77 (2H, t, J=6.62 Hz), 3.67-3.60 (1H, m), 3.51 (1H, dd, J=10.99, 6.04 Hz), 3.14 (1H, s), 2.90 (2H, t, J=6.54 Hz), 2.84-2.67 (2H, m), 2.31 (3H, s), 1.41 (6H, d, J=6.08 Hz).

Example 15

(R)-3-(6-aminopyridin-3-yl)-N-(1-hydroxy-3-(1H-indol-3-yl)propan-2-yl)-9-isopropoxy-8-methoxy-5,6-dihydropyrrolo[2,1-a]isoquinoline-2-carboxamide Compound 15 was prepared in an analogous fashion as described for example 13.

$^1$H NMR δ (ppm) (CHCl$_3$-d): 8.12 (1H, s), 7.58 (1H, d, J=7.91 Hz), 7.39-7.03 (8H, m), 6.85 (1H, s), 6.70 (2H, d, J=10.30 Hz), 5.70 (1H, d, J=6.90 Hz), 4.59-4.50 (1H, m), 4.36-4.28 (1H, m), 3.86 (3H, s), 3.81-3.74 (2H, m), 3.68 (1H, d, J=10.89), 3.60 (1H, dd, J=10.93, 5.87 Hz), 3.15 (1H, s), 2.96-2.80 (4H, m), 1.43-1.39 (6H, m).

Example 16

(R)-3-(3-chlorophenyl)-N-(1-hydroxy-3-(1H-indol-3-yl)propan-2-yl)-9-isopropoxy-8-methoxy-5,6-dihydropyrrolo[2,1-a]isoquinoline-2-carboxamide Compound 16 was prepared in an analogous fashion as described for example 13

MS (ESI) m/z: 584, 586 (M+H)+.

¹H NMR δ (ppm) (CHCl₃-d): 8.12 (1H, s), 7.58 (1H, d, J=7.91 Hz), 7.39-7.03 (8H, m), 6.85 (1H, d, J=2.20 Hz), 6.70 (2H, d, J=10.30 Hz), 5.70 (1H, d, J=6.90 Hz), 4.59-4.50 (1H, m), 4.36-4.28 (1H, m), 3.86 (3H, s), 3.81-3.74 (2H, m), 3.68 (1H, d, J=10.89 Hz), 3.60 (1H, dd, J=10.93, 5.87 Hz), 3.15 (1H, s), 2.96-2.80 (4H, m), 1.43-1.39 (6H, m).

Example 17

(R)—N-(1-hydroxy-3-(1H-indol-3-yl)propan-2-yl)-3-(4-hydroxyphenyl)-9-isopropoxy-8-methoxy-5,6-dihydropyrrolo[2,1-a]isoquinoline-2-carboxamide Compound 17 was prepared in an analogous fashion as described for example 13.

MS (ESI) m/z: 565 (M+H)+.

¹H NMR δ (ppm) (DMSO-d₆): 10.79 (1H, s), 7.97 (1H, d, J=8.19 Hz), 7.81 (1H, s), 7.61 (1H, d, J=7.85 Hz), 7.41 (1H, s), 7.31 (1H, d, J=8.06 Hz), 7.19-7.13 (2H, m), 7.04 (1H, t, J=7.55 Hz), 6.94 (2H, t, J=10.04 Hz), 6.45 (2H, t, J=9.29 Hz), 4.73 (1H, s), 4.07-3.99 (1H, m), 3.84 (6H, d, J=17.14 Hz), 3.46 (1H, dd, J=10.80, 4.96 Hz), 2.98 (1H, dd, J=14.51, 5.98 Hz), 2.86-2.75 (5H, m).

Example 18

3-(2-fluorophenyl)-N—((R)-1-hydroxy-3-(1H-indol-3-yl)propan-2-yl)-9-isopropoxy-8-methoxy-5,6-dihydropyrrolo[2,1-a]isoquinoline-2-carboxamide Compound 18 was prepared in an analogous fashion as described for example 13.

MS (ESI) m/z: 568 (M+H)+.

¹H NMR δ (ppm) (CHCl₃-d): 8.06 (1H, s), 7.58 (1H, s), 7.39-7.28 (2H, m), 6.93 (1H, d, J=15.19 Hz), 6.69 (2H, s), 5.74 (1H, t, J=8.35 Hz), 4.61-4.52 (1H, m), 4.32 (1H, s), 3.89-3.64 (5H, m), 3.64-3.56 (1H, m), 3.10 (1H, d, J=47.31 Hz), 2.95-2.82 (4H, m), 1.41 (8H, s).

Example 19

(R)-3-(furan-2-yl)-N-(1-hydroxy-3-(1H-indol-3-yl)propan-2-yl)-9-isopropoxy-8-methoxy-5,6-dihydropyrrolo[2,1-a]isoquinoline-2-carboxamide Compound 19 was prepared in an analogous fashion as described for example 13.

MS (ESI) m/z: 540 (M+H)+.

¹H NMR δ (ppm) (CHCl₃-d): 8.18 (1H, s), 7.63 (1H, d, J=7.85 Hz), 7.40-7.32 (2H, m), 7.26-7.04 (3H, m), 6.98 (1H, s), 6.78 (1H, s), 6.69 (1H, s), 6.45 (1H, d, J=3.29 Hz), 6.35 (1H, s), 6.28 (1H, d, J=6.93 Hz), 4.59-4.49 (1H, m), 3.93 (2H, t, J=6.57 Hz), 3.86 (3H, s), 3.73 (1H, s), 3.65 (1H, d, J=9.86 Hz), 3.19 (1H, s), 3.00-2.89 (4H, m), 1.40 (6H, d, J=6.08 Hz).

Example 20

(R)-3-(3-cyanophenyl)-N-(1-hydroxy-3-(1H-indol-3-yl)propan-2-yl)-9-isopropoxy-8-methoxy-5,6-dihydropyrrolo[2,1-a]isoquinoline-2-carboxamide Compound 20 was prepared in an analogous fashion as described for example 13.

MS (ESI) m/z: 575 (M+H)+.

Example 21

(R)—N-(1-hydroxy-3-(1H-indol-3-yl)propan-2-yl)-9-isopropoxy-8-methoxy-3-(3-(trifluoromethyl)phenyl)-5,6-dihydropyrrolo[2,1-a]isoquinoline-2-carboxamide Compound 21 was prepared in an analogous fashion as described for example 13.

MS (ESI) m/z: 618 (M+H)+.

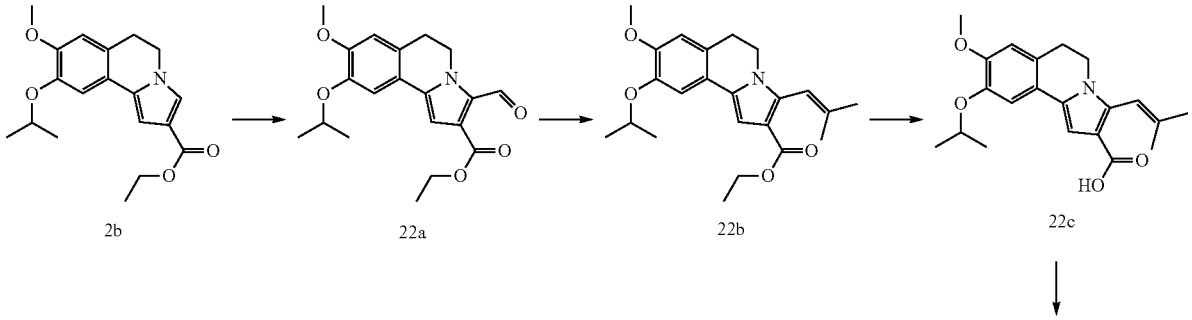

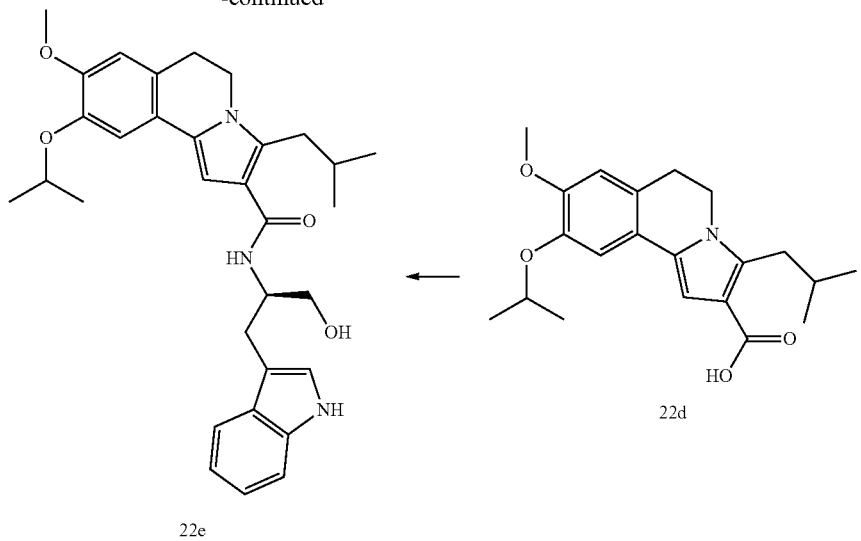

Example 22

(R)—N-(1-hydroxy-3-(1H-indol-3-yl)propan-2-yl)-3-isobutyl-9-isopropoxy-8-methoxy-5,6-dihydropyrrolo[2,1-a]isoquinoline-2-carboxamide (a). ethyl 3-formyl-9-isopropoxy-8-methoxy-5,6-dihydropyrrolo[2,1-a]isoquinoline-2-carboxylate N-butyl lithium (2.5 M in hexanes, 10.95 ml) was added dropwise to a 0° C. solution of diisopropylamine (3.3 g) in THF (60 ml), stirring for 10 minutes before cooling to −78° C. A solution of intermediate 2b (7.5 g) in THF (90 ml) was carefully added keeping the reaction temperature below −70° C., over 10 minutes. The solution was stirred at this temperature for a further 20 minutes before the addition of DMF (2.0 ml). The reaction mixture was stirred for a further 30 minutes. The reaction mixture was allowed to warm to room temperature over 1 hour and was then quenched by addition of a solution of saturated aqueous sodium bicarbonate solution and water. The crude product was extracted into ethyl acetate (2×) and the combined organic layers were washed with water and brine, dried (MgSO$_4$) and filtered. The solvents were removed under vacuum to give a dark oil that was triturated with diethyl ether (60 ml) giving a solid that was removed by filtration and dried in air. The filtrate liquors were purified on silica gel (120 g) eluting with 4:1 iso-hexane:ethyl acetate. Evaporation of the product fractions gave additional product as a crystalline off white solid. The two solids were combined to give the product as an off white solid Yield: 2.80 g $^1$H NMR δ (ppm) (CHCl$_3$-d): 10.38 (1H, s), 7.13 (1H, s), 6.90 (1H, s), 6.78-6.74 (1H, m), 4.74-4.67 (2H, m), 4.60-4.51 (1H, m), 4.38 (2H, dd, J=14.26, 7.13 Hz), 3.90-3.83 (3H, m), 3.05-2.97 (2H, m), 1.45-1.33 (9H, m).

(b). ethyl 9-isopropoxy-8-methoxy-3-(2-methylprop-1-enyl)-5,6-dihydropyrrolo[2,1-a]isoquinoline-2-carboxylate Sodium hydride (60% dispersion in oil, 27 mg) was added to a solution of intermediate 22a (200 mg) and iso-propyl-triphenylphosphonium iodide (290 mg) in THF (3 ml) before heating to 70° C. for 2 hours. The reaction mixture was cooled to room temperature and then partitioned between ethyl acetate and water. The organic phase was concentrated to dryness under vacuum to give a dark oil that was purified by chromatography on silica gel eluting with heptane and increasing amounts of ethyl acetate.

Yield: 160 mg $^1$H NMR δ (ppm) (CHCl$_3$-d): 7.10-7.05 (1H, m), 6.79-6.74 (1H, m), 6.70 (1H, s), 6.18 (1H, s), 4.62-4.50 (1H, m), 4.33-4.21 (2H, m), 3.91-3.82 (5H, m), 2.93 (2H, t, J=6.47 Hz), 1.96 (3H, s), 1.62 (3H, s), 1.39 (6H, d, J=6.09 Hz), 1.34 (3H, t, J=7.12 Hz).

(c). ethyl 9-isopropoxy-8-methoxy-3-(2-methylprop-1-enyl)-5,6-dihydropyrrolo[2,1-a]isoquinoline-2-carboxylate A aqueous 2N sodium hydroxide solution (1 ml) was added to a solution of intermediate 22b (185 mg) in ethanol (2 ml) before heating to 70° C. four 18 hours. The reaction mixture was partitioned between ethyl acetate and water. The aqueous phase was re-extracted with ethyl acetate and the combined organic layers were washed with water, dried over sodium sulphate, filtered and concentrated under vacuum to give the product as a yellow solid.

Yield: 155 mg

MS (ESI) m/z: 356 (M+H)$^+$.

$^1$H NMR δ (ppm) (CHCl$_3$-d): 7.09 (1H, s), 6.86 (1H, s), 6.71 (1H, s), 6.18 (1H, d, J=1.90 Hz), 4.58-4.51 (1H, m), 3.92-3.85 (5H, m), 2.98-2.92 (2H, m), 1.98 (3H, d, J=1.45 Hz), 1.65 (3H, d, J=1.24 Hz), 1.45-1.36 (6H, m), 1.29-1.20 (1H, m).

(d). 3-isobutyl-9-isopropoxy-8-methoxy-5,6-dihydropyrrolo[2,1-a]isoquinoline-2-carboxylic Acid A solution of intermediate 22c (75 mg) in 1:2 DCM:methanol (5 ml) was passed through the H-Cube hydrogenator at 1 ml/min/30° C./60 bar H$_2$ over a 10% Pd/C cartridge until the reaction was determined to be complete by HPLC. The solvents were removed under vacuum to give the product as a colourless oil Yield: 51 mg $^1$H NMR δ (ppm) (CHCl$_3$-d): 7.08 (1H, s), 6.83 (1H, s), 6.71 (1H, s), 4.59-4.51 (1H, m), 4.02-3.95 (2H, m), 3.90-3.83 (3H, m), 3.49 (1H, s), 3.01-2.88 (4H, m), 2.02-1.94 (1H, m), 1.39 (6H, d, J=6.07 Hz), 0.97 (6H, d, J=6.62 Hz).

(e). (R)—N-(1-hydroxy-3-(1H-indol-3-yl)propan-2-yl)-3-isobutyl-9-isopropoxy-8-methoxy-5,6-dihydro-pyrrolo[2,1-a]isoquinoline-2-carboxamide 1-Ethyl-3-(3-dimethylaminopropyl)carbodiimide hydrochloride (41 mg) was added to a solution of intermediate 22d (50 mg) and 1-hydroxybenzotriazole (20 mg) in DMF (1 ml). The mixture was stirred for 5 minutes before the addition of D-tryptophanol (28 g), stirring for a further 18 hours. The reaction mixture was partitioned between ethyl acetate and water. The organic phase was separated and washed with water, dried by passing through a hydrophobic frit and then concentrated to dryness to give an orange oil. The crude oil was purified by reverse phase preparative HPLC to give the product as a white solid Yield: 28 mg MS (ESI) m/z: 530 (M+H)$^+$.

$^1$H NMR δ (ppm) (CHCl$_3$-d): 8.12 (1H, s), 7.73 (1H, d, J=7.73 Hz), 7.40 (1H, d, J=7.95 Hz), 7.25-7.16 (2H, m), 7.12 (1H, d, J=2.33 Hz), 6.88 (1H, s), 6.71-6.67 (1H, m), 6.08-6.02 (2H, m), 4.60-4.52 (1H, m), 4.45-4.39 (1H, m), 3.96-3.88 (2H, m), 3.85 (3H, s), 3.82 (1H, dd, J=6.72, 3.72 Hz), 3.79-3.71 (1H, m), 3.58-3.53 (1H, m), 3.20-3.06 (2H, m), 2.97-2.80 (4H, m), 1.97-1.87 (1H, m), 1.43-1.34 (6H, m), 0.94-0.87 (6H, m).

Example 23

(R)—N-(1-hydroxy-3-(1H-indol-3-yl)propan-2-yl)-9-isopropoxy-8-methoxy-3-(2-methylprop-1-enyl)-5,6-dihydropyrrolo[2,1-a]isoquinoline-2-carboxamide Compound 23 was prepared in an analogous fashion as described for example 13, starting with 22c en performing step e.

MS (ESI) m/z: 528 (M+H)$^+$.

$^1$H NMR δ (ppm) (CHCl$_3$-d): 8.07 (1H, s), 7.69 (1H, d, J=7.85 Hz), 7.37 (1H, d, J=8.06 Hz), 7.23-7.18 (1H, m), 7.16-7.11 (1H, m), 7.07 (1H, d, J=2.40 Hz), 6.75 (1H, s), 6.68 (1H, s), 6.45 (1H, d, J=6.73 Hz), 5.88 (1H, s), 4.57-4.50 (1H, m), 4.48-4.42 (1H, m), 3.85 (3H, s), 3.82-3.71 (4H, m), 3.40 (1H, s), 3.06 (2H, d, J=6.97 Hz), 2.94-2.87 (2H, m), 1.72 (2H, s), 1.56 (6H, s), 1.43-1.37 (6H, m).

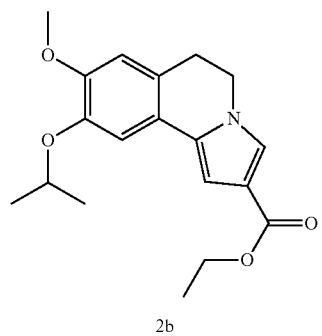

2b

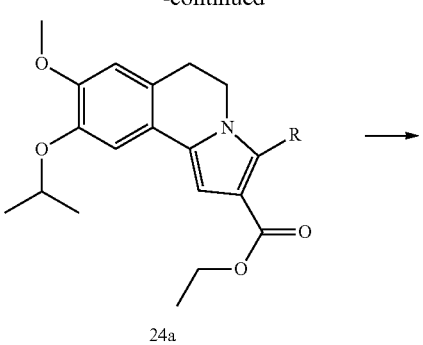

24a

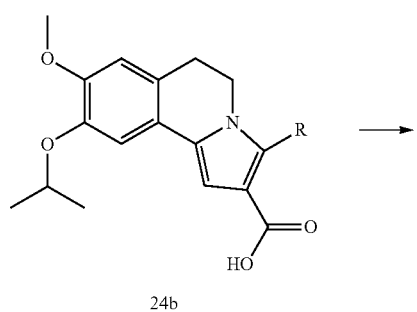

24b

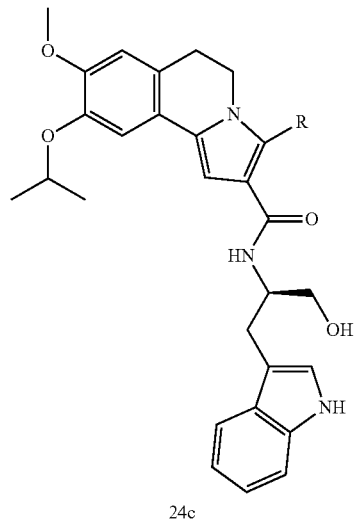

24c

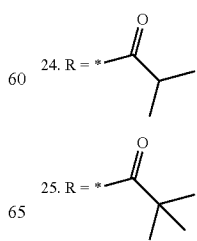

24. R = *

25. R = *

-continued

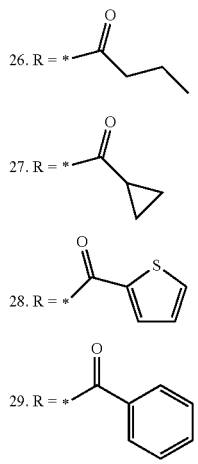

26. R = *  (butanoyl)
27. R = *  (cyclopropanecarbonyl)
28. R = *  (thiophene-2-carbonyl)
29. R = *  (benzoyl)

Example 24

(R)—N-(1-hydroxy-3-(1H-indol-3-yl)propan-2-yl)-3-isobutyryl-9-isopropoxy-8-methoxy-5,6-dihydropyrrolo[2,1-a]isoquinoline-2-carboxamide (a). ethyl 3-isobutyryl-9-isopropoxy-8-methoxy-5,6-dihydropyrrolo[2,1-a]isoquinoline-2-carboxylate Lithium diisopropylamide (0.2 M stock solution, 2.28 ml) was added dropwise to a −78° C. solution of intermediate 2b (100 mg) in dry THF (2 ml) under a nitrogen atmosphere. The mixture was stirred for 30 minutes at −78° C. before the addition of isobutyryl chloride (64 µl) in one portion, stirring for a further 15 minutes at −78° C. then allowing to warm to room temperature over 10 minutes. The reaction mixture was quenched with saturated aqueous sodium bicarbonate solution and then partitioned between water and ethyl acetate (3×). The combined organic layers were passed through a hydrophobic frit and concentrated under vacuum. The residue was purified by chromatography on silica gel eluting with petrol and increasing amounts of ethyl acetate to give the product, as a clear gum
Yield: 100 mg
$^1$H NMR δ (ppm) (CHC$_3$-d): 7.09 (1H, s), 6.77 (1H, s), 6.72 (1H, s), 4.60-4.49 (1H, m), 4.33 (2H, q, J=7.1 Hz), 4.17 (2H, t, J=6.7 Hz), 3.87 (3H, s), 3.61-3.48 (1H, m), 2.97 (2H, t, J=6.6 Hz), 1.42-1.31 (9H, m), 1.17 (6H, d, J=6.8 Hz).

(b). 3-isobutyryl-9-isopropoxy-8-methoxy-5,6-dihydropyrrolo[2,1-a]isoquinoline-2-carboxylic Acid Sodium hydroxide (29 mg) in water (0.3 ml) was added to a solution of intermediate 24a (97 mg) in ethanol (3 ml). The mixture was heated for 6 hours at 70° C. The solvents were removed under vacuum and the crude residue was dissolved in water and washed with diethyl ether (3×). The aqueous phase was acidified to ~pH 3 with a aqueous 2N HCl solution and then extracted with DCM (3×). The combined organic layers were passed through a hydrophobic frit and concentrated under vacuum to give the product, as grey solid
Yield: 75 mg
$^1$H NMR δ (ppm) (CHCl$_3$-d): 7.11 (1H, s), 6.90 (1H, s), 6.73 (1H, s), 4.60-4.51 (1H, m), 4.17 (2H, t, J=6.6 Hz), 3.88 (3H, s), 3.63-3.52 (1H, m), 3.00 (2H, t, J=6.5 Hz), 1.40 (6H, d, J=6.1 Hz), 1.19 (6H, d, J=6.8 Hz).

(c). (R)—N-(1-hydroxy-3-(1H-indol-3-yl)propan-2-yl)-3-isobutyryl-9-isopropoxy-8-methoxy-5,6-dihydropyrrolo[2,1-a]isoquinoline-2-carboxamide 1-Ethyl-3-(3-dimethylaminopropyl)carbodiimide hydrochloride (58 mg) was added to a solution of intermediate 24b (74 mg), diisopropylethylamine (105 µl), 1-hydroxybenzotriazole (41 mg) and D-tryptophanol (46 mg) in dry DMF (2 ml). The mixture was stirred at room temperature for 60 hours. Water was added and the product was extracted into ethyl acetate (5×). The combined organic layers were passed through a hydrophobic frit and concentrated under vacuum to give a pale brown oil. The residue was redissolved in DMSO and purified by preparative HPLC eluting with acetonitrile and water to give the product, as an off white solid
Yield: 47 mg
MS (ESI) m/z: 544 (M+H)$^+$.
$^1$H NMR δ (ppm) (CHCl$_3$-d): 8.22 (1H, s), 7.72 (1H, d, J=7.8 Hz), 7.38 (1H, d, J=8.0 Hz), 7.27-7.12 (2H, m), 7.11 (1H, d, J=2.4 Hz), 6.95 (1H, s), 6.70 (1H, s), 6.43 (1H, d, J=7.3 Hz), 6.22 (1H, s), 4.58-4.43 (2H, m), 4.38-4.24 (2H, m), 3.86 (3H, s), 3.84-3.71 (2H, m), 3.46-3.36 (1H, m), 3.14 (2H, d, J=6.9 Hz), 2.96-2.89 (3H, m), 1.39 (6H, d, J=6.1 Hz), 1.10 (6H, t, J=6.5 Hz).

Example 25

(R)—N-(1-hydroxy-3-(1H-indol-3-yl)propan-2-yl)-9-isopropoxy-8-methoxy-3-pivaloyl-5,6-dihydropyrrolo[2,1-a]isoquinoline-2-carboxamide Compound 25 was prepared in an analogous fashion as described for example 24.
MS (ESI) m/z: 558 (M+H)$^+$.
$^1$H NMR δ (ppm) (CHCl$_3$-d): 8.11 (1H, s), 7.72 (1H, d, J=7.8 Hz), 7.41 (1H, d, J=8.0 Hz), 7.28-7.15 (2H, m), 7.11 (1H, s), 6.91 (1H, s), 6.68 (1H, s), 6.12 (1H, d, J=6.7 Hz), 6.07 (1H, s), 4.59-4.51 (1H, m), 4.40-4.30 (1H, m), 3.90-3.71 (7H, m), 3.32 (1H, t, J=5.4 Hz), 3.17-3.05 (2H, m), 2.98-2.87 (2H, m), 1.41 (6H, t, J=5.6 Hz), 1.25 (9H, s).

Example 26

(R)-3-butyryl-N-(1-hydroxy-3-(1H-indol-3-yl)propan-2-yl)-9-isopropoxy-8-methoxy-5,6-dihydropyrrolo[2,1-a]isoquinoline-2-carboxamide Compound 26 was prepared in an analogous fashion as described for example 24.
MS (ESI) m/z: 544 (M+H)$^+$.
$^1$H NMR δ (ppm) (CHCl$_3$-d): 8.16 (1H, s), 7.72 (1H, d, J=7.85 Hz), 7.39 (1H, d, J=8.07 Hz), 6.95 (1H, s), 6.71 (1H, s), 6.48 (1H, d, J=7.35 Hz), 6.24 (1H, s), 4.58-4.36 (4H, m), 3.92-3.69 (4H, m), 3.22-3.08 (2H, m), 2.93 (2H, t, J=6.79 Hz), 2.89-2.70 (3H, m), 1.39 (6H, d, J=6.08 Hz), 0.89 (3H, t, J=7.39 Hz).

Example 27

(R)-3-(cyclopropanecarbonyl)-N-(1-hydroxy-3-(1H-indol-3-yl)propan-2-yl)-9-isopropoxy-8-methoxy-5,6-dihydropyrrolo[2,1-a]isoquinoline-2-carboxamide Compound 27 was prepared in an analogous fashion as described for example 24.

MS (ESI) m/z: 542 (M+H)+.
¹H NMR δ (ppm) (CHCl₃-d): 8.31 (1H, s), 7.70 (1H, d, J=7.8 Hz), 7.36-7.29 (2H, m), 7.17 (1H, t, J=3.9 Hz), 7.15-7.07 (2H, m), 7.02 (1H, s), 6.70 (1H, s), 6.57 (1H, s), 4.57-4.41 (2H, m), 4.38 (2H, t, J=6.7 Hz), 3.86 (3H, s), 3.90-3.64 (2H, m), 3.26 (1H, t, J=5.4 Hz), 3.11 (2H, d, J=7.0 Hz), 2.94 (2H, t, J=6.7 Hz), 2.43-2.34 (1H, m), 1.38 (6H, d, J=6.1 Hz), 1.21-1.16 (2H, m), 0.96-0.90 (2H, m).

Example 28

(R)—N-(1-hydroxy-3-(1H-indol-3-yl)propan-2-yl)-9-isopropoxy-8-methoxy-3-(thiophene-2-carbonyl)-5,6-dihydropyrrolo[2,1-a]isoquinoline-2-carboxamide Compound 28 was prepared in an analogous fashion as described for example 24.
MS (ESI) m/z: 584 (M+H)+.
¹H NMR δ (ppm) (CHCl₃-d): 8.02 (1H, s), 7.68-7.62 (2H, m), 7.59 (1H, dd, J=3.8, 1.1 Hz), 7.34 (1H, d, J=8.1 Hz), 7.19 (1H, t, J=7.7 Hz), 7.14-7.07 (3H, m), 7.04 (1H, d, J=2.3 Hz), 6.73 (2H, d, J=11.8 Hz), 6.66 (1H, d, J=6.9 Hz), 4.58-4.51 (1H, m), 4.22-4.14 (3H, m), 3.87 (3H, s), 3.51-3.47 (2H, m), 3.01-2.94 (2H, m), 2.91-2.81 (3H, m), 1.40 (6H, d, J=6.1 Hz).

Example 29

(R)-3-benzoyl-N-(1-hydroxy-3-(1H-indol-3-yl)propan-2-yl)-9-isopropoxy-8-methoxy-5,6-dihydropyrrolo[2,1-a]isoquinoline-2-carboxamide Compound 29 was prepared in an analogous fashion as described for example 24.
MS (ESI) m/z: 578 (M+H)+.
¹H NMR δ (ppm) (CHCl₃-d): 7.97 (1H, s), 7.75 (2H, d, J=7.7 Hz), 7.63 (1H, d, J=7.9 Hz), 7.57 (1H, t, J=7.4 Hz), 7.43 (2H, t, J=7.6 Hz), 7.33 (1H, d, J=8.1 Hz), 7.19 (2H, t, J=8.2 Hz), 7.11 (2H, t, J=7.6 Hz), 7.03 (1H, d, J=2.3 Hz), 6.84 (1H, s), 6.70 (1H, s), 4.58-4.51 (1H, m), 4.19-4.13 (1H, m), 4.03 (2H, t, J=6.7 Hz), 3.87 (3H, s), 3.52-3.43 (2H, m), 2.96-2.82 (5H, m), 1.41 (6H, d, J=6.1 Hz).

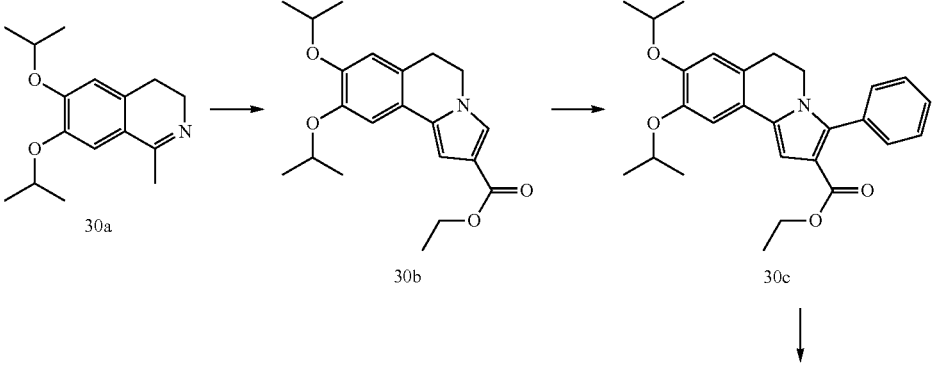

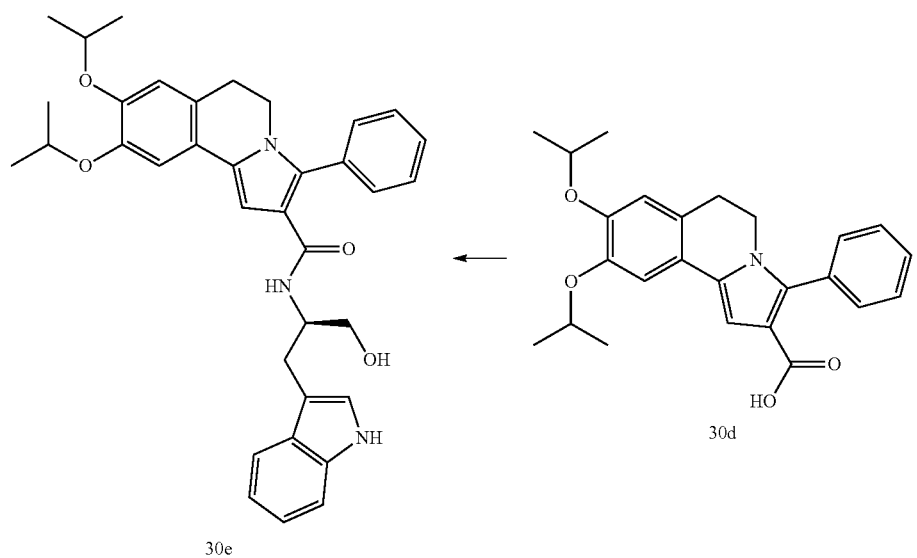

Example 30

(R)—N-(1-hydroxy-3-(1H-indol-3-yl)propan-2-yl)-8,9-diisopropoxy-3-phenyl-5,6-dihydropyrrolo[2,1-a]isoquinoline-2-carboxamide

(a). 6,7-diisopropoxy-1-methyl-3,4-dihydroisoquinoline

A solution of 1-methyl-6,7-dimethoxy-3,4-dihydroisoquinoline (35.8 g) in aqueous HBr (48%, 175 ml) was heated at 90° C. for 4.5 hours. 11% starting material, 71% mono-demethyl and 18% di-demethyl product according to LC-MS. Toluene was added to the reaction mixture and the solvent was evaporated in vacuo. The residue was dissolved in DMF (300 ml), before addition of potassium carbonate (82 g). 2-Bromopropane (41.7 ml) was added to the stirred suspension before heating at 70° C. for 18 hrs. 40% conversion according to LC-MS, hence a further aliquot of 2-bromopropane and potassium carbonate were added to the reaction mixture and heated at 70° C. for 3 hrs. The reaction mixture was extracted with ethyl acetate and water. The aqueous layer was washed with ethyl acetate and the combined organic layers were washed sequentially with water and brine, dried (MgSO$_4$), filtered and concentrated in vacuo. The residue was purified by chromatography on silica gel with petrol and increasing amounts of ethyl acetate, yielding in a pale brown solid 0.7 g, consisting of 82% mono-demethyl product, 8% di-demethyl product and 12% starting material. This material was used without further purification

(b). ethyl 8,9-diisopropoxy-5,6-dihydropyrrolo[2,1-a]isoquinoline-2-carboxylate To a mixture of 30a (26.8 g) and potassium carbonate (35 g) in acetonitrile (270 ml) was added dropwise ethylbromopyruvate (17.3 ml). The reaction mixture was refluxed for 3 hrs. The reaction was allowed to cool to ambient temperature before a saturated aqueous NaHCO$_3$ solution was added. The aqueous phase was extracted with ethyl acetate twice. The combined organic layers were washed with brine. The organic layer was dried (MgSO$_4$), filtered and concentrated in vacuo. The residue was purified by chromatography on silica gel eluting with petrol and increasing amounts of ethyl acetate. The pure fractions of the desired product were concentrated in vacuo.

(c). ethyl 8,9-diisopropoxy-3-phenyl-5,6-dihydropyrrolo[2,1-a]isoquinoline-2-carboxylate Compound 30b (232 mg), phenylbromide (117 mg), triphenylphosphine (34 mg) and cesium carbonate (459 mg) were suspended in degassed dioxane (4 ml). Palladium(II) acetate (15 mg) was added and the mixture was further degassed for 5 minutes and heated at 100° C. for 18 hours. The reaction mixture was degassed and recharged with triphenylphosphine and palladium(II) acetate and heated for a further 18 hours. The reaction mixture was diluted with ethyl acetate and water and filtered through celite. The organic phase was dried (MgSO$_4$), filtered and concentrated to a yellow oil. The residue was purified by chromatography on silica gel with hexane and increasing amounts of ethyl acetate. The pure fractions were concentrated to a colorless oil.

Yield: 162 mg
MS (ESI) m/z: 434 (M+H)$^+$.

(d). 8,9-diisopropoxy-3-phenyl-5,6-dihydropyrrolo[2,1-a]isoquinoline-2-carboxylic Acid A aqueous 2N sodium hydroxide solution (21.9 ml) was added to a solution of intermediate 30c (161 mg) in ethanol (4 ml). The mixture was heated for 18 hours at 60° C. The solvents were removed under vacuum and the crude residue was partitioned between a aqueous 1N HCl solution and ethyl acetate. The organic phase was dried (MgSO$_4$), filtered and concentrated to a pale brown solid.

Yield: 145 mg
MS (ESI) m/z: 406 (M+H)$^+$.

(e). (R)—N-(1-hydroxy-3-(1H-indol-3-yl)propan-2-yl)-8,9-diisopropoxy-3-phenyl-5,6-dihydropyrrolo[2,1-a]isoquinoline-2-carboxamide 1-Ethyl-3-(3-dimethylaminopropyl)carbodiimide hydrochloride (104 mg) was added to a solution of intermediate 30d (145 mg), diisopropylethylamine (188 µl), 1-hydroxybenzotriazole (73 mg) and D-tryptophanol (82 mg) in dry DMF (4 ml). The mixture was stirred at room temperature for 18 hours. The reaction mixture was diluted with ethyl acetate and washed sequentially with a aqueous 1N HCl solution, a saturated aqueous NaHCO$_3$ solution and brine. The organic layer was dried (MgSO$_4$) and concentrated in vacuo to a pale brown oil. The residue was purified by chromatography on silica gel with DCM and increasing amounts of methanol (max. 7% in DCM). The pure fraction were collected and concentrated in vacuo, yielding in a pale yellow solid.

$^1$H NMR δ (ppm) (CHCl$_3$-d): 8.32 (1H, s), 7.52 (1H, d, J=7.89 Hz), 7.35-7.19 (6H, m), 7.20-7.06 (3H, m), 6.83 (1H, s), 6.78 (1H, d, J=2.3 Hz), 6.71 (1H, s), 5.64 (1H, d, J=6.95), 4.54-4.40 (2H, m), 4.33-4.23 (1H, m), 3.73 (2H, t, J=6.50 Hz), 3.61 (1H, d, J=10.88 Hz), 3.51 (1H, dd, J=10.94, 5.95 Hz), 3.31 (1H, s), 2.88-2.68 (4H, m), 1.34 (12H, dd, J=11.62, 6.09 Hz).

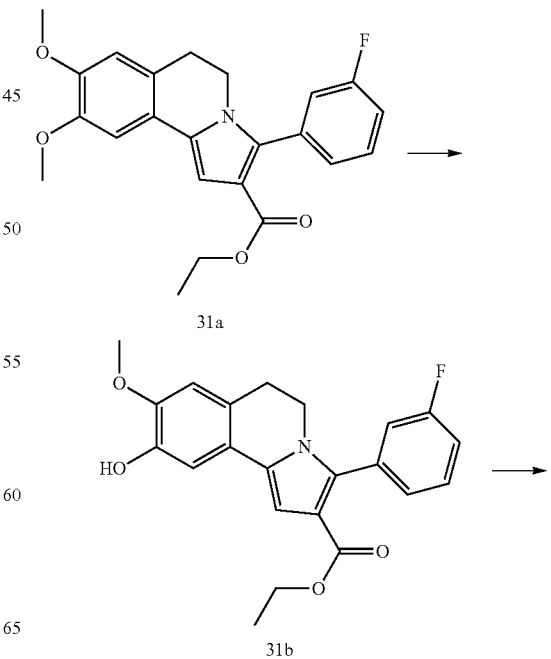

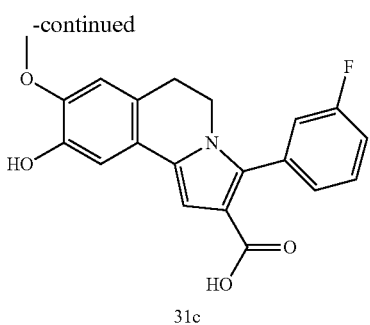

31c

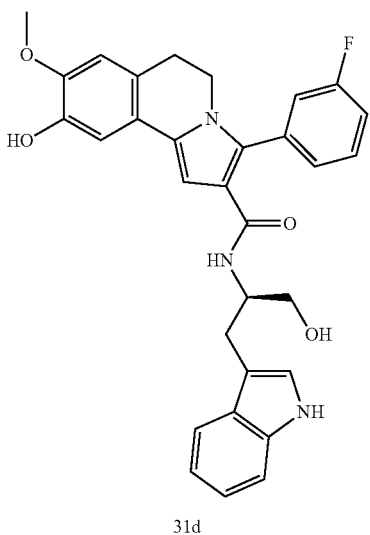

31d

Example 31

(R)-3-(3-fluorophenyl)-9-hydroxy-N-(1-hydroxy-3-(1H-indol-3-yl)propan-2-yl)-8-methoxy-5,6-dihydropyrrolo[2,1-a]isoquinoline-2-carboxamide (a). ethyl 3-(3-fluorophenyl)-8,9-dimethoxy-5,6-dihydropyrrolo[2,1-a]isoquinoline-2-carboxylate Compound 31a was prepared in an analogous fashion as described for example 5c.

(b). ethyl 3-(3-fluorophenyl)-8,9-dimethoxy-5,6-dihydropyrrolo[2,1-a]isoquinoline-2-carboxylate To a solution of compound 31a (124 mg) in DCE (2 ml) was added aluminium chloride (120 mg). The mixture was heated at 50° C. for 75 minutes. The reaction mixture was diluted with DCM and quenched with solid NaHCO$_3$ and acidified with a aqueous 2M HCl solution. The organic layer was washed with water and brine, dried (Na$_2$SO$_4$), filtered and concentrated in vacuo to give a pale yellow oil.

Yield: 114 mg (the product is a mixture of regioisomers (20:80). The crude product used without further purification.

(c) 3-(3-fluorophenyl)-9-hydroxy-8-methoxy-5,6-dihydropyrrolo[2,1-a]isoquinoline-2-carboxylic Acid To a solution of the mixture of isomers 31b (114 mg) in ethanol (2 ml) was added a aqueous 2M sodium hydroxide solution (0.75 ml). The mixture was heated at 50° C. for 18 hrs. The reaction mixture was diluted with ethyl acetate and extracted with a aqueous 2M HCl solution. The organic layer was washed with water, brine, dried (MgSO$_4$), filtered and concentrated in vacuo to yield a pale yellow oil.

Yield: 110 mg (d). (R)-3-(3-fluorophenyl)-9-hydroxy-N-(1-hydroxy-3-(1H-indol-3-yl)propan-2-yl)-8-methoxy-5,6-dihydropyrrolo[2,1-a]isoquinoline-2-carboxamide 1-Ethyl-3-(3-dimethylaminopropyl)carbodiimide hydrochloride (87 mg) was added to a solution of a mixture of regioisomers 31c (110 mg), triethylamine (126 µl), 1-hydroxybenzotriazole (43 mg) and D-tryptophanol (71 mg) in dry DMF (2 ml). The reaction mixture was stirred at room temperature for 60 hours. The solvent was removed under vacuum to give a yellow oil. The oil was redissolved in ethyl acetate and washed with water (3×). The combined organic layers were passed through a hydrophobic frit and concentrated under vacuum. The crude residue was redissolved in MeCN and purified by preparative HPLC, eluting with acetonitrile and water to give the product as an off-white solid Yield: 16 mg $^1$H NMR δ (ppm) (CHCl$_3$-d): 8.4 (1H, s), 7.65-7.55 (2H, m), 7.19-7.25 (3H, m), 7.19-7.00 (7H, m), 6.68 (1H, s), 6.00 (1H, d, J=7.25), 5.82 (1 h, bs), 4.40-4.30 (1H, m), 3.90 (3H, s), 3.67-3.53 (2H, m), 2.98-2.70 (6H, m).

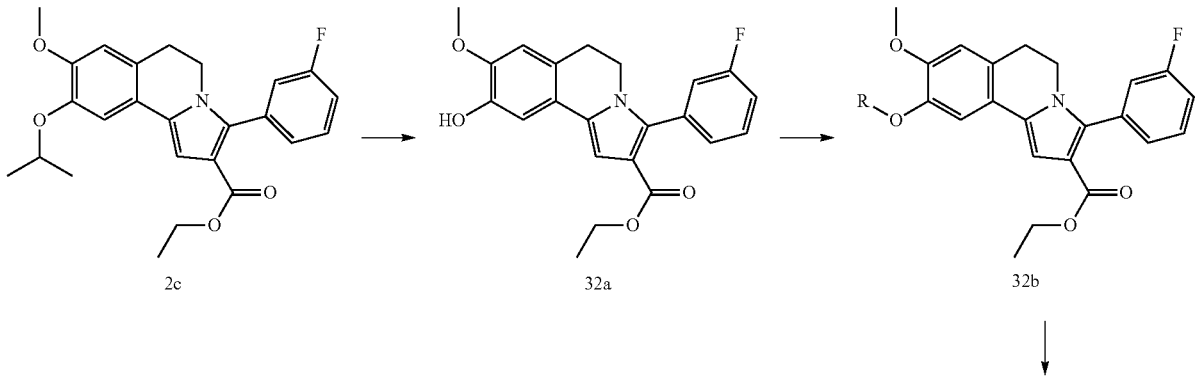

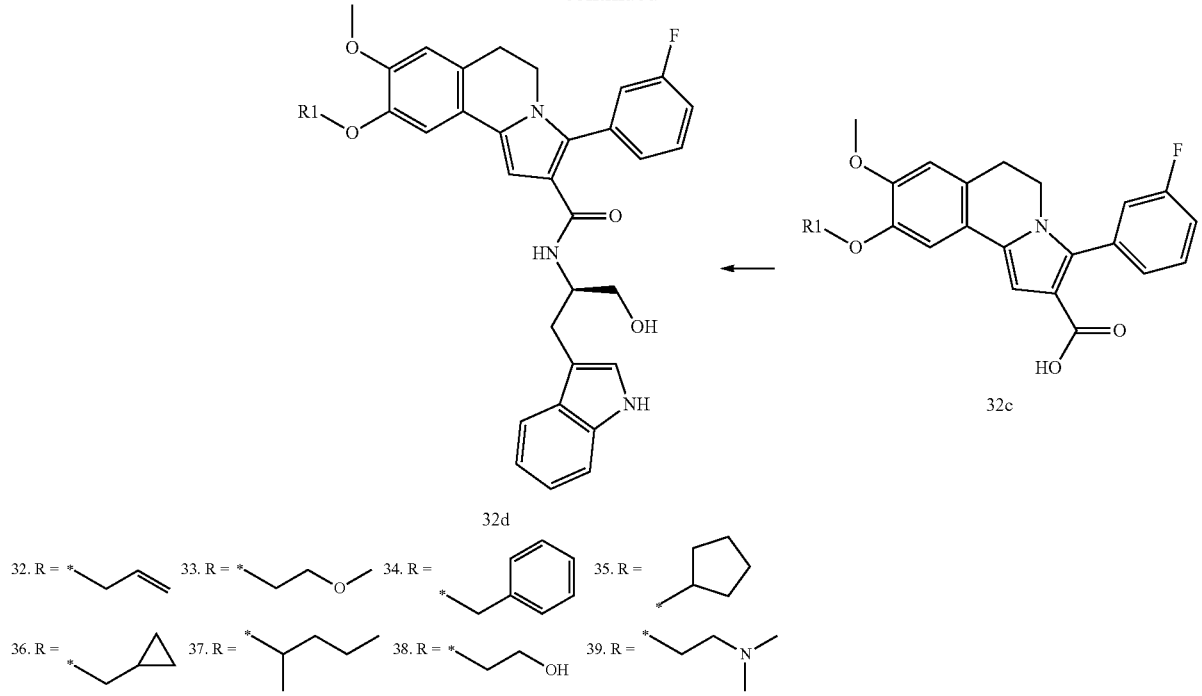

Example 32

(R)-9-(allyloxy)-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide (a). ethyl 3-(3-fluorophenyl)-9-hydroxy-8-methoxy-5,6-dihydropyrrolo[2,1-a]isoquinoline-2-carboxylate Boron tribromide (1.05 ml) was added dropwise to a −40° C. solution of intermediate 2c (890 mg) in DCM (25 ml) under a nitrogen atmosphere. The reaction mixture was stirred for 30 minutes, then a further aliquot of boron tribromide (1.05 ml) was added dropwise and the mixture stirred for a further 2 hours at −40° C. The reaction was quenched with water and the aqueous phase was extracted with DCM (3×). The combined organic layers were passed through a hydrophobic frit and the solvent was removed under vacuum. The residue was purified by chromatography on silica gel eluting with heptane and increasing amounts of ethyl acetate to give the product as a pale pink solid.

Yield: 550 mg $^{1}$H NMR δ (ppm) (CHCl$_3$-d): 7.45-7.37 (1H, m), 7.22-7.08 (4H, m), 6.90 (1H, s), 6.69 (1H, s), 5.58 (1H, s), 4.16 (2H, q, J=7.1 Hz), 3.90 (3H, s), 3.86 (2H, t, J=6.5 Hz), 2.92 (2H, t, J=6.5 Hz), 1.18 (3H, t, J=7.1 Hz).

(b). ethyl 9-(allyloxy)-3-(3-fluorophenyl)-8-methoxy-5,6-dihydropyrrolo[2,1-a]isoquinoline-2-carboxylate Allyl chloride (24 μl) was added to a solution of intermediate 32a (76 mg) and potassium carbonate (42 mg) in DMF (2 ml), heating to 60° C. for 18 hours. The mixture was concentrated to dryness under vacuum and the residue was suspended in water. The crude product was extracted into ethyl acetate (3×) and the combined organic layers were passed through a hydrophobic frit and concentrated under vacuum to give the product as an off white solid Yield: 82 mg $^{1}$H NMR δ (ppm) (CHCl$_3$-d): 7.45-7.37 (1H, m), 7.20-7.09 (4H, m), 6.89 (1H, s), 6.71 (1H, s), 6.18-6.07 (1H, m), 5.46 (1H, dq, J=17.3, 1.6 Hz), 5.34 (1H, d, J=1.5 Hz), 4.67 (2H, d, J=5.4 Hz), 4.16 (2H, q, J=7.12 Hz), 3.90-3.82 (5H, m), 2.97-2.89 (2H, m), 1.18 (3H, t, J=7.1 Hz).

(c). 9-(allyloxy)-3-(3-fluorophenyl)-8-methoxy-5,6-dihydropyrrolo[2,1-a]isoquinoline-2-carboxylic Acid Sodium hydroxide (23 mg) in water (0.3 ml) was added to a solution of intermediate 32b (80 mg) in ethanol (3 ml). The mixture was heated to 80° C. for 3 hours. The solvents were removed under vacuum and the residue redissolved in water and washed with diethyl ether (3×). The aqueous layer was acidified to ~pH 4 with a aqueous 4M HCl solution and extracted into DCM (3×) and ethyl acetate (3×). The combined organic layers were passed through a hydrophobic frit and concentrated under vacuum to give the product, as an off white solid Yield: 73 mg MS (ESI) m/z: 394 (M+H)$^{+}$.

(d). (R)-9-(allyloxy)-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide 1-Ethyl-3-(3-dimethylaminopropyl)carbodiimide hydrochloride (52 mg) was added to a solution of intermediate 32c (71 mg), diisopropylethylamine (94 μl), 1-hydroxybenzotriazole (37 mg) and D-tryptophanol (41 mg) in dry DMF (2 ml). The reaction mixture was stirred at room temperature for 60 hours. The solvent was removed under vacuum to give a yellow oil. The oil was redissolved in ethyl acetate and washed with water (3×). The combined organic layers were passed through a hydrophobic frit and concentrated under vacuum. The crude residue was redissolved in MeCN and purified by preparative HPLC eluting with acetonitrile and water to give the product as an off-white solid Yield: 14 mg, 9%.

MS (ESI) m/z: 566 (M+H)+.

$^1$H NMR δ (ppm) (CHCl$_3$-d): 8.08 (1H, s), 7.57 (1H, d, J=7.9 Hz), 7.36 (1H, d, J=8.1 Hz), 7.26-7.15 (2H, m), 7.11 (1H, t, J=7.5 Hz), 7.05-6.96 (4H, m), 6.88 (1H, d, J=2.3 Hz), 6.70 (2H, d, J=11.1 Hz), 6.17-6.06 (1H, m), 5.69 (1H, d, J=7.0 Hz), 5.45 (1H, dd, J=17.3, 1.7 Hz), 5.32 (1H, dd, J=10.5, 1.5 Hz), 4.65 (2H, d, J=5.4 Hz), 4.37-4.29 (1H, m), 3.88 (3H, s), 3.77 (2H, t, J=6.6 Hz), 3.70-3.55 (2H, m), 3.06 (1H, s), 2.94-2.80 (4H, m).

Example 33

(R)-3-(3-fluorophenyl)-N-(1-hydroxy-3-(1H-indol-3-yl)propan-2-yl)-8-methoxy-9-(2-methoxyethoxy)-5,6-dihydropyrrolo[2,1-a]isoquinoline-2-carboxamide Compound 33 was prepared in an analogous fashion as described for example 32.

MS (ESI) m/z: 584 (M+H)+.

$^1$H NMR δ (ppm) (CHCl$_3$-d): 8.35 (1H, s), 7.56 (1H, d, J=7.9 Hz), 7.34 (1H, d, J=8.1 Hz), 7.26-7.14 (2H, m), 7.13-6.95 (5H, m), 6.87 (1H, d, J=2.3 Hz), 6.68 (2H, d, J=6.6 Hz), 5.76 (1H, d, J=7.0 Hz), 4.37-4.27 (1H, m), 4.20 (2H, t, J=4.8 Hz), 3.85 (3H, s), 3.81 (2H, t, J=4.8 Hz), 3.75 (2H, t, J=6.5 Hz), 3.68-3.53 (2H, m), 3.47 (3H, s), 2.95-2.78 (4H, m).

Example 34

(R)-9-(benzyloxy)-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide Compound 34 was prepared in an analogous fashion as described for example 32.

MS (ESI) m/z: 616 (M+H)+.

$^1$H NMR δ (ppm) (CHCl$_3$-d): 8.41 (1H, s), 7.53 (1H, d, J=7.9 Hz), 7.45 (2H, d, J=7.5 Hz), 7.35 (2H, t, J=7.5 Hz), 7.30-7.23 (2H, m), 7.22-7.09 (2H, m), 7.10-7.02 (2H, m), 6.98-6.91 (3H, m), 6.79 (1H, d, J=2.4 Hz), 6.67 (2H, d, J=4.2 Hz), 5.76 (1H, d, J=7.1 Hz), 5.13 (2H, s), 4.36-4.26 (1H, m), 3.85 (3H, s), 3.69 (2H, t, J=6.4 Hz), 3.62-3.48 (2H, m), 3.39 (1H, s), 2.91-2.72 (4H, m).

Example 35

(R)-9-(cyclopentylmethoxy)-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide Compound 35 was prepared in an analogous fashion as described for example 32.

MS (ESI) m/z: 594 (M+H)+.

$^1$H NMR δ (ppm) (CHCl$_3$-d): 8.01 (1H, s), 7.57 (1H, d, J=7.9 Hz), 7.36 (1H, d, J=8.10 Hz), 7.24-7.17 (2H, m), 7.12 (1H, t, J=7.5 Hz), 7.08-6.96 (4H, m), 6.88 (1H, d, J=2.3 Hz), 6.75 (1H, s), 6.68 (1H, d, J=6.9 Hz), 5.68 (1H, d, J=6.9 Hz), 4.83-4.78 (1H, m), 4.36-4.30 (1H, m), 3.85 (3H, s), 3.77 (2H, t, J=6.6 Hz), 3.71-3.55 (2H, m), 3.06 (1H, s), 2.94-2.80 (4H, m), 2.04-1.90 (6H, m), 1.91-1.82 (2H, m).

Example 36

(R)-9-(cyclopropylmethoxy)-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide Compound 36 was prepared in an analogous fashion as described for example 32.

MS (ESI) m/z: 580 (M+H)+.

$^1$H NMR δ (ppm) (CHCl$_3$-d): 7.99 (1H, s), 7.58 (1H, d, J=7.9 Hz), 7.37 (1H, d, J=8.1 Hz), 7.28-7.18 (2H, m), 7.12 (1H, t, J=7.5 Hz), 7.09-6.99 (4H, m), 6.89 (1H, d, J=2.3 Hz), 6.70 (2H, d, J=9.9 Hz), 5.69 (1H, d, J=6.9 Hz), 4.35-4.30 (1H, m), 3.93-3.86 (5H, m), 3.78 (2H, t, J=6.5 Hz), 3.71-3.65 (1H, m), 3.62-3.55 (1H, m), 3.03 (1H, t, J=5.4 Hz), 2.94-2.83 (4H, m), 1.40-1.35 (1H, m), 0.71-0.65 (2H, m), 0.43-0.38 (2H, m).

Example 37

3-(3-fluorophenyl)-N—((R)-1-hydroxy-3-(1H-indol-3-yl)propan-2-yl)-8-methoxy-9-(pentan-2-yloxy)-5,6-dihydropyrrolo[2,1-a]isoquinoline-2-carboxamide Compound 37 was prepared in an analogous fashion as described for example 32.

MS (ESI) m/z: 596 (M+H)+.

$^1$H NMR δ (ppm) (CHCl$_3$-d): 8.01 (1H, s), 7.57 (1H, d, J=7.9 Hz), 7.37 (1H, d, J=8.1 Hz), 7.21 (2H, t, J=7.6 Hz), 7.12 (1H, t, J=7.5 Hz), 7.08-6.98 (4H, m), 6.88 (1H, d, J=2.3 Hz), 6.74 (1H, s), 6.69 (1H, s), 5.68 (1H, d, J=6.9 Hz), 4.41-4.29 (2H, m), 3.85 (3H, s), 3.78 (2H, t, J=6.6 Hz), 3.71-3.65 (1H, m), 3.62-3.55 (1H, m), 3.10 (1H, t, J=5.4 Hz), 2.93-2.83 (4H, m), 1.86-1.50 (4H, m), 1.35 (3H, dd, J=6.1, 2.0 Hz), 1.03-0.94 (3H, m).

Example 38

(R)-3-(3-fluorophenyl)-N-(1-hydroxy-3-(1H-indol-3-yl)propan-2-yl)-9-(2-hydroxyethoxy)-8-methoxy-5,6-dihydropyrrolo[2,1-a]isoquinoline-2-carboxamide Compound 38 was prepared in an analogous fashion as described for example 32.

MS (ESI) m/z: 570 (M+H)+.

$^1$H NMR δ (ppm) (CHCl$_3$-d): 8.06 (1H, s), 7.58 (1H, d, J=7.9 Hz), 7.37 (1H, d, J=8.1 Hz), 7.25-7.18 (2H, m), 7.14-6.97 (5H, m), 6.91 (1H, d, J=2.3 Hz), 6.69 (2H, d, J=9.4 Hz), 5.71 (1H, d, J=6.9 Hz), 4.36-4.30 (1H, m), 4.19 (2H, t, J=4.5 Hz), 3.98 (2H, t, J=4.3 Hz), 3.87 (3H, s), 3.78 (2H, t, J=6.5 Hz), 3.71-3.55 (2H, m), 3.07 (1H, s), 2.97-2.82 (4H, m), 2.58 (1H, s).

Example 39

(R)-9-(2-(dimethylamino)ethoxy)-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide Compound 39 was prepared in an analogous fashion as described for example 32.

$^1$H NMR δ (ppm) (CHCl$_3$-d): 8.47 (1H, s), 7.59 (1H, d, J=7.9 Hz), 7.38 (1H, d, J=8.0 Hz), 7.31-7.15 (2H, m), 7.15-6.98 (5H, m), 6.95 (1H, s), 6.68 (1H, s), 6.60 (1H, s), 5.77 (1H, s), 4.46-4.18 (1H, m), 4.22 (2H, t, J=6.1 Hz), 3.86 (3H, s), 3.78 (2H, t, J=6.6 Hz), 3.74-3.57 (6H, m), 2.43 (6H, s).

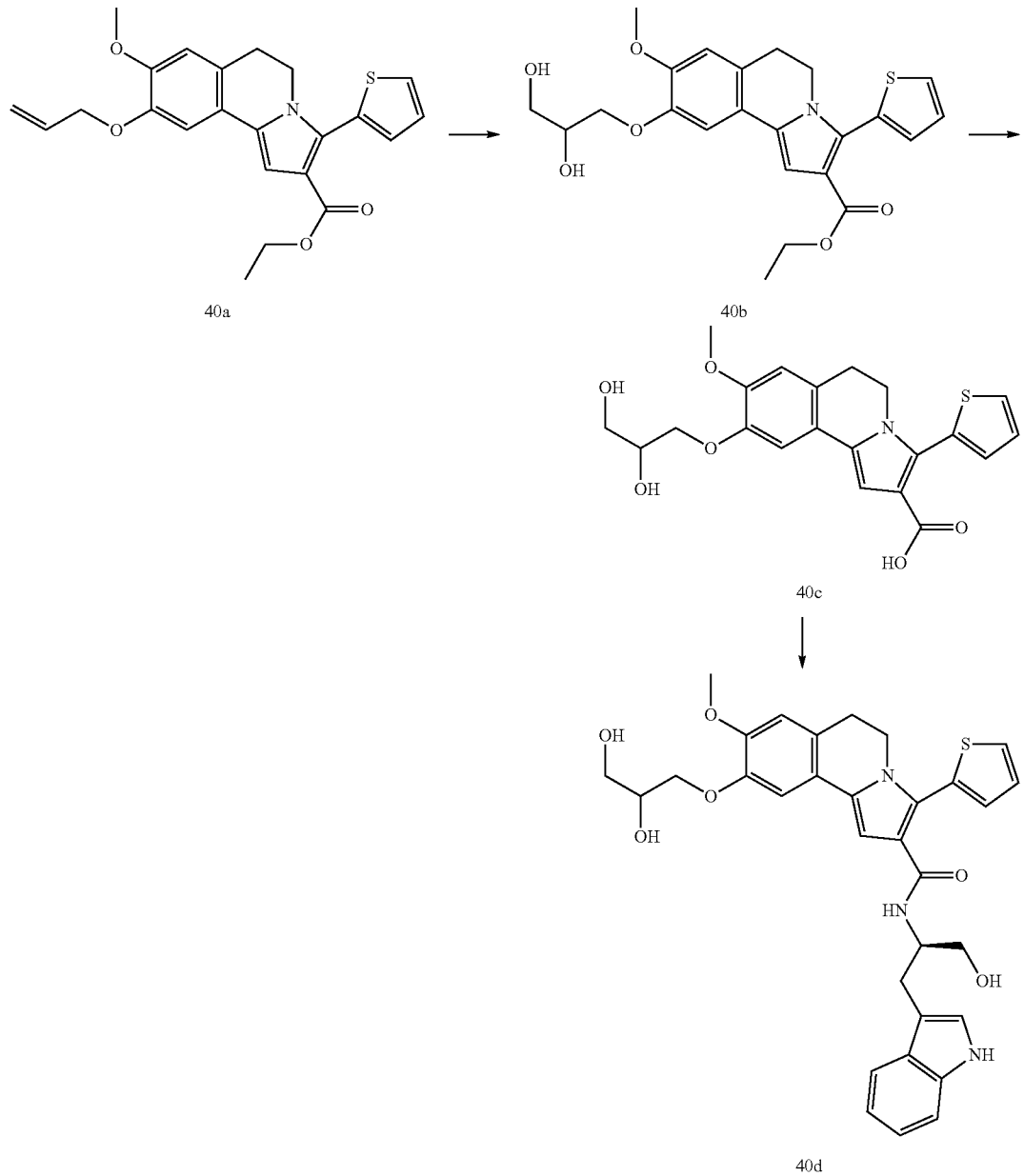

$^1$H NMR δ (ppm) (CHCl$_3$-d): 7.48 (1H, dd, J=4.1, 2.3 Hz), 7.15-7.10 (3H, m), 6.89 (1H, s), 6.71 (1H, s), 6.18-6.07 (1H, m), 5.48 (1H, dd, J=17.2, 1.7 Hz), 5.32 (1H, dd, J=10.5, 1.5 Hz), 4.67 (2H, dt, J=5.4, 1.5 Hz), 4.19 (2H, q, J=7.1 Hz), 3.94 (2H, t, J=6.60 Hz), 3.89 (3H, s), 2.94 (2H, t, J=6.6 Hz), 1.21 (3H, t, J=7.1 Hz).

(b). ethyl 9-(2,3-dihydroxypropoxy)-8-methoxy-3-(thiophen-2-yl)-5,6-dihydropyrrolo[2,1-a]isoquino-line-2-carboxylate Osmium tetraoxide (1.5 mg) was added to a solution of intermediate 40a (100 mg) and N-methylmorpholine N-oxide (42 mg) in a 1:1 mixture of water and THF (2 ml). The reaction tube was sealed and stirred at room temperature for 16 hours. The crude product was extracted into DCM (3×) and the combined organics were passed through a hydro-

Example 40

9-(2,3-dihydroxypropoxy)-N—((R)-1-hydroxy-3-(1H-indol-3-yl)propan-2-yl)-8-methoxy-3-(thiophen-2-yl)-5,6-dihydropyrrolo[2,1-a]isoquinoline-2-carboxamide (a). ethyl 9-(allyloxy)-8-methoxy-3-(thiophen-2-yl)-5,6-dihydropyrrolo[2,1-a]isoquinoline-2-carboxylate Compound 40a was prepared in an analogous fashion as described for compound 32b phobic frit and purified by chromatography on silica gel eluting with DCM and increasing amounts of methanol.

Yield: 45 mg

MS (ESI) m/z: 444 (M+H)+.

$^1$H NMR δ (ppm) (CHCl$_3$-d): 7.48 (1H, t, J=3.3 Hz), 7.16-7.11 (3H, m), 6.91 (1H, s), 6.72 (1H, s), 4.26-4.09 (5H, m), 3.94 (2H, t, J=6.5 Hz), 3.96-3.75 (5H, m), 3.15 (1H, s), 2.95 (2H, t, J=6.6 Hz), 2.45 (1H, s), 1.22 (3H, t, J=7.1 Hz).

(c). 9-(2,3-di hydroxypropoxy)-8-methoxy-3-(thiophen-2-yl)-5,6-dihydropyrrolo[2,1-a]isoquinoline-2-carboxylic Acid Sodium hydroxide (12 mg) in water (0.2 ml) was added to a solution of intermediate 40b (44 mg) in ethanol (2 ml). The reaction mixture was heated to 80° C. for 3 hours. The solvents were removed under vacuum and the residue redissolved in water, washing with diethyl ether (2×). The aqueous layer was acidified to ~pH 4 with a aqueous 4M HCl solution and the product extracted into ethyl acetate (3×). The combined organics were passed through a hydrophobic frit and concentrated under vacuum to give the product as a yellow solid.

Yield: 36 mg $^1$H NMR δ (ppm) (CHCl$_3$-d): 7.49 (1H, dd, J=4.9, 1.5 Hz), 7.18-7.11 (3H, m), 6.95 (1H, s), 6.72 (1H, s), 4.25-4.19 (1H, m), 4.14-4.08 (2H, m), 3.94 (2H, t, J=6.6 Hz), 3.87 (3H, s), 3.84 (2H, dd, J=7.1, 3.7 Hz), 2.95 (2H, t, J=6.6 Hz).

(d). 9-(2,3-dihydroxypropoxy)-N—((R)-1-hydroxy-3-(1H-indol-3-yl)propan-2-yl)-8-methoxy-3-(thiophen-2-yl)-5,6-dihydropyrrolo[2,1-a]isoquinoline-2-carboxamide 1-Ethyl-3-(3-dimethylaminopropyl)carbodiimide hydrochloride (23 mg) was added to a solution of intermediate 40c (33 mg), diisopropylethylamine (42 µl), 1-hydroxybenzotriazole (16 mg), and D-tryptophanol (18 mg) in dry DMF (1 ml). The mixture was stirred at room temperature for 5 hours. The solvent was removed under vacuum and water was added, extracting with ethyl acetate (3×). The combined organic layers were passed through a hydrophobic frit and concentrated to dryness under vacuum. The crude residue was redissolved in MeCN and purified by preparative HPLC eluting with acetonitrile and water to give the product as an off white solid.

Yield: 28 mg

MS (ESI) m/z: 588 (M+H)+.

$^1$H NMR δ (ppm)(DMSO-d$_6$): 10.77 (1H, s), 7.68 (1H, t, J=3.3 Hz), 7.61 (1H, d, J=7.9 Hz), 7.32 (1H, d, J=8.1 Hz), 7.17-7.11 (3H, m), 7.09-6.95 (4H, m), 6.90 (2H, s), 4.97 (1H, d, J=5.1 Hz), 4.70 (2H, q, J=6.1 Hz), 4.15-4.09 (1H, m), 4.08-3.95 (1H, m), 3.92-3.89 (1H, m), 3.87-3.81 (3H, m), 3.78 (3H, s), 3.50-3.40 (2H, m), 3.42-3.38 (1H, m), 3.35-3.28 (1H, m), 2.94-2.88 (3H, m), 2.82-2.77 (1H, m).

Example 41

9-(2,3-dihydroxypropoxy)-N—((R)-1-hydroxy-3-(1H-indol-3-yl)propan-2-yl)-8-methoxy-3-(thiophen-2-yl)-5,6-dihydropyrrolo[2,1-a]isoquinoline-2-carboxamide (a). ethyl 9-(allyloxy)-8-methoxy-3-(thiophen-2-yl)-5,6-dihydropyrrolo[2,1-a]isoquinoline-2-carboxylate Example 41 was prepared in an analogous fashion as described for example 32 starting from compound 40a.

$^1$H NMR δ (ppm) (CHCl$_3$-d): 7.48 (1H, dd, J=4.1, 2.3 Hz), 7.15-7.10 (3H, m), 6.89 (1H, s), 6.71 (1H, s), 6.18-6.07 (1H, m), 5.48 (1H, dd, J=17.2, 1.7 Hz), 5.32 (1H, dd, J=10.5, 1.5 Hz), 4.67 (2H, dt, J=5.4, 1.5 Hz), 4.19 (2H, q, J=7.1 Hz), 3.94 (2H, t, J=6.60 Hz), 3.89 (3H, s), 2.94 (2H, t, J=6.6 Hz), 1.21 (3H, t, J=7.1 Hz).

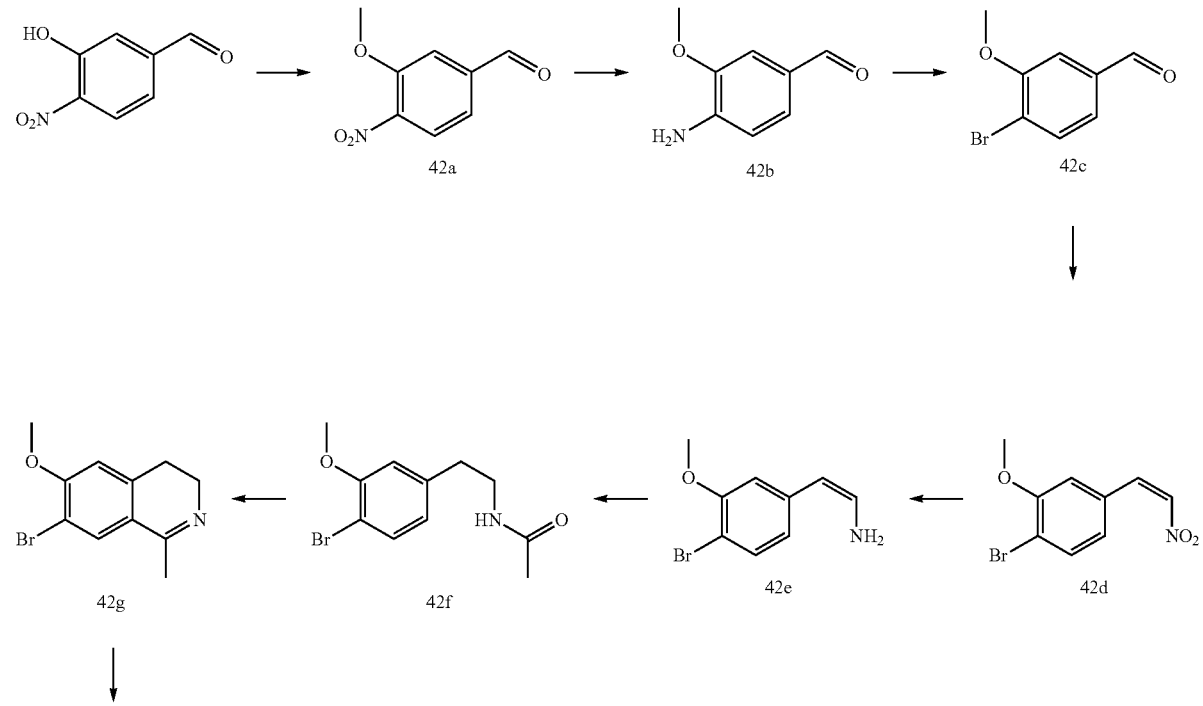

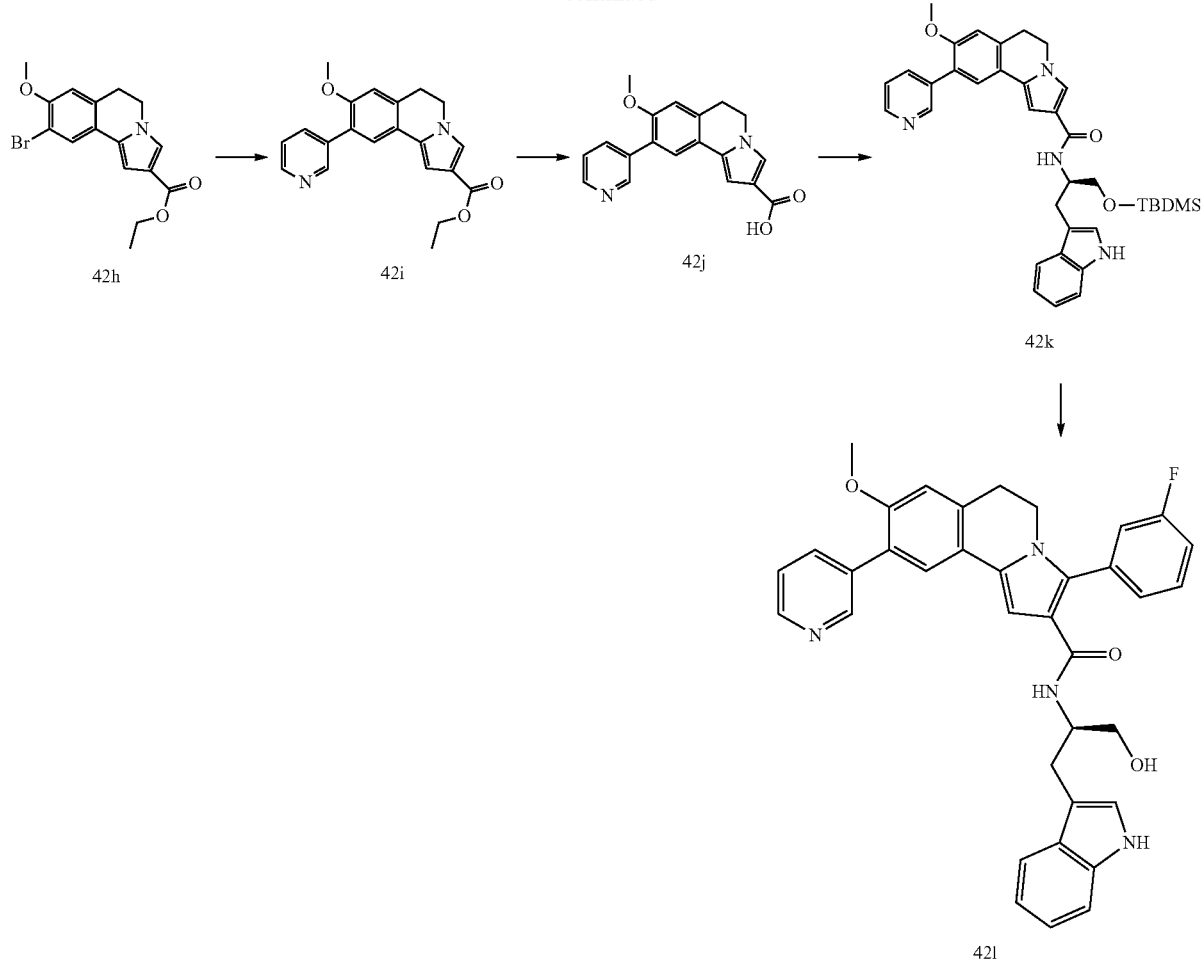

Example 42

(R)-3-(3-fluorophenyl)-N-(1-hydroxy-3-(1H-indol-3-yl)propan-2-yl)-8-methoxy-9-(pyridin-3-yl)-5,6-dihydropyrrolo[2,1-a]isoquinoline-2-carboxamide

(a). 3-Methoxy-4-nitro-benzaldehyde

A mixture of 3-hydroxy-4-nitrobenzaldehyde (51.3 g), iodomethane (38.3 ml) and potassium carbonate (85 g) in DMF (250 ml) was stirred at 60° C. for 1 h. The reaction mixture was cooled to room temperature and poured into water. The solids were collected by filtration and dried in vacuo (50° C.).
Yield: 49.7 g.

(b). 4-Amino-3-methoxy-benzaldyde

Iron (112 g) was added to a mixture of the product of example 42a (49.7 g) and ammonium chloride (103 g) in ethanol (500 ml) and water (500 ml). After stirring with a mechanical stirrer at 78° C. for 2 h, the reaction mixture was cooled to room temperature and extracted with diethyl ether. The combined organic layers were concentrated in vacuo and water was added to the residue. The solids were collected by filtration and dried in vacuo (50° C.).
Yield: 38.3 g.

(c). 4-Bromo-3-methoxy-benzaldehyde

A solution of the product of example 42b (38.3 g) in acetonitrile (600 ml) was added dropwise to a mixture of n-butyl nitrite (43.1 ml) and copper(I) bromide (63.6 g) in acetonitrile (1300 ml). After stirring for 18 h at room temperature, the reaction mixture was diluted with ethyl acetate and washed with an aqueous 1M HCl solution. The organic layer was separated and washed with brine, dried ($MgSO_4$), filtered and concentrated in vacuo. The residue was purified by chromatography on silica gel in heptane/ethyl acetate [1:1 (v/v)].
Yield: 27.4 g.
MS (ESI) m/z: 215, 217 (M+H)$^+$.

(d). 1-Bromo-2-methoxy-4-((E)-2-nitro-vinyl)-benzene

A mixture of the product of example 42c (27.4 g), ammonium acetate (10.8 g) and nitromethane (35 ml) in acetic acid (125 ml) was stirred at 80° C. for 18 h. The reaction mixture was cooled to room temperature and poured into water. The solids were collected by filtration and dissolved in dichloromethane. The organic layer was washed with brine, dried ($MgSO_4$), filtered and concentrated in vacuo.
Yield: 29.8 g.

(e). 2-(4-Bromo-3-methoxy-phenyl)-ethylamine

At 0° C. and under a nitrogen atmosphere a solution of borane-THF complex (262 ml 1 M) was added dropwise to a solution of the product of example 42d (15 g) in THF (250 ml). After the addition, the ice bath was removed. Sodium borohydride (0.11 g) was added (a slight exothermic reaction took place). After stirring for 18 h at 65° C. under a nitrogen atmosphere, the reaction mixture was cooled to room temperature and poured into an aqueous 2M HCl solution. After stirring for 1.5 h at 70° C., the reaction mixture was cooled to room temperature and extracted twice with diethyl ether. The aqueous layer was made basic with solid sodium hydroxide H until pH=10 and extracted three times with ethyl acetate. The combined organic layers were washed with brine, dried (MgSO$_4$), filtered and concentrated in vacuo.

MS (ESI) m/z: 230, 232 (M+H)$^+$.

(f). N-(4-bromo-3-methoxyphenethyl)acetamide

Compound 42e (15.6 g) was dissolved in DCM (200 ml). DIPEA (20.31 ml) was added and acetyl chloride (5.01 ml) was added dropwise at 0° C. under nitrogen atmosphere. The reaction mixture was allowed to warm up to ambient temperature over 1 hour. The reaction mixture was washed sequentially with a aqueous 0.2M HCl solution, a aqueous saturated NaHCO$_3$ solution, water and brine, dried (MgSO$_4$) and filtered. The solvent were removed under vacuum to yield a pale yellow oil which was triturated with diethylether. The solid was filtered and dried to constant mass.

Yield: 14.75 g

(g). 7-bromo-6-methoxy-1-methyl-3,4-dihydroisoquinoline

Phosphorus oxychloride (7.26 g) was added to a solution of compound 42f (5.42 g) in toluene (33 ml) before heating to 110° C. for 2 hours. The solution was allowed to cool to ambient temperature before being concentrated to dryness under vacuum to give a yellow residue. The crude residue was triturated with toluene (2×50 ml) to give product the as a pale yellow solid Yield: 8.13 g $^1$H NMR δ (ppm) (DMSO-d): 8.27 (1H, s), 7.34 (1H, s), 4.04 (3H, s), 3.85-3.77 (2H, m), 3.15-3.06 (2H, m), 2.79 (3H, s).

(h). ethyl 9-bromo-8-methoxy-5,6-dihydropyrrolo[2,1-a]isoquinoline-2-carboxylate Ethyl-3-bromopyruvate (0.87 g) was added to a solution of intermediate 42g (1.0 g), potassium carbonate (5.0 g) and triethylamine (0.72 g) in acetonitrile (20 ml) and then heated to 100° C. for 2 hours. The reaction mixture was allowed to cool to ambient temperature and was then filtered through celite, washing the filter pad thoroughly with acetonitrile. The dark filtrate was concentrated to dryness to give an oil which was partitioned between ethyl acetate (20 ml) and water (20 ml). The organic phase was separated and concentrated to dryness under vacuum to give the product as a pale green oil Yield: 250 mg $^1$H NMR δ (ppm) (CHCl$_3$-d): 7.73 (1H, s), 7.31 (1H, d, J=1.62 Hz), 6.84-6.81 (1H, m), 6.79-6.74 (1H, m), 4.42-4.28 (2H, m), 4.15-4.07 (2H, m), 3.97-3.90 (3H, m), 3.09-3.01 (2H, m), 1.43-1.32 (3H, m).

(i). ethyl 8-methoxy-9-(pyridin-3-yl)-5,6-dihydropyrrolo[2,1-a]isoquinoline-2-carboxylate

[1,1'-Bis(diphenylphosphino)ferrocene]dichloro-palladium(II) (44 mg) was added to a degassed solution of intermediate 42h (200 mg), pyridine-3-boronic acid (104 mg) and potassium carbonate (156 mg) in 9:1 dioxane:water (5.3 ml). The reaction mixture was degassed for 15 minutes with nitrogen before sealing and then heating to 85° C. for 90 minutes. The solvents were removed under vacuum and the residue obtained was partitioned between water and ethyl acetate. The organic phase was concentrated to dryness under vacuum to give a dark oil that was purified by chromatography on silica gel eluting with petrol and increasing amounts of ethyl acetate to give the product as a colourless oil.

Yield: 205 mg $^1$H NMR δ (ppm) (CHCl$_3$-d): 8.81-8.79 (1H, m), 8.58 (1H, dd, J=4.84, 1.67 Hz), 7.88-7.84 (1H, m), 7.63-7.39 (1H, m), 7.38-7.32 (2H, m), 6.85 (2H, d, J=1.97 Hz), 4.38-4.25 (2H, m), 4.17-4.08 (2H, m), 3.84 (3H, s), 3.17-3.10 (2H, m), 1.36 (3H, t, J=7.12 Hz).

(j). 8-methoxy-9-(pyridin-3-yl)-5,6-dihydropyrrolo[2,1-a]isoquinoline-2-carboxylic Acid A aqueous 2N sodium hydroxide solution (1 ml) was added to a solution of intermediate 42i (190 mg) in ethanol (3 ml) and the mixture was then heated to 75° C. for three hours. The solvents were removed under vacuum and the residue obtained was suspended in water (5 ml) and the pH was adjusted to pH 1 with a aqueous 1 N HCl solution. A solid precipitate was filtered, washed with water and dried in air to give the product as an off white solid.

Yield: 148 mg $^1$H NMR δ (ppm) (DMSO-d$_6$): 9.10 (1H, d, J=2.00 Hz), 8.85 (1H, d, J=5.53 Hz), 8.70 (1H, d, J=8.14 Hz), 8.05 (1H, dd, J=8.13, 5.53 Hz), 7.87 (1H, s), 7.49 (1H, d, J=1.65 Hz), 7.22 (1H, s), 6.94 (1H, d, J=1.66 Hz), 4.22-4.15 (2H, m), 3.92-3.87 (3H, m), 3.15 (2H, t, J=6.49 Hz).

(k). (R)—N-(1-(tert-butyldimethylsilyloxy)-3-(1H-indol-3-yl)propan-2-yl)-8-methoxy-9-(pyridin-3-yl)-5,6-dihydropyrrolo[2,1-a]isoquinoline-2-carboxamide 1-Ethyl-3-(3-dimethylaminopropyl)carbodiimide hydrochloride (130 mg) was added to a solution of intermediate 42j (140 mg), 1-hydroxybenzotriazole (64 mg) and diisopropylamine (146 mg) in DMF (1.5 ml). The mixture was stirred for 5 minutes before the addition of 6b (133 mg), stirring for a further 18 hours. The reaction mixture was partitioned between ethyl acetate and water and the aqueous phase was re-extracted with ethyl acetate. The combined organic layers were washed with water and then concentrated to dryness under vacuum to give an orange oil. The crude oil was purified by chromatography on silica gel eluting with petrol and increasing amounts of ethyl acetate to give the product as a white foam.

Yield: 165 mg $^1$H NMR δ (ppm) (CHCl$_3$-d): 8.79 (1H, d, J=2.21 Hz), 8.59 (1H, dd, J=4.82, 1.70 Hz), 8.07 (1H, s), 7.89-7.81 (2H, m), 7.38-7.34 (3H, m), 7.19-7.08 (4H, m), 6.83 (1H, s), 6.40 (1H, d, J=1.76 Hz), 6.12 (1H, d, J=8.52 Hz), 4.47 (1H, dd, J=8.58, 5.31 Hz), 4.15-4.07 (2H, m), 3.84 (3H, s), 3.71 (1H, dd, J=9.85, 2.99 Hz), 3.57 (1H, dd, J=9.86, 5.40 Hz), 3.22-3.05 (4H, m), 0.97 (9H, d, J=1.44 Hz), 0.08 (6H, d, J=7.63 Hz).

(l). (R)-3-(3-fluorophenyl)-N-(1-hydroxy-3-(1H-indol-3-yl)propan-2-yl)-8-methoxy-9-(pyridin-3-yl)-5,6-dihydropyrrolo[2,1-a]isoquinoline-2-carboxamide Palladium (II) acetate (1.9 mg) was added to a degassed solution of intermediate 42k (50 mg), 3-fluoroiodobenzene (26.0 mg), cesium carbonate (58.6 mg) and triphenylphosphine (4.32 mg) in dioxane (3 ml) and the mixture was degassed with nitrogen for a further 15 minutes. The reaction tube was sealed and then heated to 95° C. for 18 hours. The reaction was determined to be incomplete, hence a further aliquot of palladium (II) acetate (1.9 mg), triphenylphosphine (4.32 mg) and 3-fluoroiodobenzene (26.0 mg) were added. The mixture was degassed with nitrogen for 15 minutes, sealed and then heated to 95° C. for 4 hours. The solvents were removed under vacuum and the residue obtained was partitioned between ethyl acetate and water. The aqueous phase was re-extracted with ethyl acetate and the combined organic layers were washed with water and then concentrated to dryness giving a dark brown oil. The oil was redissolved in THF (1 ml) before the addition of tetrabutylammonium fluoride in THF (0.3 ml), stirring for 2 hours. The solvents were removed under vacuum to give a dark oil that was purified by preparative HPLC eluting with acetonitrile and water to give the target compound as a off white solid.

Yield: 3.5 mg $^1$H NMR δ (ppm) (CHCl$_3$-d): 8.81 (1H, s), 8.61 (1H, s), 8.13 (1H, s), 7.89 (1H, d, J=7.90 Hz), 7.61-7.57 (1H, m), 7.43-7.31 (3H, m), 7.16-7.00 (6H, m), 6.93 (1H, d, J=2.23 Hz), 6.82 (1H, s), 6.59 (1H, s), 5.77 (1H, d, J=6.82 Hz), 4.35-4.29 (1H, m), 3.90-3.78 (5H, m), 3.69 (1H, dd, J=10.97, 3.63 Hz), 3.61 (1H, dd, J=10.97, 6.03 Hz), 3.04-2.83 (4H, m), 2.61 (1H, s).

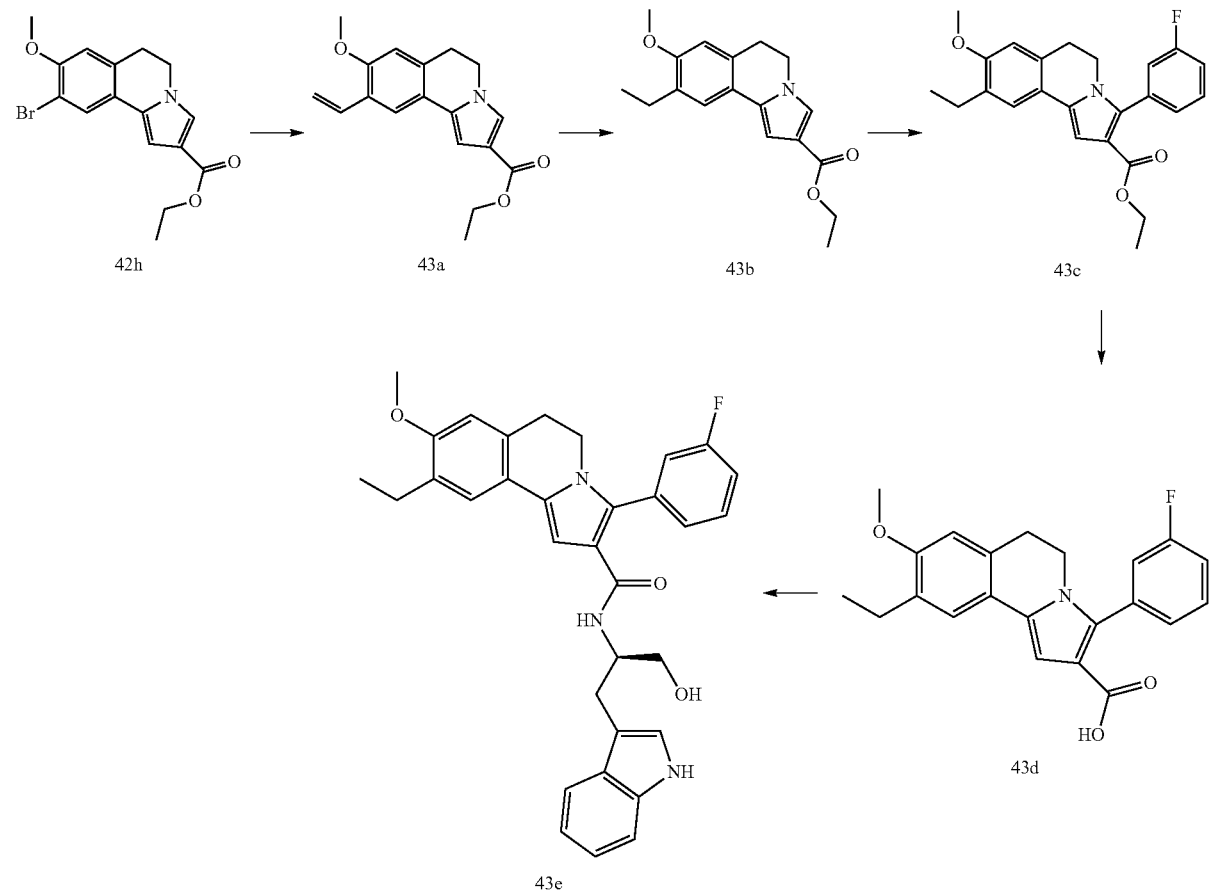

Example 43

(R)-9-ethyl-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide (a). ethyl 8-methoxy-9-vinyl-5,6-dihydropyrrolo[2,1-a]isoquinoline-2-carboxylate Tetrakis(triphenylphosphine)palladium(0) (17 mg) was added to a degassed solution of intermediate 42h (53 mg), vinylboronic acid (41 µl) and potassium carbonate (37 mg) in a 10:1 mixture of DME:water (2 ml). The mixture was degassed by gently bubbling through nitrogen for a further 30 minutes before sealing under nitrogen and then heating to 90° C. for 18 hours. The reaction was allowed to cool to ambient temperature then water was added, extracting with ethyl acetate (3×). The combined organic layers were passed through a hydrophobic frit and concentrated under vacuum to give a dark brown residue. The residue was purified by chromatography on silica gel eluting with petrol and increasing amounts of ethyl acetate to give product the as an orange solid.

Yield: 64 mg $^1$H NMR δ (ppm) (CHCl$_3$-d): 7.63 (1H, s), 7.28 (1H, d, J=1.6 Hz), 7.01 (1H, dd, J=17.8, 11.2 Hz), 6.84 (1H, d, J=1.7 Hz), 6.69 (1H, s), 5.77 (1H, dd, J=17.7, 1.5 Hz), 5.29 (1H, dd, J=11.1, 1.5 Hz), 4.30 (2H, q, J=7.1 Hz), 4.08 (2H, t, J=6.6 Hz), 3.85 (3H, s), 3.05 (2H, t, J 20=6.5 Hz), 1.35 (3H, t, J=7.1 Hz).

(b). ethyl 9-ethyl-8-methoxy-5,6-dihydropyrrolo[2,1-a]isoquinoline-2-carboxylate 10% Palladium on carbon (50 mg) was added to a solution of intermediate 43a (62 mg) in ethanol (5 ml). The reaction vessel was flushed with nitrogen then charged with hydrogen and stirred for 72 hours. The reaction mixture was filtered through celite and the solvent was then removed under vacuum. The residue was dissolved in diethyl ether and washed with water (3×). The organic layer was passed through a hydrophobic frit and then concentrated under vacuum. The residue was purified by chromatography on silica gel eluting with petrol and increasing amounts of ethyl acetate to give the product as a colourless oil/solid.

Yield: 57 mg $^1$H NMR δ (ppm) (CHCl$_3$-d): 7.33 (1H, s), 7.27 (1H, d, J=1.7 Hz), 6.80 (1H, d, J=1.7 Hz), 6.66 (1H, s), 4.29 (2H, q, J=7.1 Hz), 4.07 (2H, t, J=6.6 Hz), 3.83 (3H, s), 3.03 (2H, t, J=6.6 Hz), 2.63 (2H, q, J=7.5 Hz), 1.35 (3H, t, J=7.1 Hz), 1.21 (3H, t, J=7.5 Hz).

(c). ethyl 9-ethyl-3-(3-fluorophenyl)-8-methoxy-5,6-dihydropyrrolo[2,1-a]isoquinoline-2-carboxylate Palladium (II) acetate (4 mg) was added to a degassed solution of intermediate 43b (57 mg), triphenylphosphine (10 mg), 1-fluoro-3-iodobenzene (22 μl) and cesium carbonate (124 mg) in dioxane (2 ml). The mixture was further degassed by bubbling through a gentle stream of nitrogen for 30 minutes. The reaction tube was sealed under nitrogen and then heated to 90° C. for 16 hours. LC-MS analysis indicated the reaction was only ~50% complete, hence the mixture was degassed with nitrogen for 15 minutes before the addition a further aliquot of 1-fluoro-3-iodobenzene (22 μl) and palladium (II) acetate (4 mg). The mixture was degassed for a further 30 minutes before sealing under nitrogen and heating to 100° C. for 24 hours. Water was added and the product was extracted into ethyl acetate (3×). The combined organic layers were passed through a hydrophobic frit and concentrated to dryness under vacuum. The residue was purified by chromatography on silica gel eluting with petrol and increasing amounts of ethyl acetate to give the product as an off white solid.

Yield: 48 mg $^1$H NMR δ (ppm) (CHCl$_3$-d): 7.43-7.39 (2H, m), 7.19 (1H, dt, J=7.7, 1.2 Hz), 7.15-7.08 (2H, m), 6.93 (1H, s), 6.66 (1H, s), 4.16 (2H, q, J=7.1 Hz), 3.87 (2H, t, J=6.5 Hz), 3.84 (3H, s), 2.96 (2H, t, J=6.4 Hz), 2.66 (2H, q, J=7.5 Hz), 1.26-1.15 (6H, m).

(d). 9-ethyl-3-(3-fluorophenyl)-8-methoxy-5,6-dihydropyrrolo[2,1-a]isoquinoline-2-carboxylic Acid Sodium hydroxide (14 mg) in water (0.5 ml) was added to a solution of intermediate 43c (47 mg) in ethanol (5 ml) and the mixture heated to 80° C. for 3 hours. The solvents were removed under vacuum and the residue obtained was redissolved in water (10 ml), washing with diethyl ether. The aqueous phase was acidified to ~pH 4 with a aqueous 4M HCl solution and then extracted with DCM (3×). The combined organic layers were passed through a hydrophobic frit and concentrated to dryness under vacuum to the give product as an off white solid.

Yield: 42 mg $^1$H NMR δ (ppm) (CHCl$_3$-d): 11.00 (1H, s), 7.45-7.37 (2H, m), 7.18 (1H, d, J=7.7 Hz), 7.15-7.07 (2H, m), 6.96 (1H, s), 6.66 (1H, s), 3.91-3.81 (5H, m), 2.96 (2H, t, J=6.4 Hz), 2.65 (2H, dd, J=15.0, 7.5 Hz), 1.22 (3H, t, J=7.5 Hz).

(e). (R)-9-ethyl-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide 1-Ethyl-3-(3-dimethylaminopropyl)carbodiimide hydrochloride (32 mg) was added to a solution of intermediate 43d (40 mg), diisopropylethylamine (58 μl), 1-hydroxybenzotriazole (22 mg), and D-tryptophanol (25 mg) in dry DMF (1 ml), stirring for 70 hours at room temperature. The solvents were removed under vacuum and the residue obtained was partitioned between water and ethyl acetate. The aqueous phase was re-extracted with ethyl acetate (2×) and the combined organic layers were passed through a hydrophobic frit and concentrated to dryness under vacuum. The crude residue was redissolved in MeCN and purified by preparative HPLC eluting with acetonitrile and water to give the target compound as an off white solid Yield: 27 mg MS (ESI) m/z: 538 (M+H)$^+$.

$^1$H NMR δ (ppm) (CHCl$_3$-d): 8.04 (1H, s), 7.59 (1H, d, J=7.9 Hz), 7.37 (1H, d, J=8.1 Hz), 7.31 (1H, s), 7.27-7.19 (2H, m), 7.13 (1H, t, J=7.5 Hz), 7.08-6.96 (3H, m), 6.91 (1H, d, J=2.3 Hz), 6.65 (2H, d, J=8.3 Hz), 5.73 (1H, d, J=6.8 Hz), 4.35-4.28 (1H, m), 3.83 (3H, s), 3.78 (2H, t, J=6.5 Hz), 3.71-3.54 (2H, m), 3.16 (1H, s), 2.98-2.82 (4H, m), 2.66 (2H, q, J=7.5 Hz), 1.23 (3H, t, J=7.5 Hz).

Example 44

3-(3-fluorophenyl)-N—((R)-1-hydroxy-3-(1H-indol-3-yl)propan-2-yl)-8-methoxy-9-(3-methylbutan-2-yl)-5,6-dihydropyrrolo[2,1-a]isoquinoline-2-carboxamide Compound 44 was prepared in an analogous fashion as described for example 43.

$^1$H NMR δ (ppm) (CHCl$_3$-d): 8.00 (1H, s), 7.59 (1H, d, J=7.9 Hz), 7.37 (1H, d, J=8.1 Hz), 7.31 (1H, s), 7.24-7.19 (2H, m), 7.13 (1H, t, J=7.5 Hz), 7.07-6.97 (3H, m), 6.90 (1H, d, J=2.3 Hz), 6.72 (1H, s), 6.65 (1H, s), 5.72 (1H, d, J=6.9 Hz), 4.36-4.29 (1H, m), 3.83-3.74 (5H, m), 3.72-3.57 (2H, m), 3.10 (1H, t, J=5.5 Hz), 2.99-2.83 (5H, m), 1.89-1.82 (1H, m), 1.21 (3H, dd, J=7.1, 3.0 Hz), 0.96 (3H, dd, J=6.7, 2.6 Hz), 0.81 (3H, dd, J=6.7, 3.0 Hz).

Example 45

(R)-3-(3-fluorophenyl)-N-(1-hydroxy-3-(1H-indol-3-yl)propan-2-yl)-8-methoxy-9-(2-methylprop-1-enyl)-5,6-dihydropyrrolo[2,1-a]isoquinoline-2-carboxamide Compound 45 was prepared in an analogous fashion as described for example 43, skipping reaction b ¹H NMR δ (ppm) (CHCl₃-d): 8.11 (1H, s), 7.56 (1H, d, J=7.89 Hz), 7.35 (1H, d, J=8.83 Hz), 6.87 (1H, d, J=2.27 Hz), 6.72 (1H, s), 6.66 (1H, s), 6.29 (1H, s), 5.71 (1H, d, J=6.88 Hz), 4.36-4.27 (1H, m), 3.86-3.73 (5H, m), 3.66 (1H, d, J=10.96), 3.58 (1H, dd, J=10.94, 5.88 Hz), 3.16 (1H, s), 2.98-2.79 (4H, m), 1.97 (3H, s), 1.85 (3H, s)

Example 46

(R)-3-(3-fluorophenyl)-N-(1-hydroxy-3-(1H-indol-3-yl)propan-2-yl)-8-methoxy-9-(3-methyl but-2-en-2-yl)-5,6-dihydropyrrolo[2,1-a]isoquinoline-2-carboxamide Compound 46 was prepared in an analogous fashion as described for example 44, skipping reaction b.

¹H NMR δ (ppm) (CHCl₃-d): 8.02 (1H, s), 7.59 (1H, d, J=7.9 Hz), 7.37 (1H, d, J=8.1 Hz), 7.24-7.10 (4H, m), 7.06-6.98 (3H, m), 6.92 (1H, d, J=2.3 Hz), 6.69 (1H, s), 6.58 (1H, s), 5.73 (1H, d, J=6.8 Hz), 4.32-4.27 (1H, m), 3.82-3.78 (5H, m), 3.70-3.56 (2H, m), 3.20-3.10 (1H, s), 2.97-2.82 (4H, m), 1.94 (3H, s), 1.87 (3H, s), 1.55 (3H, s)

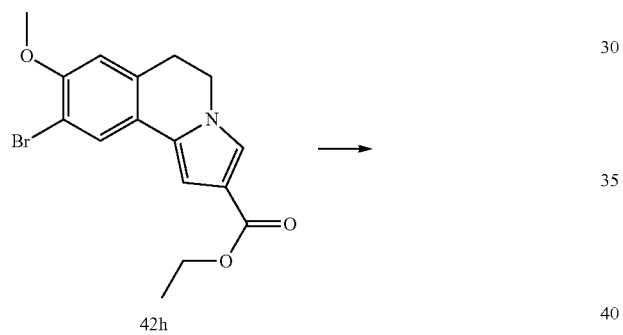

42h

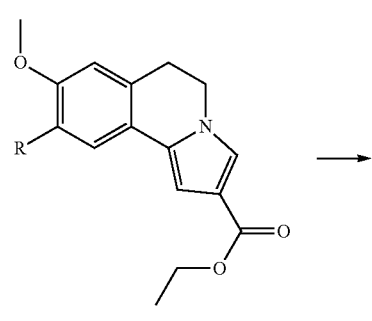

47a

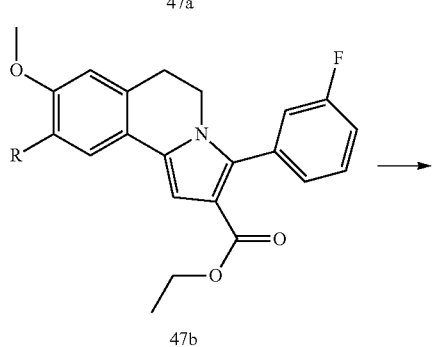

47b

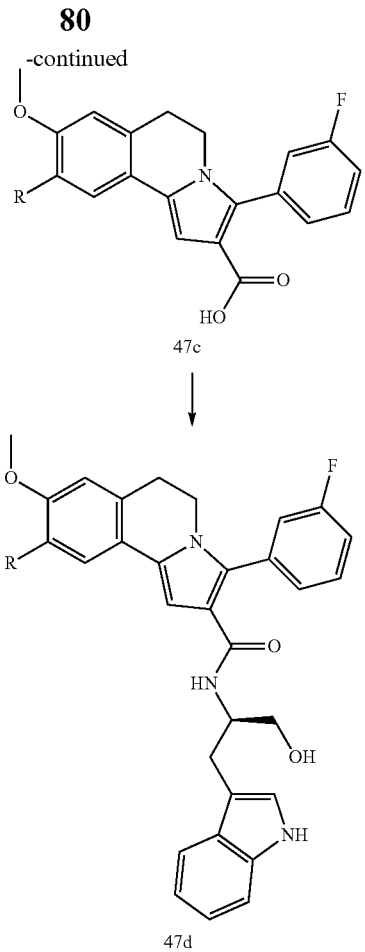

47. R = <sub>*</sub>—C(=O)—N(morpholine)

48. R = <sub>*</sub>—C(=O)—N(CH₃)₂

Example 47

(R)-3-(3-fluorophenyl)-N-(1-hydroxy-3-(1H-indol-3-yl)propan-2-yl)-8-methoxy-9-(morpholine-4-carbonyl)-5,6-dihydropyrrolo[2,1-a]isoquinoline-2-carboxamide (a). ethyl 8-methoxy-9-(morpholine-4-carbonyl)-5,6-dihydropyrrolo[2,1-a]isoquinoline-2-carboxylate A mixture of compound 42h (105 mg), morpholine (39 μl), xantphos (35 mg), palladium (II) acetate (6.7 mg) and sodium carbonate (48 mg) in toluene (2 ml) was saturated with carbon monoxide by bubbling gas through it for 20 minutes. The mixture was then heated at 80° C. overnight. The reaction mixture was diluted with water and the extracted with ethyl acetate (3×). The combined organic layers were passed through a hydrophobic frit and concentrated in vacuo. The residue was purified by chromatography on silica gel eluting with DCM containing increasing amounts of methanol.

Yield: 90 mg

(b). ethyl 3-(3-fluorophenyl)-8-methoxy-9-(morpholine-4-carbonyl)-5,6-dihydropyrrolo[2,1-a]isoquinoline-2-carboxylate Palladium (II) acetate (5.2 mg) was added to a degassed solution of intermediate 47a (88 mg), triphenylphosphine (12 mg), 1-fluoro-3-iodobenzene (27 μl) and cesium carbonate (150 mg) in dioxane (2 ml). The mixture was further degassed by bubbling through a gentle stream of nitrogen for 30 minutes. The reaction tube was sealed under nitrogen and then heated to 80° C. for 16 hours. LC-MS analysis indicated the reaction was ~50% complete, hence the mixture was degassed with nitrogen for 15 minutes before the addition a further aliquot of 1-fluoro-3-iodobenzene (22 μl) and palladium (II) acetate (4 mg). The mixture was degassed for a further 30 minutes before sealing under nitrogen and heating to 80° C. for 4 hours. Water was added and the product was extracted into ethyl acetate (3×). The combined organic layers were passed through a hydrophobic frit and concentrated to dryness under vacuum. The residue was purified by chromatography on silica gel eluting with petrol and increasing amounts of ethyl acetate to give the product, as an off white solid.

Yield: 48 mg

(c). 3-(3-fluorophenyl)-8-methoxy-9-(morpholine-4-carbonyl)-5,6-dihydropyrrolo[2,1-a]isoquinoline-2-carboxylic Acid A aqueous 2N sodium hydroxide solution (0.5 ml) was added to a solution of intermediate 47b (31 mg) in ethanol (2 ml) and the mixture heated to 50° C. for 18 hours. The reaction mixture was acidified with a aqueous solution of 2M HCl and was extracted with ethyl acetate. The organic layer was washed with water and dried by passing through a hydrophobic frit and concentrated in vacuo, to yield an off-white powder.

Yield: 29.6 mg

(d). (R)-3-(3-fluorophenyl)-N-(1-hydroxy-3-(1H-indol-3-yl)propan-2-yl)-8-methoxy-9-(morpholine-4-carbonyl)-5,6-dihydropyrrolo[2,1-a]isoquinoline-2-carboxamide 1-Ethyl-3-(3-dimethylaminopropyl)carbodiimide hydrochloride (19 mg) was added to a solution of intermediate 47c (30 mg), triethylamine (27 μl), 1-hydroxybenzotriazole (9.3 mg), and D-tryptophanol (15 mg) in dry DMF (1 ml), stirring for 70 hours at room temperature. The solvents were removed under vacuum and the residue obtained was partitioned between water and ethyl acetate. The aqueous phase was re-extracted with ethyl acetate (2×) and the combined organics were passed through a hydrophobic frit and concentrated to dryness under vacuum. The residue was purified by chromatography on silica gel eluting with DCM and increasing amounts of methanol (max. 10%). The pure fractions were collected, yielding in the desired product as an off-white solid.

Yield: 17 mg $^{1}$H NMR δ (ppm) (CHCl$_3$-d): 8.14 (1H, s), 7.59 (1H, d, J=7.86 Hz), 7.42-7.35 (2H, m), 7.21-7.10 (3H, m), 7.09-7.00 (4H, m), 6.94 (1H, s), 6.73 (1H, s), 6.58 (1H, s), 5.80-5.69 (1H, m), 4.31 (1H, s), 3.89-3.74 (6H, m), 3.68 (2H, s), 3.62 (1H, s), 3.31 (2H, s), 3.18 (1H, d, J=14.81), 3.02-2.83 (4H, m)

Example 48

(R)-3-(3-fluorophenyl)-N2-(1-hydroxy-3-(1H-indol-3-yl)propan-2-yl)-8-methoxy-N9,N9-dimethyl-5,6-dihydropyrrolo[2,1-a]isoquinoline-2,9-dicarboxamide Compound 48 was prepared in an analogous fashion as described for example 47.

$^{1}$H NMR δ (ppm) (CHCl$_3$-d): 8.16 (1H, s), 7.58 (1H, d, J=7.89 Hz), 7.40-7.31 (2H, m), 7.21 (1H, s), 7.15-6.99 (4H, m), 6.94 (1H, d, J=2.29 Hz), 6.73-6.68 (1H, m), 6.53 (1H, s), 5.77 (1H, d, J=6.61 Hz), 4.30 (1H, t, J=6.40 Hz), 3.86-3.75 (4H, m), 3.72-3.65 (2H, m), 3.63-3.56 (1H, m), 3.25 (1H, s), 3.20-3.14 (3H, m), 2.99-2.82 (6H, m)

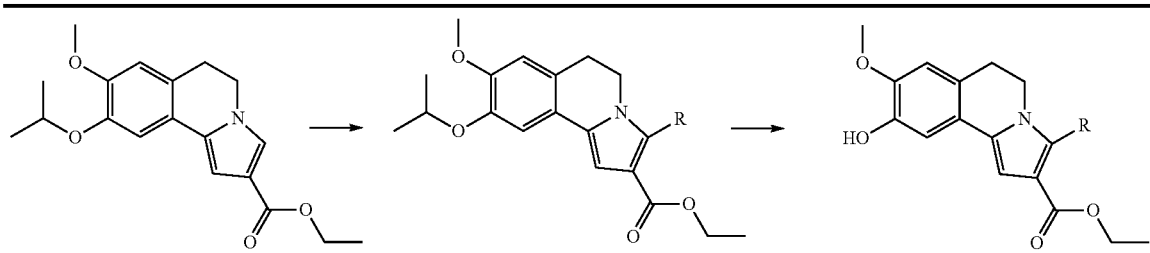

2b         49a         49b

-continued
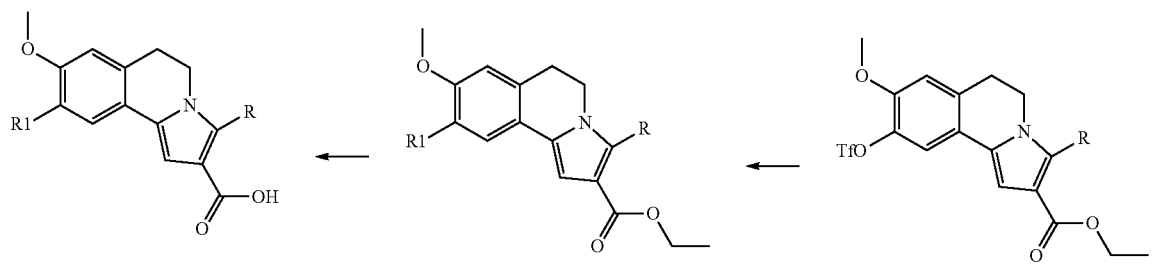
49e 49d 49c
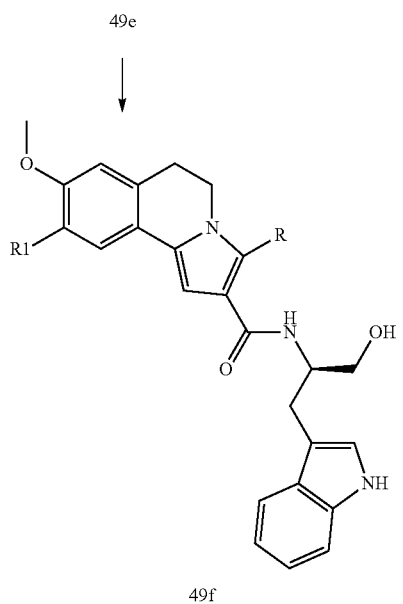
49f
| | R = 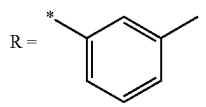 | 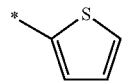 |
|---|---|---|
| R1 = 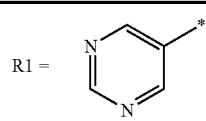 | 50 | 49 |
| 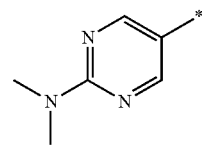 [SMILES: *c1cnc(N(C)C)nc1] | 51 | 56 |
| 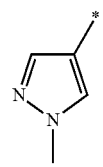 [SMILES: *c1cnn(C)c1] | 52 | 55 |
| 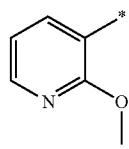 [SMILES: *c1cccnc1OC] | 53 | 54 |

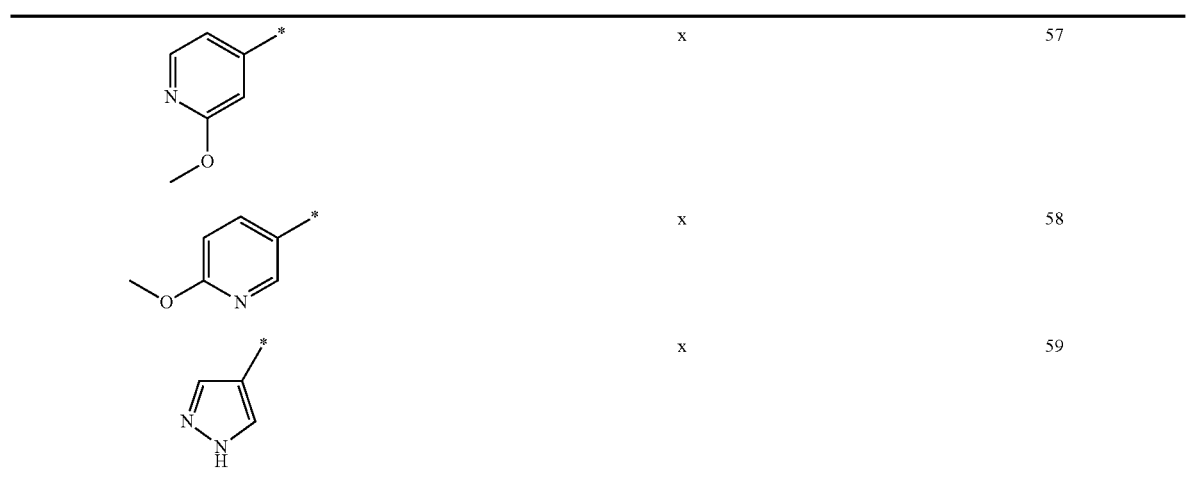

| | x | 57 |
| | x | 58 |
| | x | 59 |

Example 49

(R)—N-(1-hydroxy-3-(1H-indol-3-yl)propan-2-yl)-8-methoxy-9-(pyrimidin-5-yl)-3-(thiophen-2-yl)-5,6-dihydropyrrolo[2,1-a]isoquinoline-2-carboxamide (a). ethyl 9-isopropoxy-8-methoxy-3-(thiophen-2-yl)-5,6-dihydropyrrolo[2,1-a]isoquinoline-2-carboxylate To a solution of compound 2b (1 g) in dioxane (20 ml) were added 2-bromothiophene (775 mg), triphenylphosphine (180 mg) and cesium carbonate (2.06 g). The reaction mixture was degassed for 10 minutes under $N_2$. Then palladium(II) acetate (80 mg) was added and the mixture was degassed for another 10 minutes under $N_2$. The reactant was heated under reflux for 20 hours. The mixture was cooled to room temperature, diluted with ethyl acetate and filtered. The filtrate was washed with water and brine. The organic layer was dried over anhydrous $Na_2SO_4$, filtered and concentrated to give the crude product which was purified by chromatography on silica gel (petrol:ethyl acetate=10:1-6:1) to give the desired product Yield: 550 mg MS (ESI) m/z: 412 $(M+H)^+$.

(b). ethyl 9-hydroxy-8-methoxy-3-(thiophen-2-yl)-5,6-dihydropyrrolo[2,1-a]isoquinoline-2-carboxylate To a solution of compound 49a (282 mg) in DCM (7 ml) was added aluminium chloride (365 mg) at 0° C. The reaction mixture was stirred at 0° C. for 2 hours. The reaction mixture was washed with water and DCM phase was dried over anhydrous $Na_2SO_4$, filtered and concentrated to give the desired compound the desired product.

Yield: 230 mg

MS (ESI) m/z: 370 $(M+H)^+$.

$^1$H NMR δ (ppm) ($CHCl_3$-d): 8.99 (s, 1H), 7.74-7.75 (m, 1H), 7.20-7.22 (m, 1H), 7.17-7.19 (m, 1H), 7.05 (s, 1H), 6.86 (s, 1H), 6.77 (s, 1H), 4.04-4.09 (m, 2H), 3.87 (t, 2H, J=6.6 Hz), 3.78 (s, 3H), 2.89 (t, 2H, J=6.6 Hz), 1.13 (t, 2H, J=7.0 Hz).

(c). ethyl 8-methoxy-3-(thiophen-2-yl)-9-(trifluoromethylsulfonyloxy)-5,6-dihydropyrrolo[2,1-a]isoquinoline-2-carboxylate To a solution of compound 49b (20 mg) in DCM (2 ml) were added trifluoromethanesulfonic anhydride (16.8 mg) and pyridine (6.4 mg). The reaction mixture was stirred at ambient temperature for 2 hours. The reaction mixture was washed with water, and the DCM phase was dried over anhydrous $Na_2SO_4$, filtered and concentrated to give the desired compound.

Yield: 23 mg

MS (ESI) m/z: 502 $(M+H)^+$.

1HNMR (CDCl3 400 MHz) 7.39 (s, 1H) 7.26 (s, 1H), 7.08 (s, 1H), 7.01 (s, 1H), 6.92 (s, 1H), 6.87 (s, 1H), 4.19 (m, 2H), 3.98 (t, 2H, J=6.56 Hz), 3.92 (s, 3H), 3.01 (t, 2H, J=6.63 Hz), 1.29 (d, 5H, J=6.94 Hz), 1.21 (t, 4H, J=7.17 Hz).

(d). ethyl 8-methoxy-9-(pyrimidin-5-yl)-3-(thiophen-2-yl)-5,6-dihydropyrrolo[2,1-a]isoquinoline-2-carboxylate To a solution of compound 49c (40 mg) in dioxane/water (5 ml/0.5 ml) was added pyrimidin-5-ylboronic acid (11.8 mg), (tetrakis(triphenylphosphine)palladium(0) (11 mg) and $Na_2CO_3$ (10 mg). The reaction mixture was heated to reflux for 2 hours. The mixture was cooled to room temperature and diluted with ethyl acetate and filtered. The filtrate was washed with water and brine. The ethyl acetate layer was dried over anhydrous $Na_2SO_4$, filtered and concentrated to give the crude product which was purified by chromatography on silica gel (petrol:ethyl acetate=6:1→3:1) to give the desired product.

Yield: 30 mg

MS (ESI) m/z: 432 $(M+H)^+$.

$^1$H NMR δ (ppm) ($CHCl_3$-d): 9.18 (s, 1H), 8.94 (s, 2H), 7.64-7.69 (m, 6H), 7.53-7.57 (m, 4H), 7.44-7.48 (m, 8H), 7.25 (s, 1H), 7.13-7.15 (m, 2H), 6.97 (s, 1H), 6.86 (s, 1H), 4.15-4.21 (m, 2H), 4.00 (t, 2H, J=6.6 Hz), 3.86 (s, 3H), 3.07 (t, 2H, J=6.5 Hz), 1.22 (t, 3H, J=7.1 Hz).

(e). 8-methoxy-9-(pyrimidin-5-yl)-3-(thiophen-2-yl)-5,6-dihydropyrrolo[2,1-a]isoquinoline-2-carboxylic Acid To a solution of compound 49d (25 mg) in methanol (2 ml) was added aqueous sodium hydroxide solution (0.5 ml, wt 9%). The reaction mixture was heated to 40° C. for 2 hours. The reaction mixture was acidified with a aqueous 2N HCl solution (3 ml) to pH=2 and extracted with ethyl acetate, the organic phase was dried over anhydrous Na$_2$SO$_4$, filtered and concentrated to give the desired compound.

Yield: 14 mg

MS (ESI) m/z: 404 (M+H)$^+$.

(f). (R)—N-(1-hydroxy-3-(1H-indol-3-yl)propan-2-yl)-8-methoxy-9-(pyrimidin-5-yl)-3-(thiophen-2-yl)-5,6-dihydropyrrolo[2,1-a]isoquinoline-2-carboxamide To a solution of compound 49e (14 mg) in DMF (2 ml) were added tryptophanol (9 mg), triethylamine (12 mg) and HATU (15 mg). Then the reaction mixture was stirred at ambient temperature for 2 hours. The reaction mixture was diluted with water and extracted into ethyl acetate. The organic phase was dried over anhydrous Na$_2$SO$_4$, filtered and concentrated to give the crude product which was purified by preparative HPLC, with acetonitrile and water as eluens to give the desired product.

Yield: 11 mg

LCMS (EI) (M+H)$^+$ 576

$^1$H NMR δ (ppm) (CHCl$_3$-d): 9.20 (s, 1H), 8.98 (s, 2H), 8.05 (s, 1H), 7.55 (d, 1H, J=7.8 Hz), 7.46 (s, 1H), 7.38 (m, 2H), 7.08-7.18 (m, 2H), 6.94-6.95 (m, 3H), 6.82 (d, 2H, J=9.1 Hz), 5.91 (d, 1H, J=6.9 Hz), 4.33 (s, 1H), 3.86 (s, 2H), 3.85 (s, 3H), 3.66-3.70 (m, 1H), 3.55-3.59 (m, 1H), 3.04 (t, 2H, J=6.5 Hz), 2.77-2.91 (m, 2H)

Example 50

(R)-3-(3-fluorophenyl)-N-(1-hydroxy-3-(1H-indol-3-yl)propan-2-yl)-8-methoxy-9-(pyrimidin-5-yl)-5,6-dihydropyrrolo[2,1-a]isoquinoline-2-carboxamide Compound 50 was prepared in analogous fashion as described for example 49.

MS (ESI) m/z: 588 (M+H)$^+$.

$^1$H NMR δ (ppm) (CHCl$_3$-d): 9.23 (s, 1H), 9.00 (s, 2H), 8.14 (s, 1H), 7.58 (d, 1H, J=7.2 Hz), 7.42 (s, 1H), 7.36 (d, 1H, J=7.4 Hz), 7.03-7.16 (m, 5H), 6.95 (s, 1H), 6.85 (s, 1H), 6.60 (s, 1H), 5.81 (d, 1H, J=6.3 Hz), 4.31-4.32 (m, 1H), 3.86 (s, 3H), 3.85 (s, 2H), 3.69-3.72 (m, 1H), 3.59-3.64 (m, 1H), 3.03 (t, 2H, J=6.3 Hz), 2.85-2.99 (m, 2H).

Example 51

(R)-9-(2-(dimethylamino)pyrimidin-5-yl)-3-(3-fluorophenyl)-N-(1-hydroxy-3-(1H-indol-3-yl)propan-2-yl)-8-methoxy-5,6-dihydropyrrolo[2,1-a]isoquinoline-2-carboxamide Compound 51 was prepared in an analogous fashion as described for example 49.

MS (ESI) m/z: 631 (M+H)$^+$.

$^1$H NMR δ (ppm) (CHCl$_3$-d): 9.24 (s, 1H), 8.85 (s, 2H), 7.58 (d, 1H, J=7.4 Hz), 7.38 (d, 1H, J=8.3 Hz), 7.29-7.33 (m, 2H), 7.03-7.15 (m, 6H), 6.81 (s, 1H), 6.28 (s, 1H), 5.96 (d, 1H, J=4.7 Hz), 4.28 (s, 1H), 3.86 (s, 3H), 3.76-3.83 (m, 2H), 3.63-3.67 (m, 2H), 3.43 (s, 6H), 3.03-3.08 (m, 1H), 2.99 (t, 2H, J=5.5 Hz), 2.85-2.91 (m, 1H).

Example 52

(R)-3-(3-fluorophenyl)-N-(1-hydroxy-3-(1H-indol-3-yl)propan-2-yl)-8-methoxy-9-(1-methyl-1H-pyrazol-4-yl)-5,6-dihydropyrrolo[2,1-a]isoquinoline-2-carboxamide Compound 52 was prepared in analogous fashion as described for example 49.

MS (ESI) m/z: 590 (M+H)$^+$.

$^1$H NMR δ (ppm) (CHCl$_3$-d): 8.16 (s, 1H), 8.01 (s, 1H), 7.87 (s, 1H), 7.61 (s, 1H), 7.58 (d, 1H, J=8.1 Hz), 7.39 (d, 1H, J=8.0 Hz), 7.20 (t, 1H J=8.0 Hz), 7.13 (t, 1H, J=8.0 Hz), 7.01-7.07 (m, 3H), 6.95 (s, 1H), 6.77 (s, 1H), 6.66 (s, 1H), 5.85 (d, 1H, J=6.8 Hz), 4.33-4.36 (m, 1H), 4.02 (s, 3H), 3.92 (s, 3H), 3.81 (t, 2H, J=6.6 Hz), 3.70-3.74 (m, 1H), 3.60-3.64 (m, 1H), 2.94-2.99 (m, 3H), 2.85-2.91 (m, 1H).

Example 53

3-(3-fluorophenyl)-N—((R)-1-hydroxy-3-(1H-indol-3-yl)propan-2-yl)-8-methoxy-9-(2-methoxypyridin-3-yl)-5,6-dihydropyrrolo[2,1-a]isoquinoline-2-carboxamide Compound 53 was prepared in analogous fashion as described for example 49.

MS (ESI) m/z: 617 (M+H)$^+$.

$^1$H NMR δ (ppm) (CHCl$_3$-d): 8.20-8.22 (m, 1H), 8.01 (s, 1H), 7.57 (d, 2H, J=5.5 Hz), 7.39 (s, 1H), 7.33 (t, 1H, J=5.4 Hz), 6.97-7.10 (m, 6H), 6.90 (s, 1H), 6.79 (s, 1H), 6.59 (s, 1H), 5.72 (d, 1H, J=5.4 Hz), 4.29-4.31 (m, 1H), 3.95 (s, 3H), 3.83 (t, 2H, J=5.4 Hz), 3.78 (s, 3H), 3.66-3.69 (m, 1H), 3.57-3.61 (m, 1H), 3.14-3.15 (m, 1H), 3.00 (t, 2H, J=6.5 Hz), 2.82-3.01 (m, 2H).

Example 54

N—((R)-1-hydroxy-3-(1H-indol-3-yl)propan-2-yl)-8-methoxy-9-(2-methoxypyridin-3-yl)-3-(thiophen-2-yl)-5,6-dihydropyrrolo[2,1-a]isoquinoline-2-carboxamide Compound 54 was prepared in analogous fashion as described for example 49.

MS (ESI) m/z: 605 (M+H)$^+$.

$^1$H NMR δ (ppm) (CHCl$_3$-d): 10.73 (s, 1H), 8.17-8.18 (m, 1H), 7.56-7.67 (m, 3H), 7.36 (s, 1H), 7.28 (d, 1H, J=7.6 Hz), 7.11-7.13 (m, 1H), 7.02-7.06 (m, 5H), 6.92-6.98 (m, 1H), 6.84 (s, 1H), 4.03-4.07 (m, 1H), 3.89 (t, 2H, J=6.0 Hz), 3.82 (s, 3H), 3.73 (s, 3H), 3.02 (t, 2H, J=6.0 Hz (s, 1H), 2.84-2.89 (m, 1H), 2.70-2.75 (m, 1H).

Example 55

(R)—N-(1-hydroxy-3-(1H-indol-3-yl)propan-2-yl)-8-methoxy-9-(1-methyl-1H-pyrazol-4-yl)-3-(thiophen-2-yl)-5,6-dihydropyrrolo[2,1-a]isoquinoline-2-carboxamide Compound 55 was prepared in analogous fashion as described for example 49.

MS (ESI) m/z: 578 (M+H)$^+$.

¹H NMR δ (ppm) (CHCl₃-d): 10.74 (s, 1H), 8.12 (s, 1H), 7.94 (s, 1H), 7.78 (s, 1H), 7.65-7.66 (m, 1H), 7.56 (d, 1H, J=8 Hz), 7.29 (d, 1H, J=8.0 Hz), 7.13 (s, 2H), 7.05 (s, 5H), 7.00 (s), 6.89 (d, 1H, J=8.3 Hz), 4.09-4.11 (m, 1H), 3.88 (s, 8H), 3.38-3.42 (m, 2H), 3.28-3.32 (m, 2H), 2.98 (t, 2H, J=5.6 Hz), 2.88-2.94 (m, 1H), 2.74-2.79 (m, 1H).

Example 56

(R)-9-(2-(dimethylamino)pyrimidin-5-yl)-N-(1-hydroxy-3-(1H-indol-3-yl)propan-2-yl)-8-methoxy-3-(thiophen-2-yl)-5,6-dihydropyrrolo[2,1-a]isoquinoline-2-carboxamide Compound 56 was prepared in analogous fashion as described for example 49.
MS (ESI) m/z: 619 (M+H)⁺.
¹H NMR δ (ppm) (CHCl₃-d): 10.74 (s, 1H), 8.51 (s, 1H), 7.66 (d, 1H, J=3.6 Hz), 7.56 (d, 1H, J=8.4 Hz), 7.51 (s, 1H), 7.28 (d, 1H, J=7.8 Hz), 7.11 (s, 1H), 6.98-7.05 (m, 2H), 6.88-6.94 (m, 2H), 4.05-4.07 (m, 1H), 3.86 (t, 2H, J=6.0 Hz), 3.77 (s, 3H), 3.35-3.39 (m, 2H), 3.25-3.29 (m, 2H), 3.14 (s, 5H), 2.98 (t, 1H, J=5.7), 2.86-2.90 (m, 1H), 2.71-2.76 (m, 1H).

Example 57

(R)—N-(1-hydroxy-3-(1H-indol-3-yl)propan-2-yl)-8-methoxy-9-(2-methoxypyridin-4-yl)-3-(thiophen-2-yl)-5,6-dihydropyrrolo[2,1-a]isoquinoline-2-carboxamide Compound 57 was prepared in analogous fashion as described for example 49.
MS (ESI) m/z: 605 (M+H)⁺.
¹H NMR δ (ppm) (CHCl₃-d): 8.33 (s, 1H), 8.17 (s, 1H), 7.52-7.55 (m, 2H), 7.34-7.39 (m, 2H), 6.013 (s, 1H), 7.28 (s, 1H), 7.07-7.18 (m, 3H), 6.89-6.94 (m, 3H), 6.83 (s, 1H), 5.97 (d, 1H, J=7.0 Hz), 4.30-4.39 (m, 1H), 4.09 (s, 3H), 3.81-3.85 (m, 8H), 3.66-3.68 (m, 1H), 3.57-3.58 (m, 1H), 3.03 (s, 2H), 2.76-2.90 (m, 2H).

Example 58

(R)—N-(1-hydroxy-3-(1H-indol-3-yl)propan-2-yl)-8-methoxy-9-(6-methoxypyridin-3-yl)-3-(thiophen-2-yl)-5,6-dihydropyrrolo[2,1-a]isoquinoline-2-carboxamide Compound 58 was prepared in analogous fashion as described for example 49.
MS (ESI) m/z: 605 (M+H)⁺.
¹H NMR δ (ppm) (CHCl₃-d): 8.50 (s, 1H), 8.33 (s, 1H), 7.99 (d, 1H, J=6.8 Hz), 7.55 (d, 1H, J=6.9 Hz), 7.35-7.44 (m, 3H), 7.08-7.17 (m, 2H), 6.96 (d, 3H, J=3.8 Hz), 6.80 (s, 1H), 6.73 (s, 1H), 5.99 (s, 1H), 4.30-4.37 (m, 1H), 4.08 (s, 3H), 3.84-3.87 (m, 5H), 3.70 (s, 1H), 3.48-3.70 (m, 9H), 3.02 (s, 2H), 2.91-2.95 (m, 1H), 2.80-2.84 (m, 1H).

Example 59

(R)—N-(1-hydroxy-3-(1H-indol-3-yl)propan-2-yl)-8-methoxy-9-(1H-pyrazol-4-yl)-3-(thiophen-2-yl)-5,6-dihydropyrrolo[2,1-a]isoquinoline-2-carboxamide Compound 59 was prepared in analogous fashion as described for example 49.
¹H NMR δ (ppm) (CHCl₃-d): 8.12 (s, 1H), 8.06 (s, 1H), 7.70 (s, 1H), 7.57 (d, 1H, J=7.2 Hz), 7.36-7.39 (m, 2H), 7.20 (t, 1H J=8 Hz), 7.12 (t, 1H, J=6.9 Hz), 6.92-6.96 (m, 4H), 6.79 (s, 1H), 5.90 (d, 1H, J=7.6 Hz), 4.34-4.38 (m, 1H), 3.92 (s, 3H), 3.85 (t, 2H, J=6.4 Hz), 3.67-3.71 (m, 1H), 3.56-3.59 (m, 1H), 3.00 (t, 2H, J=6.2 Hz), 2.78-2.92 (m, 2H).

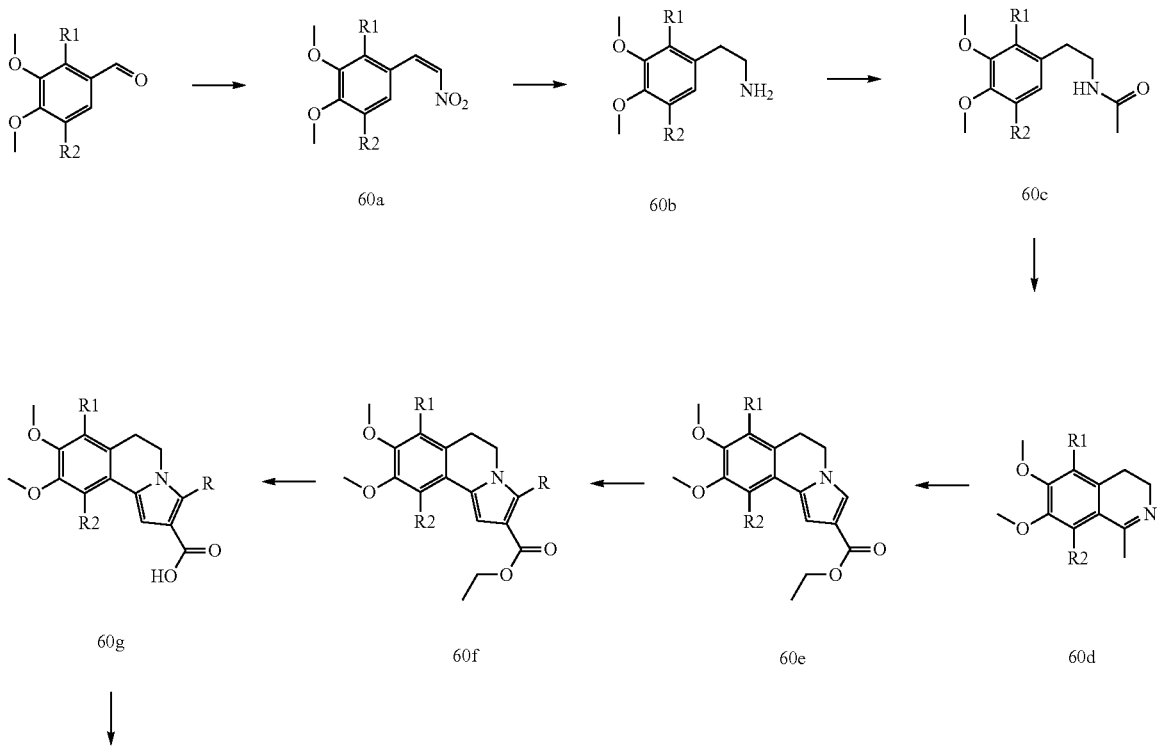

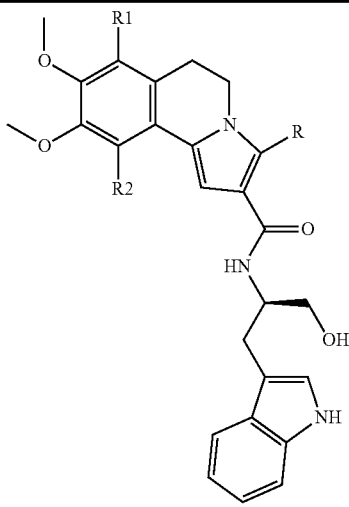

60h

| R | R1 = OMe, R2 = H | R1 = H, R2 = OMe |
|---|---|---|
| *⟨phenyl⟩ | 60. | 63. |
| *⟨2-thienyl⟩ | 61. | 64. |
| *⟨3-fluorophenyl⟩ | 62. | 65. |

Example 60

(R)—N-(1-hydroxy-3-(1H-indol-3-yl)propan-2-yl)-7,8,9-trimethoxy-3-phenyl-5,6-dihydropyrrolo[2,1-a]isoquinoline-2-carboxamide (a). (Z)-1,2,3-trimethoxy-4-(2-nitrovinyl)benzene 2,3,4-trimethoxybenzaldehyde (20 g) was dissolved in nitromethane (50 ml). Ammonium acetate (8.25 g) was added, and the reaction was heated to 50° C. for 2 hrs. The solvents were evaporated in vacuo. The orange residue was partitioned between water and DCM. The organic layer was washed with brine, dried over $Na_2SO_4$ filtered and concentrated in vacuo.

Yield: 26.3 g (b/c). N-(2,3,4-trimethoxyphenethyl)acetamide

Lithium aluminium hydride, 2.4M in THF (69.7 ml) was diluted with tetrahydrofuran (dry) (400 ml), and heated to 65° C. in a three-necked flask under a N2 atmosphere. To this hot solution was added dropwise a solution of compound 60a (10 g) in tetrahydrofuran (dry) (150 ml), maintaining a gentle reflux, over the course of 2 hours. After addition was complete, reflux was continued for 1 h. The reaction mixture was cooled to 0° C. in an ice bath, and then the excess lithium aluminium hydride quenched by portionwise addition of sodium sulfate decahydrate (53.9 g). After quenching, ~10 g anhydrous sodium sulfate was added, the reaction mixture stirred for 15 minutes, and then filtered over a Celite pad and the solvents evaporated, yielding 7.7 g clear yellow oil. The intermediate was dissolved in acetic anhydride (39.4 ml), sodium bicarbonate (3.51 g) was added and the solution stirred at room temperature for 36 hours. The reaction mixture was poured into water, and extracted with DCM twice. The combined organics were washed with a aqueous saturated $NaHCO_3$ solution, brine, then dried over $Na_2SO_4$ and concentrated in vacuo. The product was purified using chromatography on silica gel, methanol/DCM 1/99>7/93 gradient. The compound slowly crystallizes on standing.

Yield: 3.97 g (d). 5,6,7-trimethoxy-1-methyl-3,4-dihydroisoquinoline

To a solution of compound 60c (1.8 g) in toluene (10 ml) was added dropwise phosphorus oxychloride (0.2 ml) under nitrogen atmosphere at 90° C., over a period of 1 hour. The mixture was heated at 120° C. for 2 hours and allowed to cool to room temperature overnight. The resulting HCl salt was collected by filtration and washed with ether to give the product as a brown solid Yield: 2.2 g

(e). ethyl 7,8,9-trimethoxy-5,6-dihydropyrrolo[2,1-a]isoquinoline-2-carboxylate To a mixture of 63d (2.1 g) and potassium carbonate (3.7 g) in acetonitrile (15 ml) was added dropwise ethylbromopyruvate (1.6 g). The reaction mixture was refluxed for 2 hours. The reaction was allowed to cool to ambient temperature before a saturated aqueous NaHCO₃ solution was added. The aqueous phase was extracted with ethyl acetate twice. The combined organic layers were washed with brine. The organic layer was dried (MgSO₄), filtered and concentrated in vacuo. The residue was purified by chromatography on silica gel eluting with petrol and increasing amounts of ethyl acetate. The pure fractions of the desired product were concentrated in vacuo.

Yield: 0.9 g

(f). ethyl 7,8,9-trimethoxy-3-phenyl-5,6-dihydropyrrolo[2,1-a]isoquinoline-2-carboxylate Palladium (II) acetate (7.5 mg) was added to a degassed solution of intermediate 60e (150 mg), triphenylphosphine (20 mg), phenylbromide (27 µl) and cesium carbonate (200 mg) in dioxane (2 ml). The mixture was further degassed by bubbling through a gentle stream of nitrogen for 30 minutes. The reaction tube was sealed under nitrogen and then heated to 80° C. for 16 hours. LC-MS analysis indicated the reaction was ~50% complete, hence the mixture was degassed with nitrogen for 15 minutes before the addition a further aliquot of 1-fluoro-3-iodobenzene (22 µl) and palladium (II) acetate (4 mg). The mixture was degassed for a further 30 minutes before sealing under nitrogen and heating to 80° C. for 4 hours. Water was added and the product was extracted into ethyl acetate (3×). The combined organic layers were passed through a hydrophobic frit and concentrated to dryness under vacuum. The residue was purified by chromatography on silica gel eluting with heptane and increasing amounts of ethyl acetate.

Yield: 90 mg

(g). 7,8,9-trimethoxy-3-phenyl-5,6-dihydropyrrolo[2,1-a]isoquinoline-2-carboxylic Acid A aqueous solution of 2M sodium hydroxide (0.75 ml) was added to a solution of intermediate 60f (90 mg) in ethanol (2 ml) and the mixture heated to 50° C. for 18 hours. The reaction mixture was acidified with a aqueous solution of 2M HCl and was extracted with ethyl acetate. The organic layer was washed with water and dried by passing through a hydrophobic frit and concentrated in vacuo, to yield an off-white powder.

Yield: 93 mg

(h). (R)—N-(1-hydroxy-3-(1H-indol-3-yl)propan-2-yl)-7,8,9-trimethoxy-3-phenyl-5,6-dihydropyrrolo[2,1-a]isoquinoline-2-carboxamide 1-Ethyl-3-(3-dimethylaminopropyl)carbodiimide hydrochloride (71 mg) was added to a solution of intermediate 60g (93 mg), triethylamine (102 µl), 1-hydroxybenzotriazole (34 mg), cesium carbonate (200 mg) and D-tryptophanol (56 mg) in dry DMF (1 ml), stirring for 70 hours at room temperature. The solvents were removed under vacuum and the residue obtained was partitioned between water and ethyl acetate. The aqueous phase was re-extracted with ethyl acetate (2×) and the combined organic layers were passed through a hydrophobic frit and concentrated to dryness under vacuum. The residue was purified by chromatography on silica gel eluting with DCM and increasing amounts of methanol (max. 10%). The pure fractions were collected.

Yield: 48 mg

¹H NMR δ (ppm) (CHCl₃-d): 8.04-7.96 (1H, m), 7.53 (1H, m, J=7.90 Hz), 7.35-7.1 (8H, m), 6.91 (2H, d, J=8.63 Hz), 6.82 (1H, d, J=2.32 Hz), 5.61 (1H, d, J=6.90 Hz), 4.32-4.26 (1H, m), 3.93-3.80 (9H, s), 3.73 (2H, q, J=6.61 Hz), 3.67-3.60 (1H, m), 3.53 (1H, Dt, J=11.00, 5.40 Hz), 3.11 (1H, t, J=5.56 Hz)), 3.98-3.88 (2H, m), 2.85-2.71 (2H, m)

Example 61

(R)—N-(1-hydroxy-3-(1H-indol-3-yl)propan-2-yl)-7,8,9-trimethoxy-3-(thiophen-2-yl)-5,6-dihydropyrrolo[2,1-a]isoquinoline-2-carboxamide Compound 61 was prepared in an analogous fashion as described for example 60.

¹H NMR δ (ppm) (CHCl₃-d): 8.05 (1H, s), 7.57 (1H, d, J=7.90 Hz), 7.39-7.34 (2H, m), 7.2 (1H, m), 7.15-7.09 (1H, m), 6.97-6.88 (5H, m), 5.87 (1H, d, J=6.91 Hz), 4.38-4.30 (1H, m), 3.89 (10H, m), 3.80-3.71 (2H, m), 3.72-3.64 (1H, m), 3.60-3.52 (1H, Dtm), 3.09 (1H, t, J=5.51 Hz)), 2.97-2.74 (4H, m).

Example 62

(R)-3-(3-fluorophenyl)-N-(1-hydroxy-3-(1H-indol-3-yl)propan-2-yl)-7,8,9-trimethoxy-5,6-dihydropyrrolo[2,1-a]isoquinoline-2-carboxamide Compound 62 was prepared in an analogous fashion as described for example 60.

¹H NMR δ (ppm) (CHCl₃-d): 8.09-7.99 (1H, m), 7.57 (1H, m, J=7.89 Hz), 7.37 (1H, d, J=8.09 Hz), 7.15-7.09 (1H, m), 7.05-6.99 (3H, m), 6.89-6.85 (2H, m), 6.81 (1H, s), 5.70 (1H, d, J=6.98 Hz), 4.37-4.29 (1H, m), 3.89 (9H, s), 3.78-3.64 (3H, m), 3.59 (1H, Dd, J=10.97, 5.87 Hz), 3.08 (1H, s), 2.96-2.79 (4H, m)

Example 63

(R)—N-(1-hydroxy-3-(1H-indol-3-yl)propan-2-yl)-8,9,10-trimethoxy-3-phenyl-5,6-dihydropyrrolo[2,1-a]isoquinoline-2-carboxamide Compound 63 was prepared in an analogous fashion as described for example 60, but starting from 3,4,5-trimethoxybenzaldehyde.

¹H NMR δ (ppm) (CHCl₃-d): 8.04-7.96 (1H, m), 7.55-7.50 (1H, m), 7.35-7.2 (5H, m), 7.19-7.08 (3H, m), 6.85 (1H, d, J=2.30 Hz), 6.52 (1H, s), 5.63 (1H, d, J=6.78 Hz), 4.33-4.27 (1H, m), 3.96 (3H, s), 3.93 (3H, s), 3.85 (3H, s), 3.76 (2H, t, J=6.45 Hz), 3.68-3.62 (1H, m), 3.53 (1H, Dt, J=11.00, 5.41 Hz), 3.19 (1H, t, J=5.54 Hz)), 2.92-2.72 (4H, m).

Example 64

(R)—N-(1-hydroxy-3-(1H-indol-3-yl)propan-2-yl)-8,9,10-trimethoxy-3-(thiophen-2-yl)-5,6-dihydropyrrolo[2,1-a]isoquinoline-2-carboxamide Compound 64 was prepared in an analogous fashion as described for example 60, but starting from 3,4,5-trimethoxybenzaldehyde.

$^1$H NMR δ (ppm) (CHCl$_3$-d): 8.04 (1H, s), 7.57 (1H, d, J=7.92 Hz), 7.40-7.32 (2H, m), 7.28-7.05 (6H, m), 6.96-6.91 (3H, m), 6.52 (1H, s) 5.86 (1H, d, J=6.82 Hz), 4.38-4.30 (1H, m), 3.98-3.74 (10H, m), 3.72-3.64 (1H, m), 3.57 (1H, d, J=10.07 Hz), 3.14 (1H, s), 2.94-2.76 (4H, m).

Example 65

(R)-3-(3-fluorophenyl)-N-(1-hydroxy-3-(1H-indol-3-yl)propan-2-yl)-8,9,10-trimethoxy-5,6-dihydropyrrolo[2,1-a]isoquinoline-2-carboxamide Compound 65 was prepared in an analogous fashion as described for example 60, but starting from 3,4,5-trimethoxybenzaldehyde.

$^1$H NMR δ (ppm) (CHCl$_3$-d): 8.04 (1H, s), 7.57 (1H, d, J=7.90 Hz), 7.36 (1H, d, J=8.09 Hz), 7.13-6.97 (5H, m), 6.92 (1H, d, J=2.30 Hz), 6.52 (1H, s), 6.73 (1H, d, J=6.83 Hz), 4.37-4.29 (1H, m), 3.90 (9H, s), 3.84-3.66 (3H, m), 3.60 (1H, Dd, J=10.98, 5.95 Hz), 3.16 (1H, s), 2.96-2.81 (4H, m)

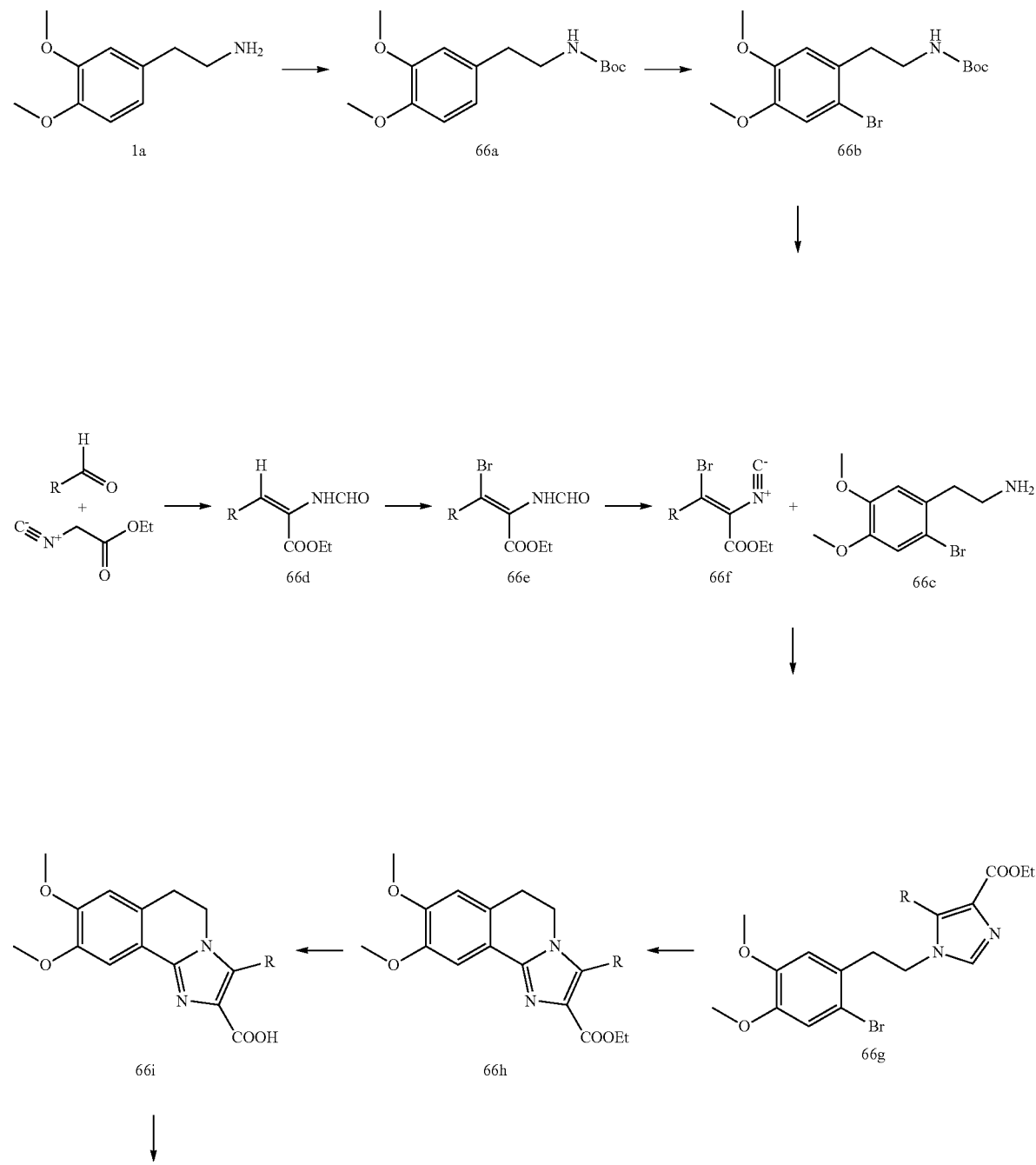

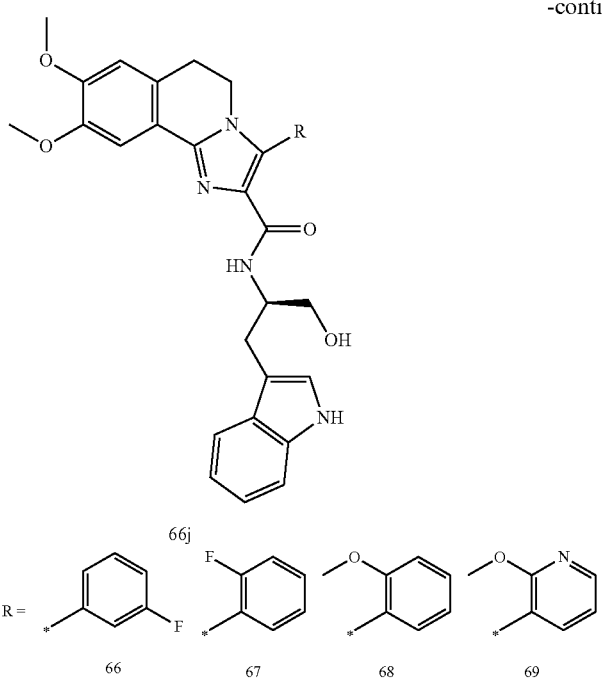

Example 66

(R)-3-(3-fluorophenyl)-N-(1-hydroxy-3-(1H-indol-3-yl)propan-2-yl)-8,9-dimethoxy-5,6-dihydroimidazo[2,1-a]isoquinoline-2-carboxamide (a). tert-butyl 3,4-dimethoxyphenethylcarbamate To a solution of compound 1a was added potassium carbonate (49.7 g). (Boc)₂O (52.3 g) was added dropwise in 1 hour. The reaction mixture was stirred at room temperature for 2 hours. The reaction mixture was concentrated and water was added. The product was extracted into ethyl acetate. The organic phase was dried over Na₂SO₄, filtered and concentrated in vacuo. The crude product was purified by chromatography on silica gel eluting with heptane and increasing amounts of ethyl acetate to give the product as a pale solid.
Yield: 25 g
MS (ESI) m/z: 282 (M+H)⁺.

(b). tert-butyl 2-bromo-4,5-dimethoxyphenethylcarbamate

To a solution of compound 66a (1 g) in DCM (16 ml) and a aqueous saturated NaHCO₃ solution (16 ml) was added dropwise bromine (0.75 g) at 0° C. and stirred for another 1 hour. The reaction mixture was stirred for an additional 2 hours at room temperature. A aqueous saturated sodium thiosulfate solution was added and the product was extracted into DCM. The organic phase was dried (MgSO₄), filtered and concentrated. The crude product was purified by chromatography on silica, eluting with heptane and increasing amounts of ethyl acetate to give the compound.
Yield: 1.22 g
¹H NMR δ (ppm) (CHCl₃-d): 6.98 (s, 1H), 6.71 (s, 1H), 4.53-4.62 (m, 1H), 3.84 (s, 6H), 3.33 (t, 2H, J=7.2 Hz), 3.33 (t, 2H, J=7.2 Hz), 1.41 (d, 9H, J=1.2 Hz).

(c). 2-(2-bromo-4,5-dimethoxyphenyl)ethanamine

To a solution of compound 66b (1.22 g) in DCM (2 ml) was added dropwise 4N HCl/ethyl acetate (20 ml) and stirred for 1 hour at room temperature. The reaction mixture was concentrated, a saturated aqueous NaHCO₃ solution was added and the product was extracted into ethyl acetate. The organic phase was dried over Na₂SO₄, filtered and concentrated to give the crude product.
Yield: 0.8 g
¹H NMR δ (ppm)(DMSO-d): 7.50-8.20 (m, 3H), 7.10 (s, 1H), 6.92 (s, 1H), 3.72 (s, 3H), 3.71 (s, 3H), 2.91-2.98 (m, 2H), 2.81-2.90 (m, 2H).

(d). (E)-ethyl 3-(3-fluorophenyl)-2-formamidoacrylate

To a suspension of sodium hydride (6 g) in THF (50 ml) was added dropwise a solution of 3-fluorobenzaldehyde (6 g) and ethyl iso-cyano-acetic ester (5 g) in THF (50 ml). The reaction was stirred for 2 hours at room temperature. The reaction mixture was quenched with a aqueous saturated NH₄Cl solution and the aqueous layer was extracted with ethyl acetate. The organic phase was dried over Na₂SO₄, filtered and concentrated. The crude product was purified by chromatography on silica gel eluting with heptane and increasing amount of ethyl acetate.
Yield: 5 g
¹H NMR δ (ppm) (CHCl₃-d): 8.20-8.35 (m, 1H), 6.96-7.43 (m, 6H), 4.30-4.40 (m, 2H), 1.37-1.42 (m, 3H).

(e). (Z)-ethyl 3-bromo-3-(3-fluorophenyl)-2-formamidoacrylate

A solution of compound 66d (5 g) and N-bromosuccinimide (4.5 g) in carbon tetrachloride (150 ml) was heated under reflux overnight. The reaction mixture was concentrated and the residue was purified by chromatography on silica gel with heptane and increasing amounts of ethyl acetate.

Yield: 3.6 g $^1$H NMR δ (ppm) (CHCl$_3$-d): 8.31 (s, 1H), 7.25-7.43 (m, 2H), 7.03-7.16 (m, 3H), 4.05 (q, 2H, J=7.2 Hz), 0.98 (t, 3H, J=7.2 Hz).

(f). (Z)-ethyl 3-bromo-3-(3-fluorophenyl)-2-isocyanoacrylate

To a solution of compound 66e (5 g) in DCM (50 ml) was added triethylamine (3 eq). At 0° C. phosphorus oxychloride (12.2 g) was added dropwise in 20 min. The reaction mixture was stirred at room temperature for 2 hours. The mixture was added dropwise to a potassium carbonate (120 g, 500 ml) solution in water and extracted with DCM. The organic phase was dried over Na$_2$SO$_4$, filtered and concentrated to give the product as a brown oil.

Yield: 3.5 g

MS (ESI) m/z: 298, 300 (M+H)$^+$

(g). ethyl 1-(2-bromo-4,5-dimethoxyphenethyl)-5-(3-fluorophenyl)-1H-imidazole-4-carboxylate A solution of compound 66c and compound 69f in DMF was heated to 120° C. for 2 hours. The reaction mixture was concentrated, water was added and the product was extracted into ethyl acetate. The organic phase was dried over Na$_2$SO$_4$, filtered and concentrated to give the desired product.

Yield: 114 mg

MS (ESI) m/z: 477, 479 (M+H)$^+$

(h). ethyl 3-(3-fluorophenyl)-8,9-dimethoxy-5,6-dihydroimidazo[2,1-a]isoquinoline-2-carboxylate To a solution of compound 66g (140 mg, crude) in dimethylacetamide (3 ml) were added potassium carbonate (221 mg) and tetrakis(triphenylphosphine)palladium(0) (26 mg) under N$_2$. The reaction was stirred at room temperature for 5 minutes. The reaction mixture was heated to 140° C. overnight. The solid was filtered off and the filtrate was concentrated. The crude product was used without purification in the next step.

Yield 100 mg

MS (ESI) m/z: 395 (M+H)$^+$

(i). 3-(3-fluorophenyl)-8,9-dimethoxy-5,6-dihydroimidazo[2,1-a]isoquinoline-2-carboxylic Acid To a solution of compound 66h in THF/water (2 ml/2 ml) was added lithium hydroxide (50 mg). The reaction mixture was stirred at room temperature overnight. The reaction mixture was concentrated, water was added and extracted with ethyl acetate. The aqueous layer was acidified with concentrated HCl to pH=3 and then extracted with ethyl acetate. The organic phase was dried over Na$_2$SO$_4$, filtered and concentrated to give the desired product.

Yield: 60 mg

MS (ESI) m/z: 369 (M+H)$^+$

(j). (R)-3-(3-fluorophenyl)-N-(1-hydroxy-3-(1H-indol-3-yl)propan-2-yl)-8,9-dimethoxy-5,6-dihydroimidazo[2,1-a]isoquinoline-2-carboxamide To a solution of compound 66i (60 mg, crude) in DMF (2 ml) were added tryptophanol (50 mg), TBTU (20 mg) and triethylamine (0.5 ml). The reaction mixture was stirred at rt for 30 minutes. The reaction mixture was concentrated the residue was purified by preparative HPLC eluting with acetonitrile and water to give the desired product.

Yield: 5 mg

MS (ESI) m/z: 541 (M+H)$^+$ $^1$H NMR δ (ppm) (CH$_3$OH-d): 7.55-7.65 (m, 3H), 7.37-7.42 (m, 1H), 7.21-7.37 (m, 3H), 7.08-7.12 (m, 2H), 6.95-7.08 (m, 2H), 4.32-4.42 (m, 1H), 4.02 (t, 2H, J=7.6 Hz), 3.91-3.98 (m, 5H), 3.59-3.62 (m, 2H), 3.15 (t, 2H, J=7.6 Hz), 2.97-3.11 (m, 2H)

Example 67

3-(2-fluorophenyl)-N—((R)-1-hydroxy-3-(1H-indol-3-yl)propan-2-yl)-8,9-dimethoxy-5,6-dihydroimidazo[2,1-a]isoquinoline-2-carboxamide Compound 67 was prepared in analogous fashion as described for example 66.

MS (ESI) m/z: 541 (M+H)$^+$ $^1$H NMR δ (ppm) (CH$_3$OH-d): 7.48-7.52 (m, 3H), 7.32-7.41 (m, 1H), 7.21-7.40 (m, 3H), 7.03-7.11 (m, 2H), 6.89-6.97 (m, 2H), 4.30-4.38 (m, 1H), 3.89-3.96 (m, 2H), 3.82-3.89 (m, 6H), 3.55-3.62 (m, 2H), 3.08 (t, 2H, J=7.6 Hz), 2.92-3.05 (m, 2H)

Example 68

N—((R)-1-hydroxy-3-(1H-indol-3-yl)propan-2-yl)-8,9-dimethoxy-3-(2-methoxyphenyl)-5,6-dihydroimidazo[2,1-a]isoquinoline-2-carboxamide Compound 68 was prepared in analogous fashion as described for example 66.

MS (ESI) m/z: 553 (M+H)$^+$ $^1$H NMR δ (ppm) (CH$_3$OH-d): 7.45-7.57 (m, 2H), 7.11-7.32 (m, 4H), 7.02-7.10 (m, 2H), 6.75-7.01 (m, 2H), 4.45-4.48 (m, 1H), 3.81-4.10 (m, 8H), 3.72-3.85 (m, 3H), 3.45-3.60 (m, 2H), 3.08-3.18 (m, 2H), 2.92-3.05 (d, 1H, J=9.6 Hz), 2.60-2.81 (d, 1H, J=7.2 Hz). 7.40-7.52 (m, 3H), 7.19-7.42 (m, 1H), 6.99-7.15 (m, 3H), 6.82-6.98 (m, 4H), 4.24-4.40 (m, 1H), 3.73-3.93 (m, 8H), 3.72 (s, 3H), 3.42-3.52 (m, 2H), 2.95 (dd, 1H, J=7.2, 14.4 Hz), 2.85 (dd, 1H, J=7.6, 15.6 Hz)

Example 69

N—((R)-1-hydroxy-3-(1H-indol-3-yl)propan-2-yl)-8,9-dimethoxy-3-(2-methoxypyridin-3-yl)-5,6-dihydroimidazo[2,1-a]isoquinoline-2-carboxamide Compound 69 was prepared in analogous fashion as described for example 66.

MS (ESI) m/z: 554 (M+H)$^+$ $^1$H NMR δ (ppm) (CH$_3$OH-d): 8.20-8.32 (m, 1H), 7.46-7.65 (m, 3H), 7.17-7.37 (m, 1H), 6.85-7.05 (m, 5H), 4.27-4.48 (m, 1H), 3.75-4.02 (m, 11H), 3.52-3.62 (m, 2H), 3.05 (d, 2H, J=7.6 Hz), 2.92-3.02 (m, 2H)

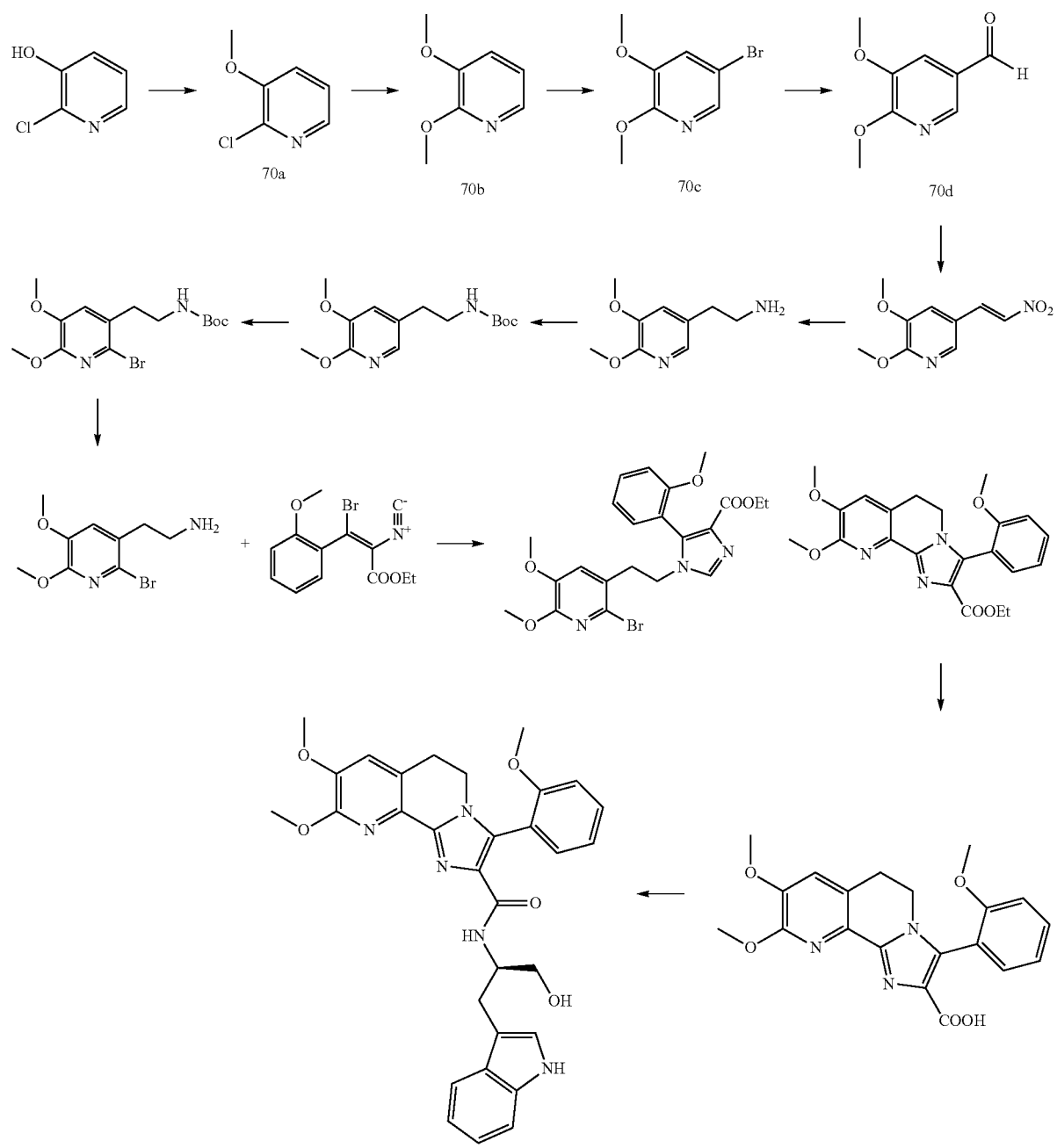

Example 70

N—((R)-1-hydroxy-3-(1H-indol-3-yl)propan-2-yl)-8,9-dimethoxy-3-(2-methoxyphenyl)-5,6-dihydroimidazo[1,2-h][1,7]naphthyridine-2-carboxamide (a). 2-chloro-3-methoxypyridine To a solution of 2-chloro-pyridin-3-ol (100 g) in DMSO (1 L) was added potassium carbonate (320 g). Methyliodide was added dropwise. The reaction mixture was heated to 50° C. overnight. The reaction mixture poured into water and extracted with ethyl acetate. The organic phase was washed with brine, dried over $Na_2SO_4$, filtered and concentrated to give the desired compound.

Yield: 110 g (b). 2,3-dimethoxypyridine

To a solution of 2-chloro-3-methoxy-pyridine (110 g) in DMSO (1 L) was added sodium methoxide (124 g). The reaction mixture was heated to 80° C. overnight. The reaction mixture was poured into 3 L water and extracted with ethyl acetate. The organic phase was washed with brine, dried over $Na_2SO_4$, filtered and concentrated to give the crude product.

Yield: 105 g $^1$H NMR δ (ppm) ($CH_3OH$-d): 7.70 (t, 1H, J=1.2 and 5.2 Hz), 7.01 (t, 1H, J=1.2 and 8.0 Hz), 6.81 (q, 1H, J=5.2 and 7.8 Hz), 4.00 (s, 3H), 3.85 (s, 3H).

(c). 5-bromo-2,3-dimethoxypyridine

To a solution of 2,3-dimethoxy-pyridine (104 g) in DCM (1 L) and a saturated aqueous solution of NaHCO$_3$ (1.6 ml) at 0° C. was added bromine (120 g). The reaction was stirred for 2 hours at 0° C. The reaction mixture was quenched with Na$_2$SO$_3$ (saturated in water, 500 ml) and stirred for 30 min. The aqueous layer was extracted with DCM, and the organic phase was washed with brine, dried over Na$_2$SO$_4$, filtered and concentrated. The crude product was purified by chromatography on silica gel with heptane and increasing amounts of ethyl acetate.

Yield: 100 g $^1$H NMR δ (ppm) (CHCl$_3$-d): 7.70 (d, 1H, J=2.0 Hz), 7.06 (s, 1H, J=2.0 Hz), 3.92 (s, 3H), 3.80 (s, 3H).

(d). 5,6-dimethoxynicotinaldehyde

To a solution of 5-Bromo-2,3-dimethoxy-pyridine (43 g) in THF (500 ml) at −78° C. was added n-butyllithium (191 mmol). After stirring for 30 minutes at −78° C. DMF (28.8 g) was added dropwise and the reaction mixture was stirred at −78° C. for 2 hours. The reaction mixture was quenched with NH$_4$Cl (saturated in water, 500 ml). The aqueous layer was extracted with ethyl acetate, the organic phases were washed with brine, dried over Na$_2$SO$_4$, filtered and concentrated. The crude product was purified by chromatography on silica eluting with heptane with increasing amounts of ethyl acetate.

Yield: 33 g

Compound 70 was further prepared in analogous fashion as described for compound 60b and example 66.

MS (ESI) m/z: 554 (M+H)$^+$ $^1$H NMR δ (ppm) (CH$_3$OH-d): 7.45-7.57 (m, 2H), 7.11-7.32 (m, 4H), 7.02-7.10 (m, 2H), 6.75-7.01 (m, 2H), 4.45-4.48 (m, 1H), 3.81-4.10 (m, 8H), 3.72-3.85 (m, 3H), 3.45-3.60 (m, 2H), 3.08-3.18 (m, 2H), 2.92-3.05 (d, 1H, J=9.6 Hz), 2.60-2.81 (d, 1H, J=7.2 Hz).

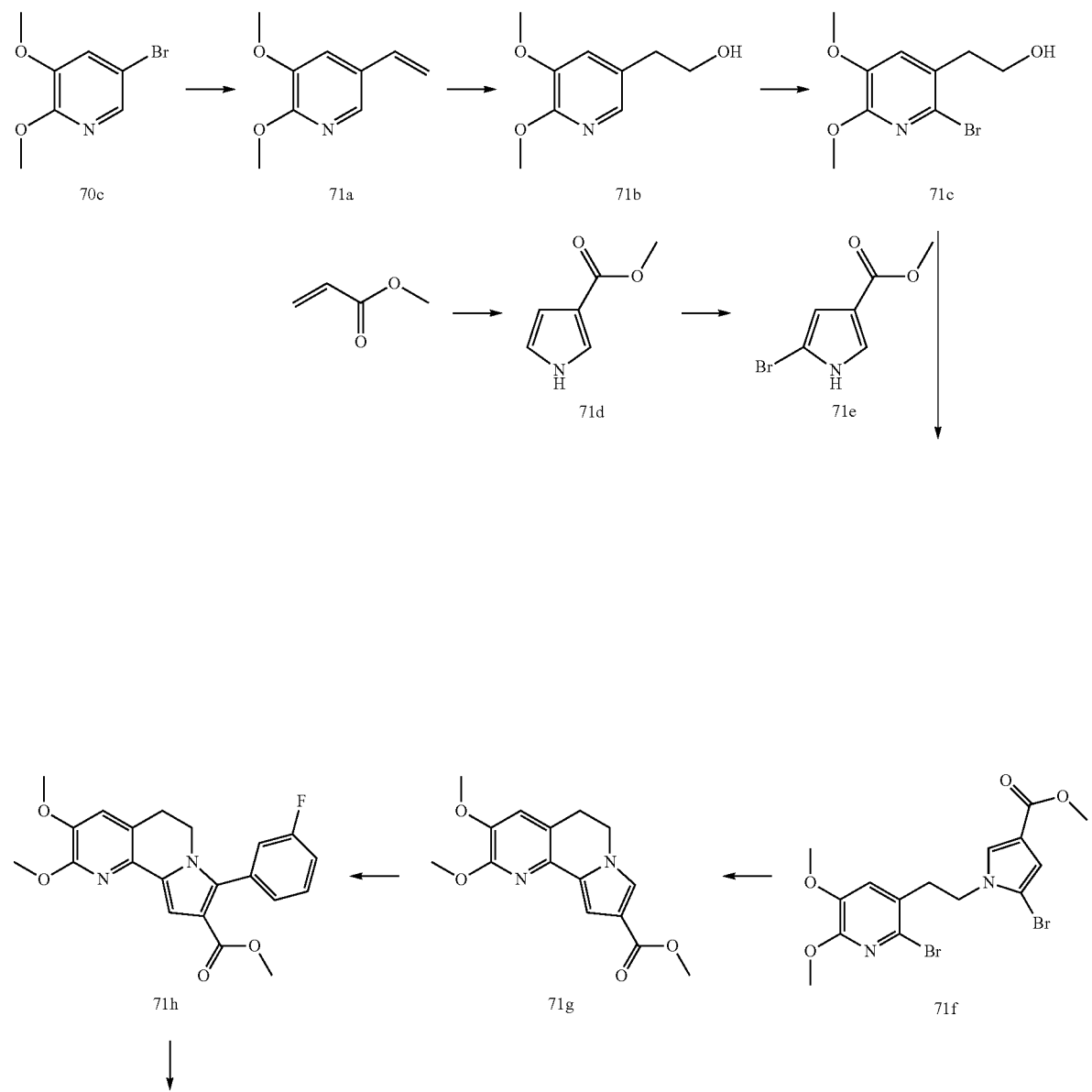

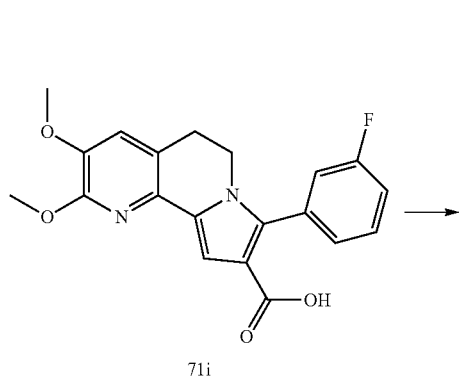

71i

-continued

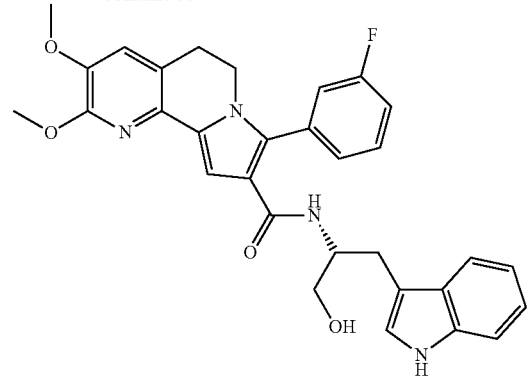

71j

Example 71

N—((R)-1-hydroxy-3-(1H-indol-3-yl)propan-2-yl)-8,9-dimethoxy-3-(2-methoxyphenyl)-5,6-dihydroimidazo[1,2-h][1,7]naphthyridine-2-carboxamide (a). 2,3-dimethoxy-5-vinylpyridine To a stirred solution of compound 70c (30 g) in toluene (200 ml) were added Tetrakis(triphenylphosphine)palladium (0) (7.9 g) and tributyl(vinyl)stannane (66 g). The resulting mixture was heated to 110° C. overnight. The reaction was cooled and filtered, the filtrate was concentrated. The crude product was purified by chromatography on silica gel (petrol:ethyl acetate=20:1) to give the desired compound.

Yield: 11 g $^1$H NMR δ (ppm) (CHC$_3$-d): 7.685 (d, 1H, J=0.8 Hz), 7.152 (d, 1H, J=0.8 Hz), 6.691-6.620 (m, 1H), 5.632 (d, 1H, J=8.8 Hz), 4.020 (s, 3H), 3.906 (s, 3H).

(b). 2-(5,6-dimethoxypyridin-3-yl)ethanol

To a stirred solution of compound 71a (11 g) in THF (120 ml), was added borane (20 ml, 10 mol/L). The mixture was heated under reflux for 2 hours. The reaction mixture was cooled and sodium hydroxide (35.5 ml, 15% in water) was added slowly to the mixture, followed by water (15.1 ml, 30%). The resulting mixture was heated to 50° C. and stirred for 30 minutes. Extracted with ethyl acetate, washed with brine dried over Na$_2$SO$_4$, filtered and concentrated. The crude product was purified by chromatography on silica gel (petrol:ethyl acetate=3:1) to give the desired compound.

Yield: 3.6 g.

MS (ESI) m/z: 184 (M+H)$^+$ (c). 2-(2-bromo-5,6-dimethoxypyridin-3-yl)ethanol

To a solution of compound 71b (3.6 g) in DCM (30 ml) and a aqueous saturated NaHCO$_3$ solution (30 ml) at 0° C. was added dropwise bromine (1.32 ml). The reaction was stirred for 1 hour at 0° C. and then warmed to room temperature for additional 1 hour. The reaction mixture was quenched with saturated sodium thiosulfate (saturated in water 100 ml). The aqueous layer was extracted with DCM. The organic phase was dried (MgSO$_4$), filtered and concentrated to give the desired compound.

Yield: 4.1 g

MS (ESI) m/z: 262, 264 (M+H)$^+$ (d). methyl 1H-pyrrole-3-carboxylate

To a solution of potassium-tert-butoxide (105 g) in THF (1.2 L) was added dropwise a solution of methyl acrylate (66 g) and toluenesulfonylmethyl isocyanide (150 g) in THF (300 ml). The resulting mixture was stirred at room temperature for 2 h. The reaction was quenched with water and extracted with ethyl acetate. The organic phase was dried (MgSO$_4$), filtered and concentrated. The crude product was purified by chromatography on silica gel (Petrol:ethyl acetate=5:1) to give the desired compound.

Yield: 40 gram $^1$H NMR δ (ppm) (CHCl$_3$-d): 8.815 (br, 1H), 7.404 (s, 1H), 6.729 (d, 1H, J=1.2 Hz), 6.621 (d, 1H, J=0.4 Hz), 3.788 (s, 3H).

(e) methyl 5-bromo-1H-pyrrole-3-carboxylate

To a solution of compound 71d (40 g) in THF (60 ml) was added N-bromosuccinimide (67.6 g) portion wise at −78° C. The reaction mixture was allowed to stir at room temperature overnight. The reaction mixture was concentrated. The crude product was purified by chromatography on silica gel, eluting with (Petrol:ethyl acetate=10:1) to give the desired compound.

Yield: 38 g $^1$H NMR δ (ppm) (CHCl$_3$-d): 8.625 (br, 1H), 7.364 (dd, 1H, J$_1$=2.0 Hz J$_2$=2.8 Hz), 6.588 (dd, 1H, J$_1$=2.0 Hz J$_2$=2.4 Hz), 3.808 (s, 3H).

(f) methyl 5-bromo-1-(2-(2-bromo-5,6-dimethoxypyridin-3-yl)ethyl)-1H-pyrrole-3-carboxylate To a solution of compound 71c (3.1 g) in THF (60 ml) were added triphenylphosphine (3.72 g), DIAD (2.81 ml), DIPEA (2.35 ml) and compound 71e (2.35 ml). The resulting mixture was heated under reflux for 2 hours. The reaction mixture was cooled and filtered, the filtrate was concentrated. The crude product was purified by column chromatography on silica gel eluting with (Petrol:ethyl acetate=10:1) to give the desired compound.

Yield: 4 g $^1$H NMR δ (ppm) (CHCl$_3$-d): 7.170 (s, 1H), 6.567 (d, 1H, J=1.2 Hz), 6.367-6.191 (m, 1H), 4.177-4.100 (m, 2H), 3.989 (s, 3H), 3.759 (s, 3H), 3.666 (s, 3H), 3.043 (t, 2H, J=6.8 Hz).

(g) methyl 2,3-dimethoxy-5,6-dihydropyrrolo[1,2-h][1,7]naphthyridine-9-carboxylate To a solution of compound 71f (3.5 g, crude) in toluene (50 ml) were added Pd(PPh$_3$)$_2$Cl$_2$ (160 mg) and (n-Bu$_3$Sn)$_2$ (2.5 ml). The resulting mixture was heated to 120° C. overnight. The reaction was cooled and filtered, the filtrate was concentrated. The crude product was purified by column chromatography on silica gel, eluting with (Petrol:ethyl acetate=10:1) to give the desired compound.
Yield: 300 mg
MS (ESI) m/z: 289 (M+H)$^+$ (h) methyl 8-(3-fluorophenyl)-2,3-dimethoxy-5,6-dihydropyrrolo[1,2-h][1,7]naphthyridine-9-carboxylate To a solution of compound 71g (60 mg) in dioxane (5 ml) were added triphenylphosphine (10 mg), Palladium(II) acetate (5 mg), 1-fluoro-3-iodo-benzene (93 mg) and cesium carbonate (137 mg). The resulting mixture was heated to 120° C. overnight. The reaction was cooled and filtered and the filtrate was concentrated. The crude product was purified by preparative HPLC, eluting with acetonitrile and water to give the desired compound.
Yield: 25 mg
MS (ESI) m/z: 383 (M+H)$^+$ (i) 8-(3-fluorophenyl)-2,3-dimethoxy-5,6-dihydropyrrolo[1,2-h][1,7]naphthyridine-9-carboxylic Acid To a solution of compound 71h (25 mg) in methanol (1 ml), water (1 ml) and THF (1 ml), was added potassium hydroxide (73 mg). The reaction mixture was heated to 60° C. overnight. The mixture was concentrated and water was added. The mixture was acidified by concentrated HCl to pH=2 and extracted with DCM. The organic phase was dried (MgSO$_4$), filtered and concentrated to give the desired compound.
Yield: 29 mg
MS (ESI) m/z: 369 (M+H)$^+$ (j). N—((R)-1-hydroxy-3-(1H-indol-3-yl)propan-2-yl)-8,9-dimethoxy-3-(2-methoxyphenyl)-5,6-dihydroimidazo[1,2-h][1,7]naphthyridine-2-carboxamide To a solution of compound 71i in DCM were added compound tryptophanol (50 mg, TBTU (20 mg) and triethylamine (0.5 ml). The reaction was stirred at room temperature for 30 min. The reaction mixture was purified by preparative HPLC, eluting with acetonitrile and water to give the desired compound.
Yield: 8 mg
MS (ESI) m/z: 541 (M+H)$^+$
$^1$H NMR δ (ppm) (CHCl3-d): 7.998 (s, 1H), 7.564 (d, 1H, J=4.0 Hz), 7.361 (d, 1H, J=4.0 Hz), 7.222 (t, 1H, J=2.0 Hz), 7.198-7.119 (m, 1H), 7.053-7.011 (m, 4H), 6.931 (s, 1H), 6.857 (s, 1H), 5.860 (d, 1H, J=2.8 Hz), 4.359-4.327 (m, 1H), 4.075 (s, 3H), 3.879 (s, 3H), 3.817 (t, 2H, J=6.8 Hz), 3.727-3.611 (m, 2H), 2.997-2.859 (m, 5H).

Example 72

Antagonistic Activity of Compounds at the Human FSH Receptor Expressed in CHO Cells Antagonistic activity of the compounds at the human FSH receptor was determined in Chinese Hamster Ovary (CHO) cells stably transfected with the human FSH receptor and cotransfected with a cAMP responsive element (CRE)/promotor directing the expression of a firefly luciferase reporter gene. Binding of the compounds to the Gs protein-coupled FSH receptor will result in an increase of cAMP, which in turn will induce an increased transactivation of the luciferase reporter. The cells (7,500 cells/well of a 384 well plate) were incubated in Dulbecco' minimal essential F12 modified medium (Invitrogen), supplemented with 1 µg/ml bovine insulin, 5 µg/ml human apo-transferrin, 100 U/ml penicillin G and 100 µg/ml streptomycin with the test compounds (concentration between 0.316 nM and 10.0 µM) in duplicate together with 49 µM recFSH (which, at this concentration in the absence of test compound, induces 80% of the maximal luciferase stimulation) in a humidified atmosphere (95%) at 5-7% CO$_2$ and 37° C. The final concentration of DMSO was 1%. After 4 hours of incubation, plates were allowed to adjust to room temperature for 1 hour. Then, SteadyLite (PerkinElmer) solution was added to the wells and cells were allowed to lyse for at least 1 hour at room temperature. Subsequently, luciferase activity was measured in a luminescence counter. The signal is expressed as counts per second (cps). The IC50 (concentration of test compound causing half-maximal (50%) inhibition of the maximally attainable inhibition of the luciferase stimulation by the compound) and efficacy of the compounds were determined using the software program MathIQ (version 2.3, ID Business Solutions Limited).

The compounds of all examples have an IC50 of 10$^{-5}$ M or lower. The compounds of examples 1-4, 9, 15, 30-32, 39, 46-48, 51 and 66-68 have an IC50 of less than 10$^{-6}$ M and more than 10$^{-7}$ M. The compounds of examples 5-8, 10-14, 16-19, 22-29, 33-38, 40-45, 49, 50, 52-65 and 70 have an IC50 of less than 10$^{-7}$ M.

Example 73

Functional Assay for Assessing hFSHR Antagonistic Activity of Test Compounds in Human Granulosa Cell Cultures Human granulosa cells were obtained in the course of follicular aspiration for retrieval of matured oocytes during routine IVF procedures approximately 36 hours after hCG administration to the patient. Follicular fluid was collected as one batch per patient and after oocyte removal centrifuged for 5 minutes at 350 g at room temperature (RT). The pellet was resuspended in 5 ml collagenase (0.1%) containing isolation medium, layered on 5 ml of Histopaque-1077 and centrifuged (450 g for 20 minutes, RT) to separate the granulosa cells from the erythrocytes. The granulosa cells and other mononuclear cells (e.g. lymphocytes) were obtained from the interface and washed once with isolation medium (450 g, 20 minutes). After aspiration of the supernatant, the pellet was resuspended in isolation medium and transported from the hospital to the laboratory. The granulosa cells are pelleted by centrifugation (350 g, 5 minutes) and resuspended in a small volume of culture medium with 10% fetal calf serum (FCS). To facilitate cell dispersal the suspension was subjected to gentle mechanical dissociation.

Cell viability was determined by Trypan Blue exclusion and the granulosa cells were plated at a density of 25.000 viable cells/200 µl/well in culture medium with 10% FCS in collagen coated 96-wells plates, and cultured at 37° C. under a humidified atmosphere supplemented with 5% CO$_2$. Every 72 hours the cells are washed once with pre-warmed culture medium to remove dead cells, debris and non-adherent cells.

Seven days after the start of the culture, the cells are washed again with culture medium. Medium was aspirated and 250 µL isolation medium with isobutylmethylxanthine (IBMX) with human recombinant FSH (hrecFSH: 0 and 250 mU/mL) or with hrecFSH (250 mU/mL) in combination with test compound of example 5 was incubated for an additional 48 hours at 37° C., 5% $CO_2$. All test conditions were performed in triplicate. Subsequently, supernatant was collected in 96 well plates. Finally 25 µL supernatant was transferred to a new 96 deep-well plate and used for the determination of cAMP levels with the cAMP EIA kit (Amersham Life Sciences, cat. no RPN 225). Immediately after aspiration of the supernatant of the granulosa cells, 150 µL culture medium supplemented with 10 µM testosterone, was added to the wells. After 2 hours of incubation at 37° C., 5% $CO_2$, the supernatant was collected and used for the determination of estradiol levels with an estradiol-ELISA (DRG instruments, art. no. EIA-2693). Supernatants were diluted 1:300 in Dulbecco's phosphate buffered saline (DPBS, Hyclone Cat. No. SH30028.03) and a self-made calibration curve of estradiol in DPBS was used for the determination of estradiol levels in the supernatants.

The invention claimed is:
1. A compound according to Formula I

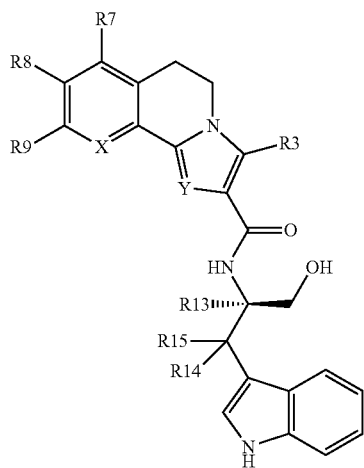

Formula I or a pharmaceutically acceptable salt thereof, wherein
X is C(R10) or N;
Y is N;
R3 is phenyl, (2-8C)heteroaryl, benzoyl, (2-8C)heteroarylcarbonyl, the phenyl or heteroaryl moieties of which may optionally be substituted with one or more substituents selected from R11, or
R3 is (1-6C)alkyl, (2-6C)alkenyl, (2-6C)alkynyl, (3-6C)cycloalkyl, (1-6C)alkylcarbonyl, (2-6C)alkenylcarbonyl, (2-6C)alkynylcarbonyl or (3-6C)cycloalkylcarbonyl;
R7 and R8 are independently H or (1-4C)alkoxy;
R9 is hydroxy or H, or
R9 is (1-6C)alkyl, (2-6C)alkenyl, (2-6C)alkynyl, (1-4C)alkoxy, (2-4C)alkenoxy, (3-6C)cycloalkyl, (3-6)cycloalkoxy, (3-6C)cycloalkyl(1-4C)alkoxy, (2-6C)heterocycloalkylcarbonyl, (di)[1-4C]alkylaminocarbonyl, (2-6C)heterocycloalkyl, the alkyl or (hetero)cycloalkyl moieties of which may optionally be substituted with one or more substituents selected from R12 or,
R9 is (2-8C)heteroaryl, phenyl, phenyl(1-4C)alkoxy, (2-8C)heteroaryl(1-4C)alkoxy, the phenyl or heteroaryl moieties of which may optionally be substituted with one or more substituents selected from R16;
R10 is H or (1-4C)alkoxy;
R11 is hydroxy, amino, halogen, nitro, trifluoromethyl, cyano, (1-4C)alkyl, (1-4C)alkoxy or (di)[1-4C]alkyl]amino;
R12 is hydroxy, amino, halogen, cyano, (1-4C)alkoxy or (di)[1-4C)alkyl]amino;
R13 and R14 are independently H or (1-3C)alkyl;
R15 is H, (1-3C)alkyl, or
R14 and R15 may be joined in a (3-6C)cycloalkyl ring; and
R16 is hydroxy, amino, halogen, nitro, trifluoromethyl, cyano, (1-4C)alkyl, (1-4C)alkoxy or (di)[1-4C)alkyl]amino.

2. The compound according to claim 1 wherein
R8 is (1-4C)alkoxy; and
R9 is hydroxy or
R9 is (1-6C)alkyl, (2-6C)alkenyl, (1-4C)alkoxy, (2-4C)alkenoxy, (3-6)cycloalkoxy, (3-6C)cycloalkyl(1-4C)alkoxy, (2-6C)heterocycloalkylcarbonyl, (di)[1-4C]alkylaminocarbonyl, the alkyl or (hetero)cycloalkyl moieties of which may optionally be substituted with one or more substituents selected from R12 or,
R9 is (2-8C)heteroaryl, phenyl(1-4C)alkoxy, the phenyl or heteroaryl moieties of which may optionally be substituted with one or more substituents selected from R16; or a pharmaceutically acceptable salt thereof.

3. The compound according to claim 2 wherein R13, R14 and R15 are H;
or a pharmaceutically acceptable salt thereof.

4. The compound according to claim 3 wherein
R9 is (1-6C)alkyl, (1-4C)alkoxy or (3-6C)cycloalkyl(1-4C)alkoxy, the alkyl moieties of which may optionally be substituted with one or more substituents selected from R12; or
R9 is (2-8C)heteroaryl or phenyl(1-4C)alkoxy, the phenyl or heteroaryl moieties of which may optionally be substituted with one or more substituents selected from R16; or a pharmaceutically acceptable salt thereof.

5. The compound according to claim 4 wherein R3 is phenyl, (2-8C)-heteroaryl, benzoyl, (2-8C)heteroarylcarbonyl, the phenyl or heteroaryl moieties of which may optionally be substituted with one or more substituents selected from R11, or
R3 is (1-6C)alkyl, (2-6C)alkenyl, (1-6C)alkylcarbonyl or (3-6C)cycloalkylcarbonyl; or a pharmaceutically acceptable salt thereof.

6. The compound according to claim 5 wherein R3 is phenyl or (2-8C)heteroaryl, both optionally substituted with one or more substituents selected from R11 or a pharmaceutically acceptable salt thereof.

7. The compound according to claim 6 wherein X is C(R10); or a pharmaceutically acceptable salt thereof.

8. The compound according to claim 1 selected from the group of:
(R)-3-(3-fluorophenyl)-N-(1-hydroxy-3-(1H-indol-3-yl)propan-2-yl)-8,9-dimethoxy-5,6-dihydroimidazo[2,1-a]isoquinoline-2-carboxamide;
3-(2-fluorophenyl)-N-((R)-1-hydroxy-3-(1H-indol-3-yl)propan-2-yl)-8,9-dimethoxy-5,6-dihydroimidazo[2,1-a]isoquinoline-2-carboxamide;
N—((R)-1-hydroxy-3-(1H-indol-3-yl)propan-2-yl)-8,9-dimethoxy-3-(2-methoxyphenyl)-5,6-dihydroimidazo[2,1-a]isoquinoline-2-carboxamide;

N—((R)-1-hydroxy-3-(1H-indol-3-yl)propan-2-yl)-8,9-dimethoxy-3-(2-methoxypyridin-3-yl)-5,6-dihydroimidazo[2,1-a]isoquinoline-2-carboxamide;

N—((R)-1-hydroxy-3-(1H-indol-3-yl)propan-2-yl)-8,9-dimethoxy-3-(2-methoxyphenyl)-5,6-dihydroimidazo[1,2-h][1,7]naphthyridine-2-carboxamide;

or a pharmaceutically acceptable salt thereof.

9. A pharmaceutical composition which comprises a compound of formula I according to claim 1 or a pharmaceutically acceptable salt thereof and one or more pharmaceutically acceptable excipients.

10. A pharmaceutical composition according to claim 9, which further comprises at least one additional therapeutically active agent.

11. A method of treating endometriosis, pre-menopausal and peri-menopausal hormone-dependent breast cancer, uterine fibroids, or dysfunctional uterine bleeding, comprising administering a compound according to claim 1.

12. A method of contraception comprising administering a compound according to claim 1.

* * * * *